United States Patent
Wang et al.

(10) Patent No.: US 9,879,310 B2
(45) Date of Patent: *Jan. 30, 2018

(54) NANO/MICROSCALE VEHICLES FOR CAPTURE AND ISOLATION OF TARGET BIOMOLECULES AND LIVING ORGANISMS

(75) Inventors: Joseph Wang, San Diego, CA (US); Shankar Balasubramanian, Acton, MA (US); Daniel Kagan, Westfield, NJ (US); Susana Campuzano-Ruiz, Madrid (ES)

(73) Assignee: The Regents of the University of California, Oakland, CA (US)

( * ) Notice: Subject to any disclaimer, the term of this patent is extended or adjusted under 35 U.S.C. 154(b) by 645 days.

This patent is subject to a terminal disclaimer.

(21) Appl. No.: 13/983,034

(22) PCT Filed: Jan. 31, 2012

(86) PCT No.: PCT/US2012/023410
§ 371 (c)(1),
(2), (4) Date: Oct. 21, 2013

(87) PCT Pub. No.: WO2012/106384
PCT Pub. Date: Aug. 9, 2012

(65) Prior Publication Data
US 2014/0045179 A1    Feb. 13, 2014

Related U.S. Application Data

(60) Provisional application No. 61/438,233, filed on Jan. 31, 2011.

(51) Int. Cl.
*B01D 15/02*    (2006.01)
*B01D 15/38*    (2006.01)
(Continued)

(52) U.S. Cl.
CPC ....... *C12Q 1/6806* (2013.01); *B01D 15/3885* (2013.01); *B01J 20/22* (2013.01);
(Continued)

(58) Field of Classification Search
CPC .... B01D 15/02; B01D 15/38; B01D 15/3885; B01J 20/22; B01J 20/32; B01J 2220/4812;
(Continued)

(56) References Cited

U.S. PATENT DOCUMENTS 6,663,833 B1 *  12/2003  Stave ................. G01N 33/5302
                                                422/110
2002/0086335 A1 *  7/2002  Massey .................. B82Y 30/00
                                                435/7.1
(Continued)

OTHER PUBLICATIONS

Solovev et al, "Tunable catalytic tubular micro-pumps operating at low concentrations of hydrogen peroxide", Phys. Chem. Chem. Phys., 2011, vol. 13, pp. 10131-10135.*
(Continued)

*Primary Examiner* — Joseph Drodge
(74) *Attorney, Agent, or Firm* — Perkins Coie LLP

(57) ABSTRACT

Techniques, systems, devices and materials are disclosed for capturing, isolating and transporting target biomolecules and living organisms. In one aspect, a device includes a tube structured to include a large opening and a small opening that are on opposite ends of the tube, and a tube body connecting the openings and having a cross section spatially reducing in size from the large opening to the small opening, in which the tube includes a layered wall including an inner layer having a catalyst material that is reactive with a fuel fluid to produce bubbles exiting the tube from the large opening to propel the tube to move in the fuel fluid and an external layer formed of a material capable of being functionalized, and a molecular layer functionalized onto the
(Continued)

external layer of the tube and structured to attach to a targeted molecule in the fuel fluid.

47 Claims, 21 Drawing Sheets

(51) Int. Cl.
    B01J 20/22     (2006.01)
    B01J 20/32     (2006.01)
    G01N 33/53     (2006.01)
    C12Q 1/68      (2006.01)
    C12M 1/26      (2006.01)
    G01N 33/543    (2006.01)
    G01N 33/544    (2006.01)
    G01N 1/10      (2006.01)

(52) U.S. Cl.
    CPC .............. B01J 20/32 (2013.01); C12M 1/268
    (2013.01); C12Q 1/6834 (2013.01); G01N
    1/10 (2013.01); G01N 33/544 (2013.01);
    G01N 33/5436 (2013.01); G01N 33/54313
    (2013.01); G01N 33/54393 (2013.01); B01J
    2220/4812 (2013.01)

(58) Field of Classification Search
    CPC .. B01J 2220/4856; C12Q 1/68; C12Q 1/6806;
            C12Q 1/6834; G01N 1/10; G01N
            33/5436; G01N 33/54393; G01N 33/544;
            G01N 33/558; G01N 33/54313; C12M
            1/16; C12M 1/26; C12M 1/268; C12M
            1/28; C12M 1/128
    USPC ................ 210/263, 660; 422/502, 504, 507;
            436/514, 518, 536, 64, 86, 89, 178;
            435/6.14, 6.19, 7.1, 7.8, 287.2, 287.3,
            435/287.7, 287.8, 30, 309.1, 6.11, 6.12
    See application file for complete search history.

(56) References Cited

U.S. PATENT DOCUMENTS

| | | | | |
|---|---|---|---|---|
| 2003/0175850 A1* | 9/2003 | Ross | ................ | B01L 3/5027 435/34 |
| 2004/0209303 A1* | 10/2004 | Martin | ................ | C12N 11/00 435/6.11 |
| 2005/0112782 A1* | 5/2005 | Buechler | ........... | B01L 3/502746 436/514 |
| 2005/0281682 A1* | 12/2005 | Paxton | ................ | F04B 19/006 417/53 |
| 2010/0304359 A1* | 12/2010 | Egan | ................ | G01N 33/54366 435/5 |
| 2011/0270434 A1* | 11/2011 | Fischer | ................ | B82Y 5/00 700/117 |
| 2012/0269728 A1* | 10/2012 | Jen | ................ | B01D 15/3804 424/9.1 |
| 2012/0301903 A1* | 11/2012 | Putnam | ................ | G01N 21/05 435/7.92 |
| 2013/0084569 A1* | 4/2013 | Wang | ................ | C12Q 1/6816 435/6.11 |
| 2013/0241344 A1* | 9/2013 | Wang | ................ | H01L 29/872 310/300 |
| 2015/0013304 A1* | 1/2015 | Wang | ................ | F03G 7/005 60/204 |

OTHER PUBLICATIONS

Gibbs et al, "Autonomously motile catalytic nanomotors by bubble propulsion", Applied Physics Letters, vol. 94, 163104, 2009.*
Kagan et al, "Rapid Delivery of Drug Carriers Propelled and Navigated by Catalytic Nanoshuttles", Small, vol. 6, No. 23, pp. 2741-2747, 2010.*
Mei et al, "Versatile approach for integrative and functionalized tubes by strain engineering of nanomembranes on polymers", Advanced Materials, vol. 20, Issue 21, pp. 4085-4090.*
Manesh et al, "Template-Assisted Fabrication of Salt-Independent Catalytic Tubular Microengines", American Chemical Society, vol. 4, No. 4, pp. 1799-1804, 2010.*
Solovev et al, "Light-Controlled Propolusion of Catalytic MIcroenginines", Angewandte. Chem. Int. Ed., 2011, vol. 50, pp. 10875-10878.*
Gibbs et al, "Catalytic nanomotors: fabrication, mechanism and applications", Front. Mater. Sci., 2011, vol. 5, Issue 1, pp. 25-39.*
Solovev, "Catalytic Tubular Micro-Jet Engines", Technische Universitat Chemnitz, Mar. 29, 2012.*
Campuzano, S. et al. "Bacterial Isolation by Lectin-Modified Microengines," Nano Letters, 2012, 6 pages.
Campuzano, S. et al. "Bacterial Isolation by Lectin-Modified Microengines—Supporting Information," No dates provided, 6 pages.
Campuzano, S. et al. "Motion-driven Sensing and Biosensing using Electrochemically-Propelled Nanomotors." Analyst, 2011, 136, pp. 4621-4630.
Orozco, J. et al. "Dynamic Isolation and Unloading of Target Proteins by Aptamer-Modified Microtransporters," Analytical Chemistry, 2011, pp. 7962-7969.
Orozco, J. et al. "Dynamic Isolation and Unloading of Target Proteins by Aptamer-Modified Microtransporters Supporting Information," No dates provided, 3 pages.
Kagan, D. et al. "Functionalized Micromachines for Selective and Rapid Isolation of Nucleic Acid Targets from Complex Samples," Nano Letters. 2011, pp. 2083-2087.
Kagan, D. et al. "Functionalized Micromachines for Selective and Rapid Isolation of Nucleic Acid Targets from Complex Samples—Supporting Information," No dates provided, 14 pages.
Balasubramanian, S. et al. "Micromachine-enabled capture and isolation of cancer cells in complex media."Angewandte Chem. Int. Ed. 2011, pp. 4161-4164.
Balasubramanian, S. et al. "Micromachine-enabled capture and isolation of cancer cells in complex media—Supporting Information,". No dates provided, 10 pages.
Mei, Yongfeng et al. "Versatile Approach for integrative and Functionalized tubes by Strain Engineering of Nanomembranes on Polymers", Advance Materials, 2008, 20, pp. 4085-4090.
Solovev, Alexander A. et al., "Magnetic Control of Tubular Catalytic Microbots for the Transport, Assembly, and Delivery of Micro-objects", Adv. Funct. Mater. 2010, 20, pp. 2430-2435.
Paxton, Walter F. et al., "Motility of Catalytic Nanoparticles through Self-Generated Forces", Chem. Eur. J. 2005, 11, pp. 6462-6470.
Mirkovic, Tihana et al., "Fuel for Thought: Chemically Powered Nanomotors Out-Swim Nature's Flagellated Bacteria", ACS Nano, Apr. 27, 2010, pp. 782-1789.
Wang, Joseph, "Can Man-Made Nanomachines Compete with Nature Biomotors?", ACS Nano, Jan. 27, 2009, pp. 4-9.
Mallouk, Thomas E. et al., "Powering Nanorobots", Scientific American, May 2009, pp. 72-77.
Solovev, Alexander A. et al., "Catalytic Microtubular Jet Engines Self-Propelled by Accumulated bas Bubbles**"", 2009, pp. 1688-1692.
Wang, Joseph et al., "Motion Control at the Nanoscale", 2010, pp. 338-345.
Paxton, Walter F. et al., "Chemical Locomotion", Angew. Chem. Int. Ed. , 2006, pp. 5420-5429.
Ebbens, Stephen J. et al., "In pursuit of propulsion at the nanoscale", Soft Matter, 2010, pp. 726-738.
Kagan, Daniel et al., "Rapid Delivery of Drug Carriers Propelled and Navigated by Catalytic Nanoshuttles", 2010, pp. 2741-2747.
Wu, Jie et al., "Motion-based DNA detection using catalytic nanomotors", Nature Communications, Jul. 13, 2010, pp. 1-6.
Sundararajan, Shakuntala et al., "Catalytic Motors for Transport of Colloidal Cargo", Nano Lett., 2008, pp. 1271-1276.
Burdick, Jared et al., "Synthetic Nanomotors in Microchannel Networks: Directional Microchip Motion and Controlled Manipulation of Cargo", J. Am. Chem. Soc, 2008, 130, pp. 8164-8165.

(56) References Cited

OTHER PUBLICATIONS

Sundararajan, Shakuntala et al., "Drop-Off of Colloidal Cargo Transported by Catalytic Pt-Au Nanomotors via Photochemical Stimuli**", 2010, 6, No. 14, pp. 1479-1482.
Manesh, et al., "Template-Assisted Fabrication of Salt-Independent Catalytic Tubular Microengines", ACS Nano, 4, vol. 4, No. 4, Mar. 15, 2010, pp. 1799-1804.
Shi, Zuo-Rong et al., "Monoclonal Antibody Col-1 Reacts with Restricted Epitopes on Carcinoembryonic Antigen: An Immunohistochemical Study", The Journal of Histochemistry and Cytochemistry, vol. 42, No. 9, 1994, pp. 1215-1219.
Zieglschmid, V. et al., "Detection of Disseminated Tumor Cells in Peripheral Blood", Critical Reviews in Clinical laboratory Sciences, 42(02), 2005, pp. 155-196.
Zhang, Li et al, "Characterizing the Swimming Properties of Artificial Bacterial Flagella", Nano Letters, vol. 9, No. 10, 2009, pp. 3663-3667.
Plouffe, Brian D. et al., "Development of microfluidics as endothelial progenitor cell capture technology for cardiovascular tissue engineering and diagnostic medicine", the FASEB Journal, vol., 23, No. 10, Nov., 2016, pp. 3309-3314.
Adams, André A. et al., "Highly Efficient Circulating Tumor Cell Isolation from Whole Blood and Label-Free Enumeration Using Polymer-Based Microfluidics with an Integrated Conductivity Sensor", J. Am. Chem. Soc., 2008, 130, pp. 8633-8641.
Allan, Alison L. et al., "Circulating Tumor Cell Analysis: Technical and statistical Considerations for Application to the Clinic", Journal of Oncology, vol. 2010, Article ID 426218, 10 pages.
Bachand, George D. et al., "Smart dust biosensors powered by biomolecular motors", Lab Chip, 2009, 9, pp. 1661-1666.
Galanzha, Ekaterina I. et al., "In Vivo magnetic enrichment and multiplex photoacoustic detection of circulating turmour cells", Nature Nanotechnology, vol. 4, Dec. 2009, www.nature.com/naturenanotechnology, pp. 855-860.
Nagrath, Sunitha et al., "Isolation of rare circulating tumour cells in cancer patients by microchip technology", Nature, vol. 450, Dec. 20/27, 2007, 7 pages.
Taira, Shu et al., "Selective Detection and Transport of Fully Matched DNA by DNA-Loaded Microtubule and Kinesin Motor Protein", Biotechnology and Bioengineering, vol. 95, No. 3, Oct. 20, 2006, pp. 533-538.
Taira, Shu et al. "Loading and Unloading of Molecular Cargo by DNA-Conjugated Microtubule", Biotechnology and Bioengineering, vol. 99, No. 3, Feb. 15, 2008, pp. 734-739.
Laocharoensuk, Rawiwan et al., "Carbon-Nanotube-Induced Acceleration of Catalytic Nanomotors", www.acsnano.org, vol. 2, No. 5, 2008, pp. 1069-1075.
Demirok, U. Korcan et al., "Ultrafast Catalytic Alloy Nanomotors**", Angew. Chem. Int. Ed. 2008, 47, pp. 9349-9351.
Balasubramanian, Shankar et al., "Thermal Modulation of Nanomotor Movement", 2009, 5, No. 13, pp. 1569-1574.
Calvo-Marzal, Percy et al., "Electrochemically-triggered motion of catalytic nanomotors", Chem. Commun., 2009, pp. 4509-4511.
Kagan, Daniel et al., "Chemical Sensing Based on Catalytic Nanomotors: Motion-Based Detection of Trace Silver", J. Am. Chem. Soc., 2009, 131, pp. 12082-12083.
Manesh, Kalayil Manian et al., "Nanomotor-based 'writing' of surface microstructures", Chem. Commun., 2010, 46, pp. 5704-5706.
Sattayasamitsathit, Sirilak et al., Simplified Cost-Effective Preparation of High-Performance Ag-Pt Nanowire Motors, ChemPhysChem 2010, 11, pp. 2902-2805.
Gao, Wei et al., "Magnetically Powered Flexible Metal Nanowire Motors", J. Am. Chem. Soc., vol. 132, No. 41, 2010, pp. 14403-14405.
Kagan, Daniel et al., "Chemically Triggered Swarming of Gold Microparticles**", Angew. Chem. Int. Ed. 2011, 50, pp. 503-506.
Wang, Joseph, "Motion-based detection of nucleic acids using nanomotors", Nature Protocol Exchange, 2010, 8 pages.
Gao, Wei et al., "Hybrid Nanomotor: A Catalytically/Magetically Powered Adaptive Nanowire Swimmer", 2011, 7, No. 14, pp. 2047-2051.
Pak, On Shun et al., "High-speed propulsion of flexible nanowire motors: Theory and experiments", Soft Matter, 2011, 7, pp. 8169-8181.
Gao, Wei et al., "Highly Efficient Catalytic Microengines: Template Electrosynthesis of Polyaniline/Platinum Microtubes", J. Am. Chem. Soc. 2011, 133, pp. 11862-11864.
Gao, Wei et al., "Cargo-Towing Fuel-Free Magnetic Nanoswimmers for Targeted Drug Delivery", 2012, 8, No. 3, pp. 460-467.
Gao, Wei et al., "Catalytically Propelled Micro-/Nanomotors: How Fast Can They Move?", The Chemical Record, vol. 12, 2012, pp. 224-231.
Gao, Wei et al., "Hydrogen-Bubble-Propelled Zinc-Based Microrockets in Strongly Acidic Media", J. Am. ChemSoc. 2012, 134, pp. 897-900.
Hiyama, Satoshi et al., "Autonomous Loading, Transporting, and Unloading of Specified Cargoes by Using DNA Hybridization and Biological Motor-Based Motility**", 2008, 4, No. 4, pp. 410-415.
Calvo-Marzal, Percy et al., "Propulsion of nanowire diodes", Chem. Commun., 2010, 46, pp. 1623-1624.
Levicky, R. et al., "Using Self-Assembly to Control the Structure of DNA Monolayers on Gold: A Neutron Reflectivity Study", J. Am. Chem. Soc. 1998, vol. 120, pp. 9787-9792.
Liao, J. C. et al., "Use of Electrochemical DNA Biosensors for Rapid Molecular Identification of Uropathogens in clinical Urine Specimens", J. Clin. Microbic!. 2006, vol. 44, pp. 561-570.
Wu, J.; et al., "Potentiometric Detection of DNA Hybridization using Enzyme-Induced Metallization and a Silver Ion Selective Electrode", Anal. Chem. 2009, vol. 81, pp. 10007-10012.
Wu, J. et al., "Ternary Surface Momolayers for Ultrasensitive (Zeptomole) Amperometric Detection of Nucleic Acid Hybridization without Signal Amplification", Anal. Chem. 2010, vol. 82, pp. 8830-8837.
International Search Report and Written Opinion for PCT Application No. PCT/US2012/023410; dated Sep. 21, 2012; 9 pgs.

\* cited by examiner

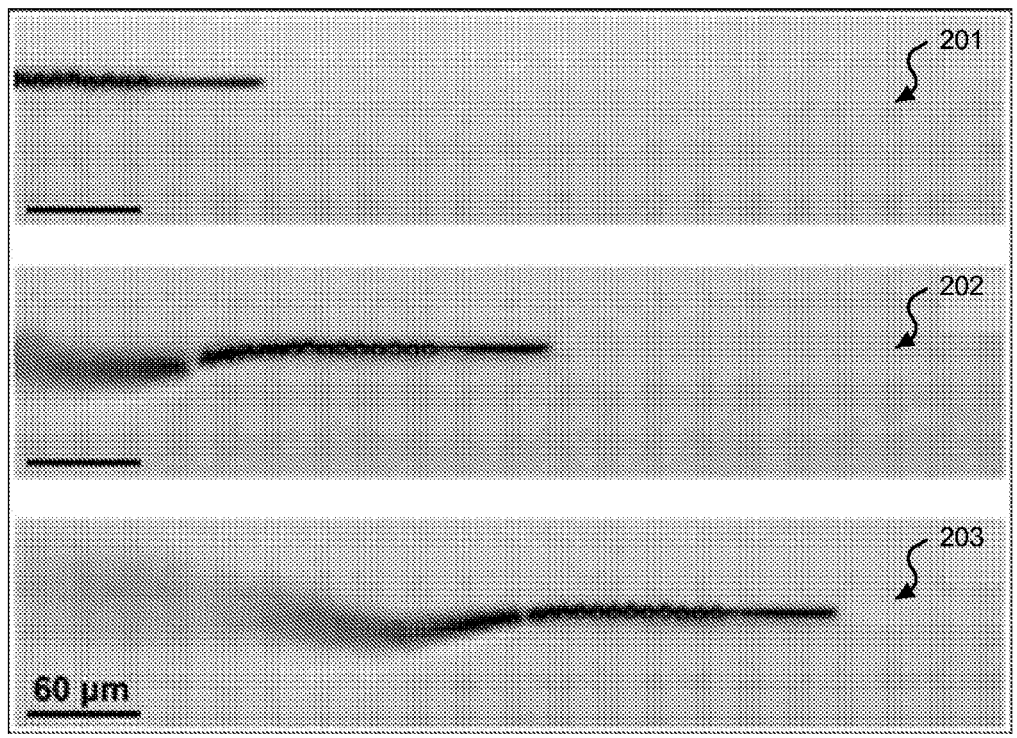
FIG. 2
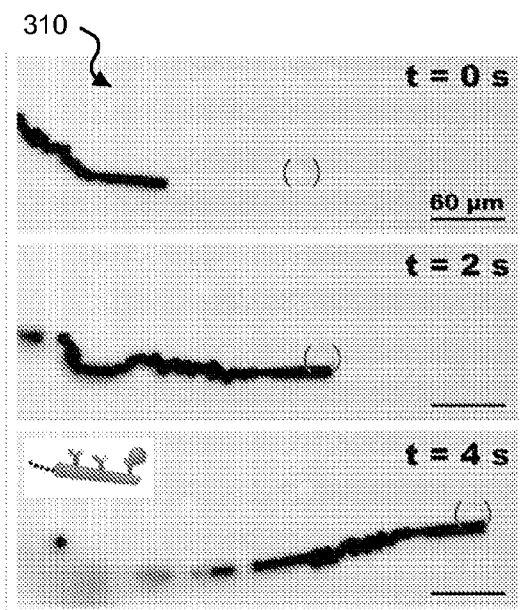 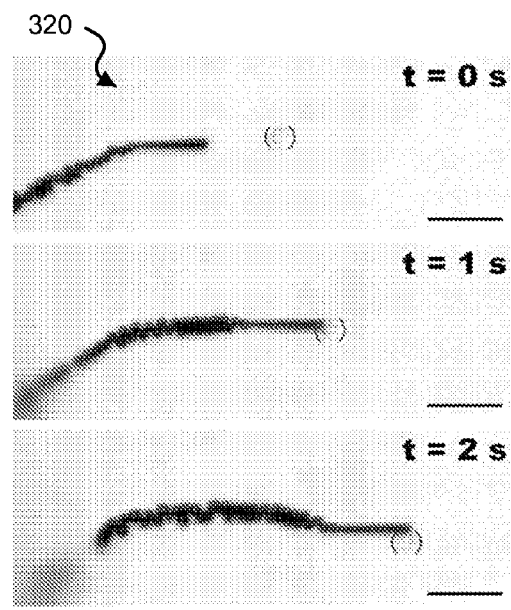
FIG. 3A  FIG. 3B

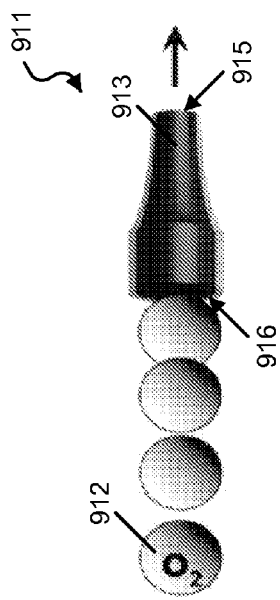
FIG. 9A
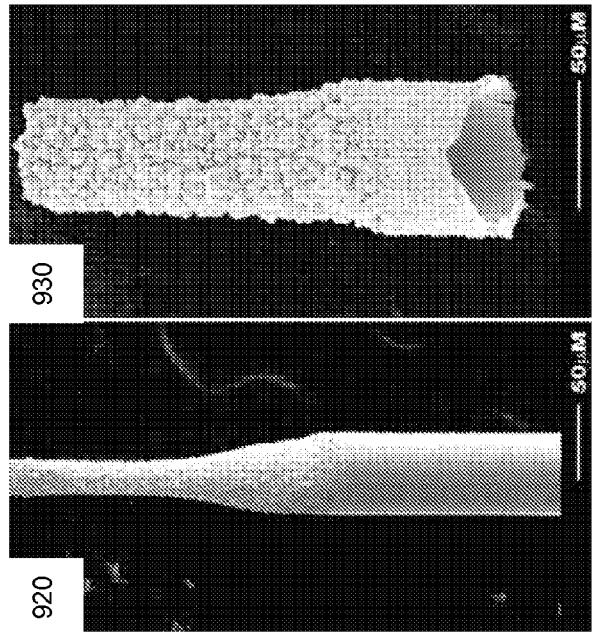
FIG. 9B
FIG. 9C
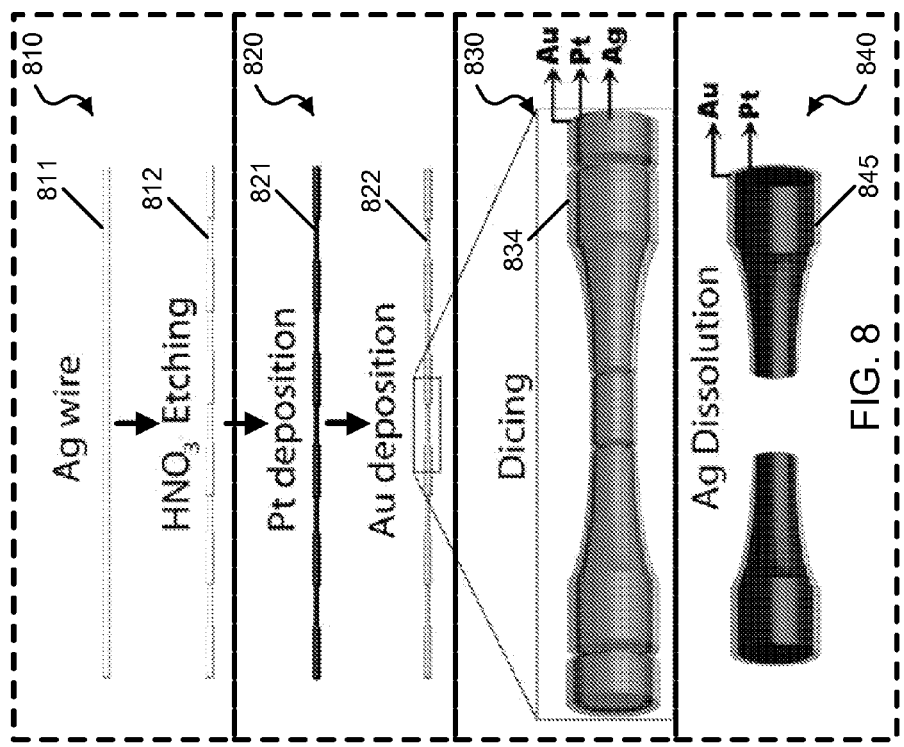
FIG. 8

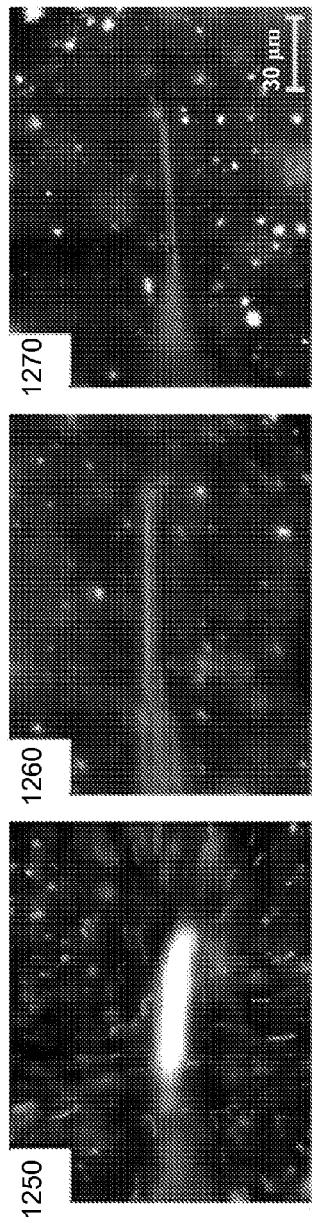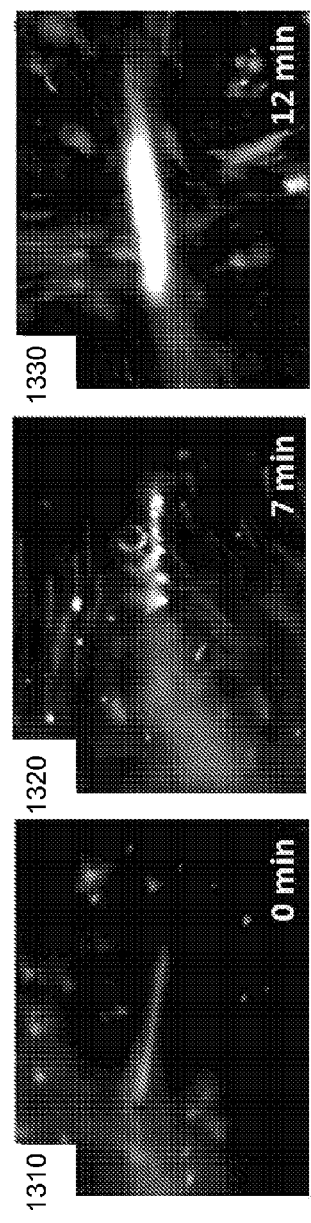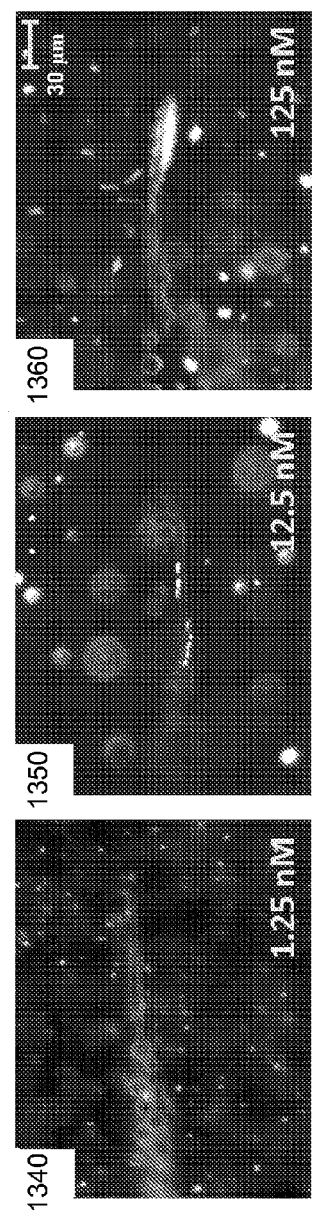
FIG. 12
FIG. 13

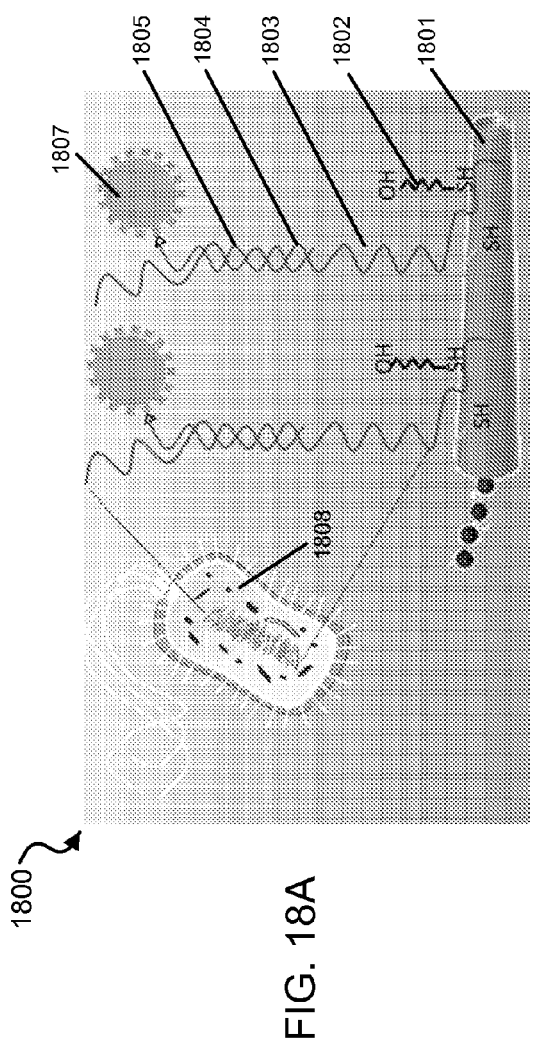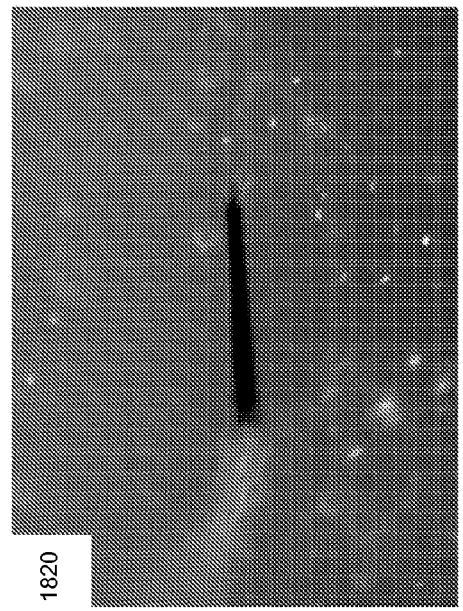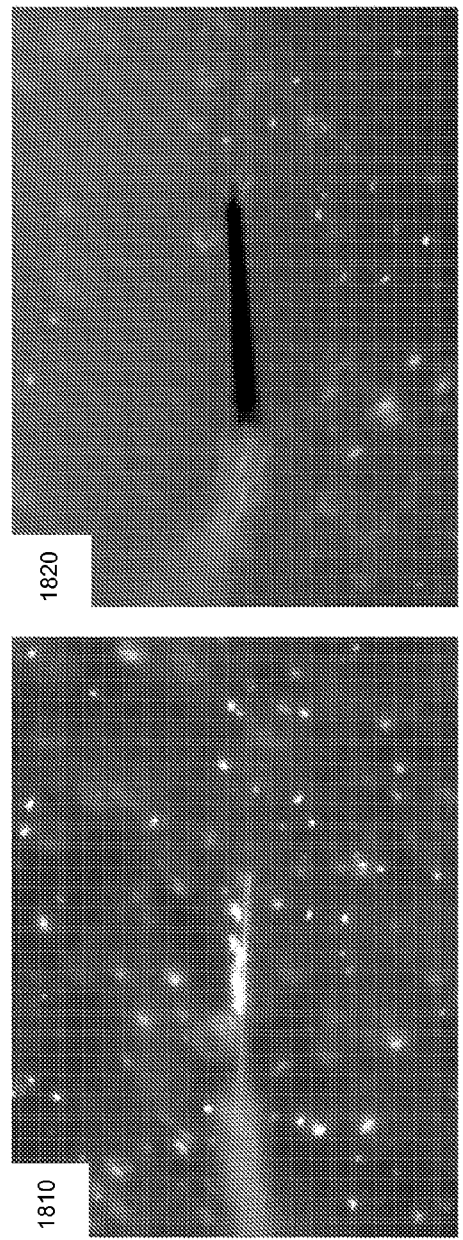
FIG. 18A
FIG. 18B
FIG. 18C

NANO/MICROSCALE VEHICLES FOR CAPTURE AND ISOLATION OF TARGET BIOMOLECULES AND LIVING ORGANISMS

CROSS-REFERENCE TO RELATED APPLICATIONS

This patent document is a 35 USC § 371 National Stage application of International Application No. PCT/US2012/023410 filed Jan. 31, 2012, which claims priority of U.S. Provisional Patent Application No. 61/438,233, entitled "NANO/MICROSCALE MOTORS AND ISOLATION OF TARGET BIOMOLECULES FROM COMPLEX SAMPLES" and filed Jan. 31, 2011; the entire disclosures of which are incorporated herein by reference for all purposes.

STATEMENT REGARDING FEDERALLY SPONSORED RESEARCH OR DEVELOPMENT

This invention was made with government support under grant/contract CBET 0853375 awarded by the National Science Foundation (NSF). The government has certain rights in the invention.

BACKGROUND

This patent document relates to systems, devices, and processes that use micro/nanoscale structures.

Separation and isolation of biomolecules can involve expensive equipment and tedious processes. For example, microfluidic chips are microscale devices that can be used to separate and/or isolate molecules from a flowing fluid involving manipulation of fluids within networks of channels, e.g., in a solid substrate. Microfluidic devices have been used in a variety of point-of-care (POC) devices to implement various tests in many clinical applications. Bioanalysis techniques using microfluidic devices can include microscale valves and pumps, e.g., to provide more precise metering of fluids. For example, the valves can be controlled by peripheral pumps that can cause bottlenecks of the fluid sample in the microfluidic device, e.g., limiting its effective uses in many POC diagnostics.

SUMMARY

Techniques, systems, devices and materials are described for implementing functionalized micro- and nano-scale structures for capturing and/or isolating targeted biomolecules and living organisms.

In one aspect of the disclosed technology, a device that self propels in a fuel fluid includes a tube structured to include a first large opening and a second small opening that are on opposite ends of the tube, and a tube body connecting the first and second openings and having a cross section spatially reducing in size along a longitudinal direction from the first large opening to the second small opening, in which the tube includes a layered wall which includes an inner layer having a catalyst material that is reactive with a fuel fluid to produce bubbles exiting the tube from the first large opening to propel the tube to move in the fuel fluid and an external layer formed of a material capable of being functionalized, and a molecular layer functionalized onto the external layer of the tube and structured to attach to a targeted molecule in the fuel fluid.

In another aspect, a device for transporting a target substance in a fluid includes a tube formed of two or more layers with a first opening having a smaller diameter than a second opening of the tube, in which the two or more layers include an outer layer having a modifiable material capable of being functionalized, and a molecular layer formed on the modifiable material and including a ligand molecule, in which the molecular layer is structured to attach a target substance having a receptor site with a binding affinity to the ligand molecule, in which the two or more layers include an inner layer including a catalytic material that reacts with a fuel in a fluid to produce bubbles exiting the tube from the second opening to propel the tube to move in the fluid, the tube attaching the target substance during movement at a first location in the fluid and transporting the target substance to a second location in the fluid.

In another aspect, a method of using a tube to collect a target substance in a fluid, includes providing a catalyst material that is reactive to a fuel fluid on an inner wall of a tube to generate bubbles that propel the tube in the fuel fluid, and using a molecular layer on the external surface of the tube to selectively collect a target substance in the fuel fluid.

The subject matter described in this patent document can be implemented in specific ways that provide one or more of the following features. For example, the described functionalized nano/microscale motors can establish effective contact and capture of target biomolecules and cells, e.g., by functionalized surfaces of the micro/nanostructures having non-complex geometries. For example, the functionalized surfaces of the micro/nanostructures can include ligand molecules, e.g., single-stranded nucleic acid-based oligonucleotides, aptamers, antibodies, peptides, glycoproteins, other protein-based molecules, and other biomolecules. The described nano/microscale motors can be programmed to scower an entire static sample as many times as needed. Further, the movement of the disclosed nano/microscale motor can increase the solution convection and improve the diffusion of a target biomolecule, e.g., enabling a faster, more favorable recognition reaction. Nano/micromotors of the disclosed technology can provide biomolecule isolation in a clean environment and be utilized in many versatile implementations (e.g., the possibility of parallel/multiplexed capture and transport). For example, the disclosed nano/micromotors can reduce non-specific binding of a target biomolecule as it travels, e.g., to a clean environment for post-capture analysis. Exemplary nano/microscale motors can provide advantages of high speed and capture efficiency, low cost, and small sample volume requirements in a variety of biomedical and clinically relevant applications. For example, the ability to selectively isolate individual cancer cells using the exemplary nano/microscale motors can be utilized in many bioanalytical techniques and microchip devices, e.g., including food safety, biothreat detection, forensic analysis, and early stage tumor cell detection towards that can be utilized in cancer diagnostics applications.

BRIEF DESCRIPTION OF THE DRAWINGS

FIG. 2 shows time lapse images of exemplary antibody-functionalized microrocket motion in human serum in human serum.

FIGS. 3A and 3B show exemplary time lapse images of functionalized microrocket motion in buffer and in human serum.

FIG. 8 shows a schematic illustration of an exemplary template-assisted technique to fabricate tubular microrockets.

FIG. 9A shows a schematic illustration of an exemplary tubular microrocket.

FIGS. 9B and 9C show scanning electron microscopy (SEM) images of an exemplary silver wire and gold-platinum microrocket.

FIG. 12 shows optical images demonstrating the motion-based target hybridization and isolation by exemplary nucleic acid-functionalized microrockets.

FIG. 13 shows optical images demonstrating the influence of hybridization time and target concentration on the uptake of exemplary fluorescent-tagged target DNA.

FIG. 18A shows a schematic illustration of an exemplary functionalized microrocket for capture and isolation of bacterial rRNA.

FIGS. 18B and 18C show exemplary time lapse images demonstrating SHCP+MCH-modified microrocket propulsion in lysate fluid samples.

Like reference symbols and designations in the various drawings indicate like elements.

DETAILED DESCRIPTION

Figure 1:
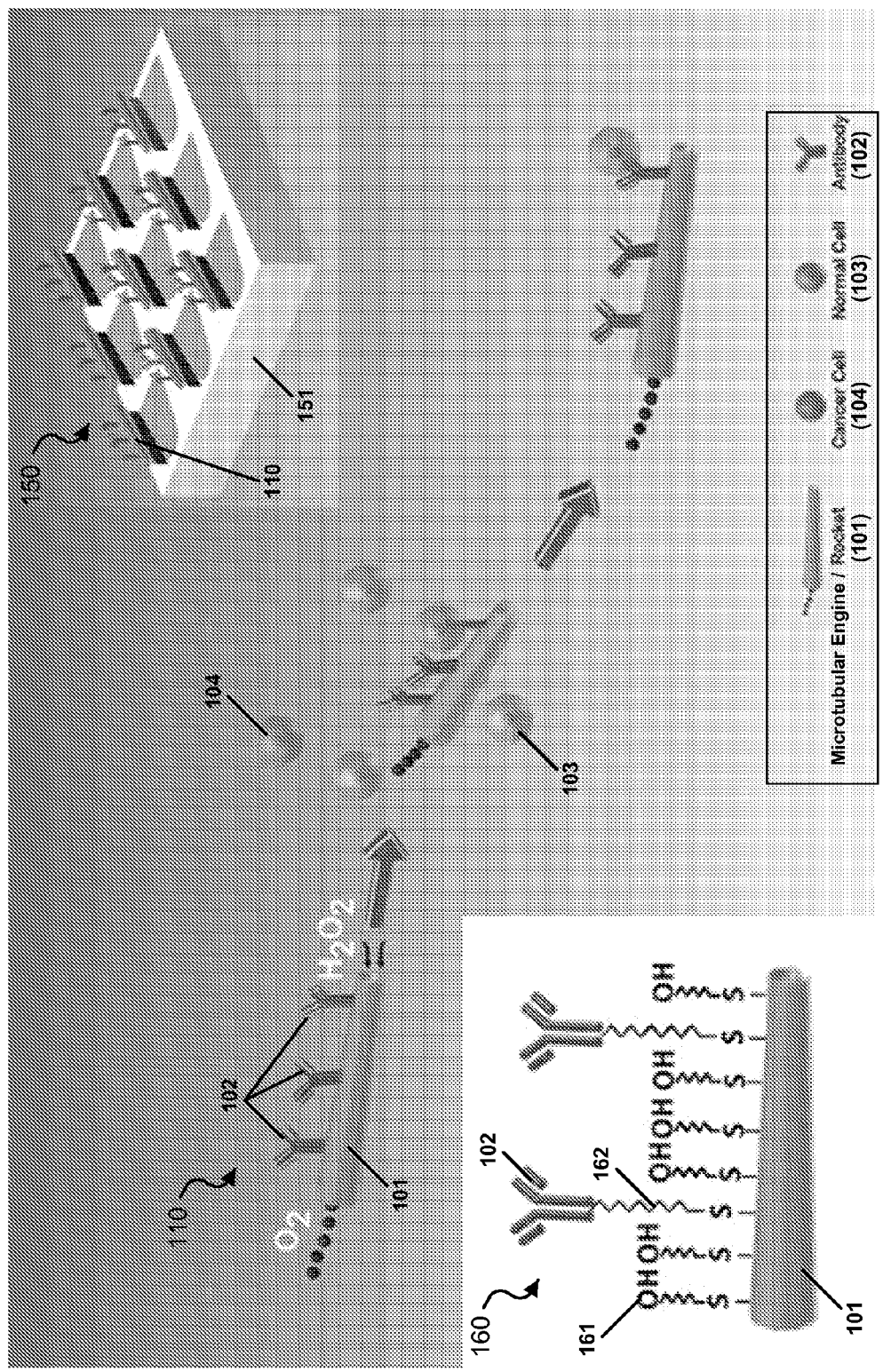
FIG. 1 shows exemplary schematic illustrations of the disclosed microrockets for capture and isolation of target cancer cells.

The techniques, systems, devices and materials are described for implementing functionalized micro- and nanoscale structures for capturing, isolating, and/or transporting targeted biomolecules and living organisms in a fluid.

For example, the nano/microstructures of the disclosed technology are capable of autonomous movement and provide capabilities, e.g., including pick-up and transport of targeted payloads. The disclosed engineered microstructures are also referred to in this patent document as microtube rockets or microrockets, microtube engines or microengines, microtube motors or micromotors, micromachines, microtubes, and microcones. The disclosed engineered nanostructures are also referred to in this patent document as nanotube rockets or nanorockets, nanotube engines or nanoengines, nanotube motors or nanomotors, nanomachines, nanotubes, and nanocones. In some examples, the nano/micromotors of the disclosed technology can be engineered as immuno-nano/micromachines that can isolate cells and/or target molecules from complex samples in vitro in a variety of biomedical applications, e.g., including drug delivery to biosensing. In some examples, chemically-powered nanomotors and micromotors can be configured to move and pick-up/transport payloads in physiological conditions, e.g., within environments having high ionic strength, such as biological fluids.

For example, target biomolecules can include nucleic acids, lipids, carbohydrates, peptides, proteins, enzymes, hormones, antibodies, glycoproteins, glycolipids, organelles, endotoxins, viruses, and other biological materials and biomarkers. Exemplary living organisms can include cells, e.g., healthy cells, cancer cells, bacterial cells, and other types of cells. Exemplary fluids can include biological fluids, such as (but not limited to, for example, such as (but not limited to) aqueous humour and vitreous humour, bile, blood (e.g., blood serum, blood plasma), cerebrospinal fluid, intracellular fluid (e.g., cytoplasm) and extracellular fluid (including interstitial fluid, transcellular fluid, plasma), digestive fluid (including gastric juice and intestinal juice), lymphatic fluid and endolymph and perilymph, mucus (including nasal drainage and phlegm), peritoneal fluid, pleural fluid, saliva, sebum (e.g., skin oil), semen, sweat, tears, urine, vaginal fluids, and bacterial lysates. Other exemplary fluids can include non-biological fluids, such as (but not limited to), for example, pure water, salt-containing water, sugar-containing water, juice, and oil-based fluids.

In one aspect, the disclosed technology can include catalytic, rolled-up nano/microtube rockets that are propelled by the recoiling force of accumulated gas bubbles. These exemplary microrockets provide the capability to target, capture, isolate and transport molecules and cells, e.g., which can also enable downstream analysis.

The ability to capture and study circulating tumor cells (CTC) can have implications, for example, in early detection, diagnosis, determining prognosis and monitoring of cancer, as well as for understanding the fundamental biology of metastasis. The exemplary microrockets of the disclosed technology can be implemented for in-vitro capture and/or isolation of circulating tumor cells in a static or stationary fluid. For example, the disclosed microrockets can be functionalized with a ligand molecule (e.g., an antibody) that can enable the capture of a targeted CTC having a receptor molecule (e.g., an antigen), in which an affinity exists between the ligand molecule and receptor molecule. For example, antibody-functionalized microengine rockets can enable the capture of a target CTC based on a selective binding ability of attached antibody to the specific targeted antigens of the CTC. The disclosed functionalized microrockets can capture a target CTC during self-propelled locomotion in a fluid, e.g., a static complex biological fluid. For example, a fuel-driven bubble propulsion mechanism can enable autonomous movement of the microrocket. The exemplary functionalities of autonomous movement and cell capture and towing can enable effective cell capture and transport of cells, e.g., cancer cells in serum.

Exemplary implementations were performed to demonstrate the described functionalities and capabilities of the disclosed antibody-functionalized microrocket technology. For example, the capture and transport properties of antibody-modified microrockets were shown to be highly specific to target cancer cells having the corresponding antigens.

Exemplary microrockets were functionalized with an antibody specific for antigenic surface proteins expressed on particular cancer cells. For example, an anti-carcinoembryonic antigen (anti-CEA) monoclonal antibody (mAb) can be attached to the modified surface of an exemplary microrocket to form an anti-CEA mAb-functionalized microrocket. Exemplary anti-CEA mAb-functionalized microrockets were utilized in exemplary implementations for capture and isolation of cells expressing the carcinoembryonic antigen (CEA). CEA is a glycoprotein involved in cell adhesion, which is typically produced during fetal development and stops production before birth. For example, CEA is not usually present in the blood of healthy adults, but can be found in cancer cells. CEA can be considered one of the most common antigens among cancer cells, being over-expressed in approximately 95% of colorectal, gastric and pancreatic cancers. Cells having CEA are denoted as CEA+, and cells not expressing CEA are denoted as CEA−.

FIG. 1 shows exemplary schematic illustrations of the disclosed microrockets for capture and isolation of target cancer cells. For example, an anti-CEA mAb-modified microrocket 110 can be functionalized to include anti-CEA monoclonal antibodies 102 on a microtubular engine 101. For example, the microtubular engine 101 can include Au-coated Ti—Fe—Au—Pt microtube engines, Au-coated Ti—Ni—Au—Pt microtube engines, bimetal microtube engines (e.g., Au—Pt microtube engines), or Au-coated polymer-platinum microtube engines (e.g., a polyaniline (PANI) polymer in Au-PANI-Pt, Au—Fe-PANI-Pt, and Au—Ni-PANI-Pt microtubular engines), as well as other configurations. The microtubular engine 101 can include an inner metallic layer (e.g., Pt) that can catalyze a fuel and generate propulsion. The microtubular engine 101 can also include an exterior metallic layer (e.g., Au) that can facilitate the functionalization of antibodies such as the anti-CEA monoclonal antibodies 102, e.g., by surface chemistry modification techniques.

As shown in FIG. 1, the exemplary anti-CEA mAb-modified microrocket 110 can autonomously move by facilitating the entrance of a fuel (e.g., hydrogen peroxide ($H_2O_2$)) through the small radial opening of the microtubular engine 101. Catalytically-generated gas bubbles (e.g., oxygen microbubbles ($O_2$)) can be formed and travel along a sloped transition of the inner surface of the microtubular engine 101. The oxygen microbubbles can be ejected out from the larger radial opening of the microtubular engine 101, e.g., which generates the force propelling the anti-CEA mAb-modified microrocket 110 in the fluid. For example, the fluid shown in FIG. 1 can be a biological sample, e.g., blood, serum, urine, etc. The exemplary antibody-modified microrocket 110 can capture and transport at least one cancer cell 104 among multitudes of other cells, e.g., normal cells 103. For example, upon encountering target cancer cells 104 in the biological fluid, the confined antibodies 102 recognize the CEA surface antigens over-expressed on the target cancer cells 104. Recognition of the CEA surface antigens by the anti-CEA monoclonal antibodies 102 can allow selective pick-up and transport of the cancer cell(s) 104 by the anti-CEA mAb-modified microrocket 110 over a preselected path. As shown in the illustration, these exemplary antibody-modified microrockets continue to exhibit efficient locomotion and a large towing force.

The top-right inset in FIG. 1 shows a schematic 150 illustrating the fabrication/preparation of the anti-CEA mAb-modified microrocket 110 on a substrate 151. The bottom-left inset in FIG. 1 shows a schematic 160 illustrating the surface chemistry used for the functionalization of the anti-CEA mAb-modified microrocket 110. Schematic 160 shows the microtubular engine 101 modified with a self-assembled alkanethiol monolayer 161 and an antibody-hosting self-assembled alkanethiol monolayer 162, e.g., which attaches the anti-CEA monoclonal antibodies 102. For example, conjugation of the anti-CEA mAb antibodies to the outer gold surface of the microtubular engine can be accomplished through carboxyl-terminated groups of the antibody-hosting self-assembled alkanethiol monolayer 162 of the binary self-assembled monolayer (SAM) using exemplary EDC/NHS chemistry. Exemplary fabrication and surface modification techniques are described in further detail later in this patent document.

For example, the disclosed functionalized microrocket (e.g., antibody-modified microrocket 110 or other attached ligands to a modified nano-sized or micro-sized structures such as microtubular engine 101) can be a device that self propels in a fuel fluid. For example, the device can include a tube structured to include a large opening and a smaller opening that are on opposite ends of the tube. The exemplary tube body connects the first and second openings and can have a cross section that spatially reduces in size along a longitudinal direction from the large opening to the small opening. The exemplary tube includes a layered wall that includes an inner layer having a catalyst material. The exemplary catalyst material can be reactive with a fuel fluid (e.g., a fuel within a fluid that can include water, salt-containing water, oil-based liquid, biological fluids, etc.) to produce bubbles exiting the tube from the large opening. The exemplary produced bubbles (e.g., microbubbles) can propel the tube to move in the fuel fluid. The tube can also include an external layer formed of a material capable of being functionalized, e.g., gold or silver. The device can also include a molecular layer (e.g., a binary SAM layer formed by SAM 161 and SAM 162 that can attach a ligand molecule, for example, an antibody 102) that is functionalized onto the external layer of the tube and structured to attach to a targeted molecule in the fuel fluid. The target molecule can be a nucleic acid, protein, or receptor on a living cell, among other substances.

The effective motor propulsion can be maintained in relevant physiological fluids, e.g., in a variety cancer cell sorting applications. For example, FIG. 2 shows exemplary images 201, 202, and 203 demonstrating the movement of an mAb-coated microrocket in human serum. These exemplary images 201, 202, and 203 show a long tail of microbubbles (e.g., ~7.2 μm radius), which are catalytically generated on the inner platinum surface and released from the rear of the microtube, e.g., at a rate of 14 bubbles/sec. In this exemplary implementation, the human serum was diluted 1:4 to include the microrockets and hydrogen peroxide fuel. The exemplary conditions of the diluted human serum included a 7.5% (w/v) $H_2O_2$ and 1% (w/v) sodium cholate. For example, the ejections of the microbubbles propels the microrocket in the diluted serum medium at a high speed, e.g., ~85 μm/s. In some examples, a sandwiched ferromagnetic (Fe) layer of the microrocket can offers convenient guidance of the rocket via tuning of the external magnetic-field direction. In this example, thickness of the Fe layer can be further increased (e.g., three times the initial layer thickness) to facilitate more effective propulsion and navigation in such biological media.

FIGS. 3A and 3B show time lapse images 310 and 320 of exemplary functionalized microrocket motion in buffer and in human serum, respectively. The exemplary mAb-functionalized microrockets shown in images 310 and 320 can selectively bind to target cancer cells and then effectively transport them in the fluid. As shown in FIG. 3A, the time lapse images 310 demonstrate pick-up and transport of a CEA+ pancreatic cancer cell by an anti-CEA mAb-modified microrocket in phosphate buffer saline (PBS) at 2 second intervals. Conditions of this exemplary implementation included 1×PBS buffer (pH 7.4) containing 7.5% (w/v) $H_2O_2$ and 1% (w/v) sodium cholate. The exemplary CEA+ cells shown in time lapse images 310 are accented using blue circles/parentheses.

As shown in FIG. 3B, the time lapse images 320 demonstrate pick-up and transport of a CEA+ pancreatic cancer cell by an anti-CEA mAb-modified microrocket in human at 1 second intervals. Conditions of this exemplary implementation included human serum containing 7.5% (w/v) $H_2O_2$ and 1% (w/v) sodium cholate. The exemplary CEA+ cells shown in time lapse images 320 are accented using blue circles/parentheses. The top time lapse image (in both images 310 and 320) at t=0 sec shows the movement of the exemplary microrocket towards the CEA+ cell. The middle time lapse image (at t=2 sec in images 310 and at t=1 sec in 320) shows the dynamic 'en route' capture of the cell. The bottom time lapse image (at t=4 sec in images 310 and at t=2 sec in 320) shows the subsequent directed travel of the cancer-cell loaded micromotor over a pre-selected path, e.g., without compromising the trajectory of the rocket movement. The speed of the microrocket was determined to be 85 μm/s in the serum environment (FIG. 3B) before cell loading and 80 μm/s after cell loading.

A substantial force can be essential for transporting a relatively large cancer cell (e.g., ~16 μm diameter cell). The disclosed antibody-modified microrockets can exhibit a bubble recoiling propulsion mechanism capable of capturing and transporting such cells. For example, this can be shown by estimations of a velocity-dependent drag force of the microrockets, e.g., using Stokes' Law. For example, using Stokes' law in Equation (1), the force necessary to counter a drag force ($F_d$) that a cell may experience at a constant velocity of one body length per second in the working solution can be determined by:

$$F_d = 6\pi\mu r v \qquad (1)$$

where μ is the solution viscosity, r is the cell radius and v is the linear velocity of the cell (e.g., 16 μm/s). Calculations using these exemplary values reveal that the following forces may be needed to carry a large cell at a reasonable speed in the different media, as shown in Table 1. Table 1 includes data showing forces necessary to carry a 16 μm diameter cell in different media at 1 body-lengths. The asterisk (*) in Table 1 indicates that the viscosity values were taken at a room temperature of 20° C.

TABLE 1

| Medium | μ* (CP) | $F_d$, (pN) |
|---|---|---|
| Fuel solution containing 7.5% (w/v) $H_2O_2$ in 1 × PBS, 1% (w/v) sodium cholate | 1.05 | 2.5 |
| Fuel solution containing 7.5% (w/v) $H_2O_2$ in 25% (v/v) human serum, 1% (w/v) sodium cholate | 1.14 | 2.8 |
| Human blood | 5.0 | 12.1 |

Stokes' drag law for a cylinder can be used to determine the propulsive force of an exemplary microrocket, e.g., as shown in Equation (2). For example, it can be assumed that the rocket may experience drag as a solid cylinder (e.g., as the fluid cannot freely flow through the oxygen-bubble-containing rocket and negating the slight 2-4° angle along the rocket, e.g., approaching a cylindrical shape).

$$F_d = \frac{2\pi\mu L}{\ln\left(\frac{2L}{R}\right) - 0.72} v \qquad (2)$$

where R and L are the radius and the length of the microrockets (e.g., 2.5 and 60 μm, respectively).

For example, Table 1 shows a minimum force for transporting an exemplary large cell at 1 body-length/sec is 2.5 pN. For example, an unmodified microrocket can move at a high speed of up to 2 mm/s in PBS media and exerting an exemplary force up to 250 pN. However, after the surface modification with the antibody, the exemplary antibody-modified microrockets were shown to travel in the same bulk media at a speed of up to 150 μm/s and generate an force of ~18 pN. The exemplary antibody-modified microrockets exhibit more than sufficient speed and force capable of effectively transport large cells. It can be hypothesized that partial blocking may occur on Pt catalytic sites due to the surface chemistry modification to attach the antibody. This supposed phenomenon may account for this diminished speed.

The exemplary modified rockets can exert a sufficient force to transport large cells. In addition though, it can be advantageous that they do not apply a large shear force, e.g., which in some cases can prevent binding from occurring or disturb the viability of the captured cells. The shear stress ($\tau_s$) exerted as a result of microrocket interaction with the cell can be calculated based on the following Equation (3):

$$\tau_s = \frac{F_d}{A} \quad (3)$$

where A represents the interaction area. Exemplary values of the drag force applied by the anti-CEA mAb modified microrocket to the carried cell are summarized in Table 2. Table 2 includes data showing drag forces and shear stress applied to the carried cell as a function of the speed of the anti-CEA mAb modified microrocket in different working media. The asterisk (*) in Table 2 indicates movement of the anti-CEA mAb-modified microrocket was in the bottom plane.

TABLE 2

| Medium | v, μm/s | $F_d$, pN | $\tau_s$, dyn/cm$^2$ |
| --- | --- | --- | --- |
| Fuel solution containing 7.5% (w/v) H$_2$O$_2$ in 1 × PBS, 1% (w/v) sodium cholate | 150 | 18.1 | 2.3 |
| Fuel solution containing 7.5% (w/v) H$_2$O$_2$ in 25% (v/v) human serum, 1% (w/v) sodium cholate | 100 | 13.3 | 1.7 |
| Fuel solution containing 7.5% (w/v) H$_2$O$_2$ in 1 × PBS, 1% (w/v) sodium cholate* | 45 | 5.7 | 0.7 |

For example, the interaction area can be estimated as ⅔ of the average cell diameter for the width, and ½ of the rockets circumference as the height (7.85 μm). Exemplary estimates can be based on visual observations that show a slight cell deformation around the microrocket as it passes. For example, the average contact area can be 78.5 pm$^2$, and the shear stress can be considered directly proportional to the force and ultimately to the rocket speed. The lower shear stress (0.7 dyn/cm$^2$) induced by the anti-CEA mAb modified microrocket in the control experiments can ensure an increase in binding affinity between the anti-CEA mAb modified rocket and the CEA on the cell surface during pick-up. For example, once a cancer cell is captured by a anti-CEA mAb modified rocket, the interaction is strong enough for retaining the cell upon experiencing larger shear stresses.

For example, in the presence of diluted serum, the microrocket speed in the bulk solution was shown to drop to ~100 μm/s, e.g., which can reflect the increased solution viscosity. Even at the exemplary lower speed of ~100 μm/s, the exemplary microrockets demonstrate sufficient force (e.g., >13 pN) to overcome the additional drag force due to the capture of a cancer cell and transport of the cell over long periods (e.g., >60 s). In some examples, lower microrocket speed can be advantageous for the cell capture and transport, as it can reduce shear stress and allow for sufficient antigen/antibody interaction. For example, the upper limit of the rocket speeds in PBS and serum included shear stresses of 2.3 and 1.7 dyn/cm$^2$, respectively, as shown in Table 2.

Other exemplary implementations were performed that demonstrate the specific binding of CEA+ cancer cells to anti-CEA mAb modified microrockets. For example, the exemplary implementations involved interactions between anti-CEA mAb-modified microrockets and CEA+ pancreatic cancer cells (e.g., cells with CEA), interactions between anti-CEA mAb-modified microrockets and CEA− pancreatic cancer cells (e.g., cells without CEA), and interactions between SAM-modified microrockets without the mAb and CEA+ pancreatic cancer cells.

Figure 4A:
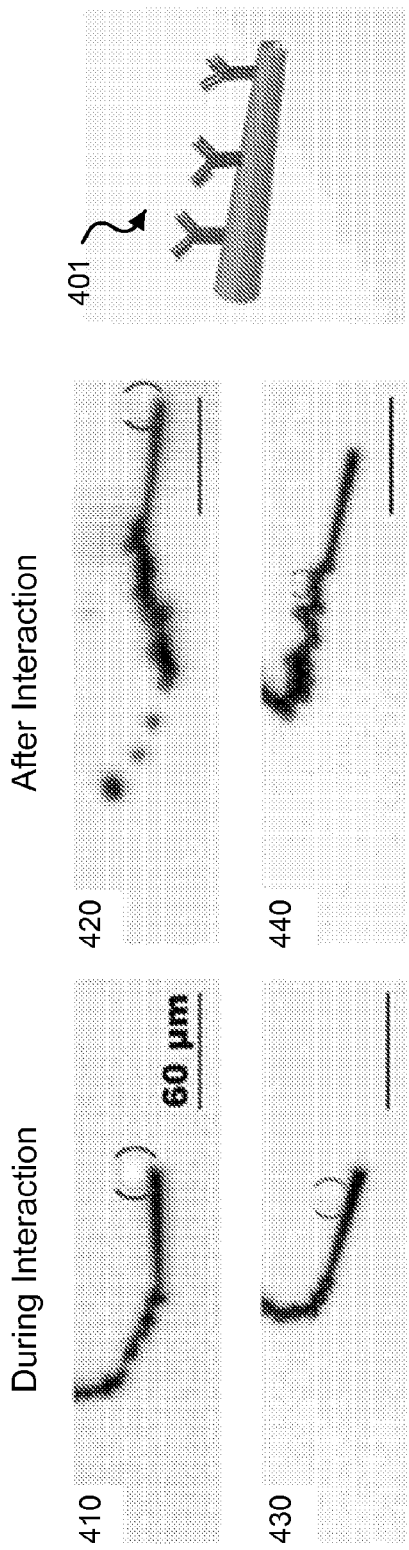
FIGS. 4A and 4B show exemplary illustrations of modified and unmodified microrockets and time lapse images demonstrating selectivity between cancer cells and the microrockets.
Figure 4B:
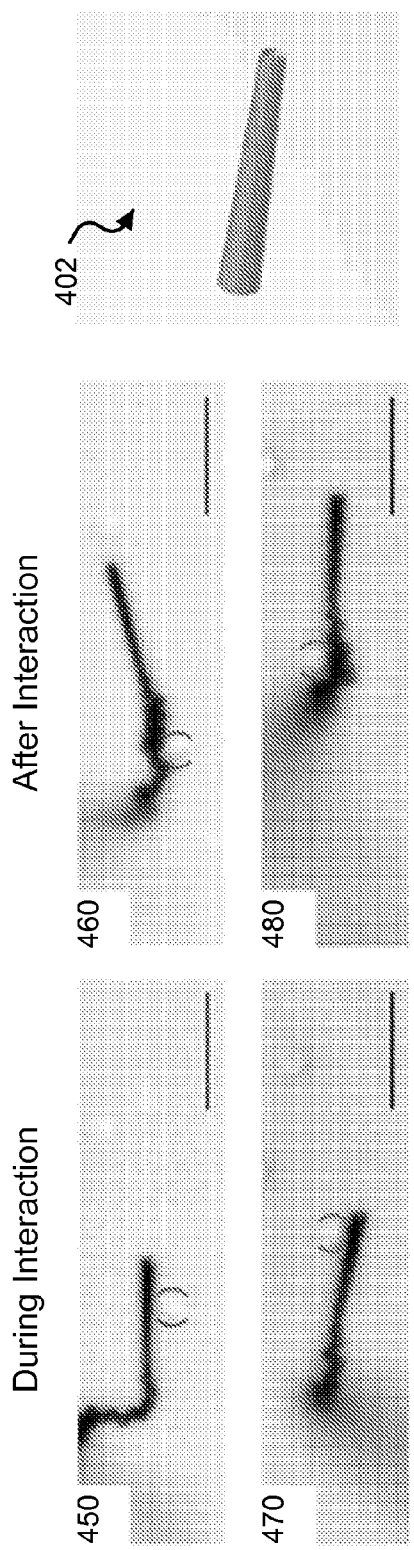

FIGS. 4A and 4B show time lapse images and illustrations of exemplary selectivity during the interaction and after the interaction between modified microrockets with the anti-CEA mAb (e.g., illustration 401 shown in FIG. 4A) and unmodified microrockets (e.g., illustration 402 shown in FIG. 4B). In FIG. 4A, the exemplary images 410 and 430 show the functionalized microrocket during the interaction with a pancreatic cancer cell, and the exemplary images 420 and 440 show the functionalized microrocket after the interaction with the pancreatic cancer cell. Images 410 and 420 show the exemplary functionalized microrocket interactions with CEA+ cancer cells (seen inside the blue circle), and images 430 and 440 show the exemplary functionalized microrocket interactions with CEA− cancer cells (seen inside the red circle). In FIG. 4B, the exemplary images 450 and 470 show the non-functionalized microrocket during the interaction with a pancreatic cancer cell, and the exemplary images 460 and 480 show the non-functionalized microrocket after the interaction with the pancreatic cancer cell. Images 450 and 460 show the exemplary non-functionalized microrocket interactions with CEA+ cancer cells (seen inside the blue circle), and images 470 and 480 show the exemplary functionalized microrocket interactions with CEA− cancer cells (seen inside the red circle). Conditions of the exemplary implementations included the use of 1×PBS buffer (pH 7.4) containing 7.5% (w/v) H$_2$O$_2$ and 1% (w/v) sodium cholate. The exemplary images shown in FIGS. 4A and 4B demonstrate that the capture of cancer cells can occur through the specific antigen recognition capability of the functionalized microrockets, e.g., as shown in images 410 and 420. For example, the exemplary anti-CEA mAb modified microrockets were capable of capturing the target CEA+ cancer cells. The exemplary images also show that none of the control implementations were successful in picking-up cancer cells (e.g., images 430 and 440 in FIG. 4A and images 450, 460, 470, and 480 in FIG. 4B). The exemplary microrockets implemented in the control experiments were also configured to move slower (e.g., average speed of 45 μm/s) to provide a better opportunity to interact with the cancer cell, e.g., by minimizing the exerting shear stress (e.g., 0.7 dynes/cm$^2$) and maximizing the rocket/cell interaction time. Interactions between the CEA+ cancer cells and mAb-modified microrockets (e.g., illustrated in image 401) were further confirmed to be strong and specific, e.g., by oscillating the pair vigorously using a magnet.

Figure 5A:
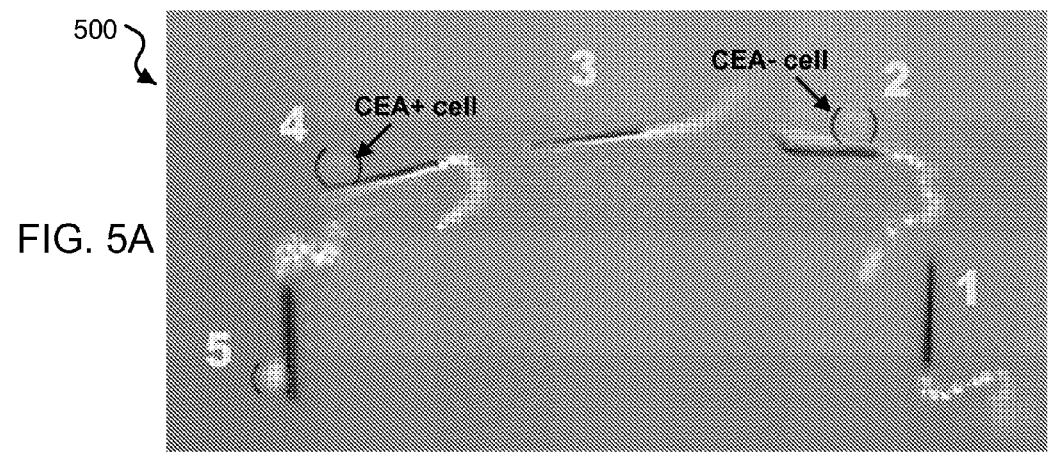
FIG. 5A shows an exemplary overlay image demonstrating isolation of a target cell in a mixture of cells by a functionalized microrocket.

Exemplary implementations were performed to demonstrate the ability of exemplary anti-CEA mAb modified microrockets to identify and isolate target cancer cells from a mixture of cells, e.g., using a mixture of green fluorescently stained CEA+ and unstained CEA− cancer cells. FIG. 5 shows an exemplary overlay image 500 demonstrating isolation of a CEA+ pancreatic cancer cell in mixture of cells by an exemplary anti-CEA mAb-modified microrocket. Conditions of the exemplary implementations included the use of 1×PBS buffer (pH 7.4) containing 7.5% (w/v) H$_2$O$_2$ and 1% (w/v) sodium cholate. For example, the overlay images 500 was created from video images showing sequential steps (1-5) of the movement of the exemplary anti-CEA mAb-modified microrocket in a solution containing both CEA+ cancer cells and CEA− cancer cells. In FIG. 5, CEA+ cancer cells are highlighted in blue circles, and CEA− cancer cells are highlighted in red circles. As shown in step 1 and step 2 of the overlay image 500, the exemplary anti-CEA mAb-modified microrocket closely interacts with the CEA− cell, e.g., hitting and displacing it to a different focal plane (e.g., due to lack of reaction). After such direct contact without picking-up the CEA− cell, the exemplary anti-CEA mAb-modified microrocket continues travel, as shown in step 3 of the overlay image 500. The exemplary anti-CEA mAb-modified microrocket captures a CEA+ cell (shown in step 4) and transports the CEA+ cell. In this example, the CEA+ cell is tightly bound to the modified rocket. For example, deliberate oscillations were performed to further validate the capture capability of the functionalized microrocket. For example, selective binding was confirmed by exposing the sample to a blue light (e.g., 460 nm), which can excite the CEA+ cells stained with a green fluorescent dye (e.g., step 5). Exemplary CEA− cells are indicated by a lack of fluorescence while exposed to blue light, as shown in FIG. 5.

Figure 5B:
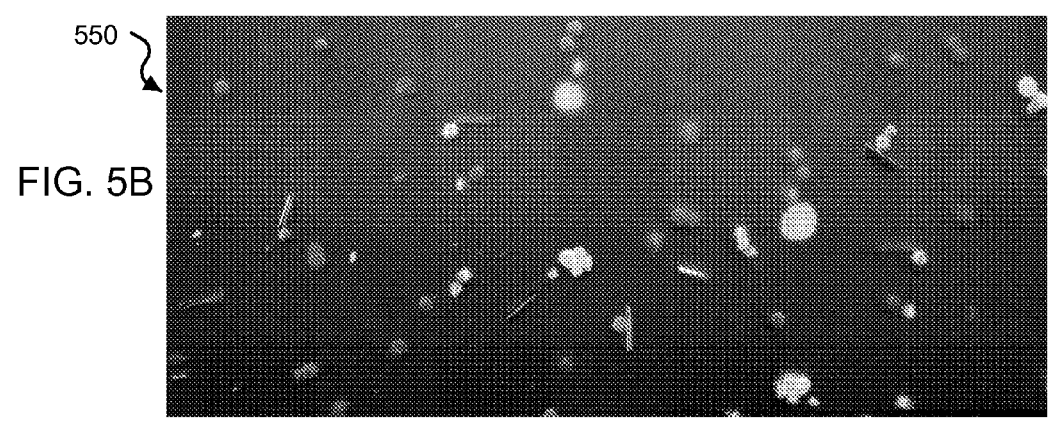
FIG. 5B shows an exemplary compiled snap shot image of antibody-modified microrockets after incubation in a mixture containing both antigen-having (green stained) and non-antigen-having (blue stained) cancer cells.

Similar exemplary implementations were performed involving the incubation of modified microrockets (e.g., without fuel) with a mixture of CEA+ and CEA− cells that can further demonstrate the selectivity of mAb-modified microrocket (e.g., FIG. 5B). For example, FIG. 5B shows an exemplary image 550 compiled of snap shot images showing exemplary anti-CEA mAb-modified microrockets after incubation in a mixture containing both CEA+(green stained) and CEA− (blue stained) cancer cells. The exemplary implementations shown in FIGS. 5A and 5B can confirm the ability of the disclosed functionalized microrockets to selectively recognize target cells (e.g., cancer cells) in cell mixtures and demonstrate the potential of this methodology for clinically-relevant applications.

Materials used in the exemplary implementations of the disclosed technology are described. For example, 6-Mercaptohexanol (MCH), 11-mercaptoundecanoic acid (MUA), N-hy droxysuccinimide (NHS), 1-(3-dimethylaminopropyl)-N'-ethylcarbodiimide hydrochloride (EDC) and sodium cholate (NaCh) were acquired from Aldrich. For example, mouse anti-carcinoembryonic antigen (CEA), Clone Col-1 (18-0057) (anti-CEA), and Sybr Green II nucleus staining dye, and 4',6-diamidino-2-phenylindole (DAPI, nucleus staining) were acquired from Invitrogen (Carlsbad, Calif.). For example, bovine serum albumin (BSA), human serum (from human male AB plasma), KCl, $Na_2HPO_4$, $K_2HPO_4.3H_2O$ and NaCl were acquired from Sigma. Exemplary reagents were used without any further purification. Exemplary implementations were carried out at room temperature. For example, for tissue culture, 10% fetal bovine serum (FBS) was acquired from Hyclone (Logan, Utah); sodium bicarbonate was obtained from Cellgro (Herndon, Va.); RPMI culture medium, penicillin/streptomycin, sodium pyruvate, L-glutamine, and MEM non-essential amino acids were acquired from Invitrogen (Carlsbad, Calif.); and EDTA powders were acquired from Fisher Scientific. Other solutions employed included 1×PBS buffer (pH 7.4) and 1% BSA solution (e.g., prepared in the same PBS buffer). Exemplary chemicals used were of analytical-grade reagents, and deionized water was obtained from a Millipore Milli-Q purification system (18.2 MΩ cm).

Fabrication of the exemplary microrockets can be implemented using the described techniques. For example, for exemplary Ti—Fe—Au—Pt microtube rockets, a positive photoresist (Microposit S1827, Microchem, Newton, Mass.) serving as a sacrificial layer was spin-coated on a silicon wafer at 3000 rpm for 60 seconds. The exemplary coated-wafer was baked at 115° C. for 60 seconds and exposed to UV light with an MA6 mask aligner, e.g., for 35 sec to create predefined patterns. The exposed patterns were developed using a MF-321 developer, e.g., for 90 seconds, and thoroughly washed with DI water. The exemplary metallic layers of Ti: 10 nm, Fe: 15 nm, Au: 5 nm and Pt: 10 nm were deposited sequentially using an e-beam evaporator under high vacuum conditions (e.g., $<10^{-4}$ Pa). The e-beam substrate holder was tilted to 50° in order to asymmetrically deposit metals on the patterns. Upon selective removal of the exposed photoresist layer using MF-1165 (Rohm & Haas, Marlborough, Mass.), the exemplary prestressed metallic layers self-assembled into microtubes. The exemplary microtube rockets were washed and stored in isopropanol before undergoing critical-point drying to maintain structural integrity. A thin (~60 nm) gold layer was sputtered onto the rolled-up microtubes to facilitate surface functionalization, e.g., with the antibody receptor through the assembly of alkanethiols. In this example, Au-coated Ti—Au—Pt microtube engines and Ti—Fe—Au—Pt microtube engines having an exterior Au surface and interior Pt surface were produced. Other examples can include Au-coated Ti—Ni—Au—Pt microtube engines, bimetal microtube engines (e.g., such as Au—Pt microtube engines), or Au-coated polymer-platinum microtube engines (e.g., a polyaniline (PANI) polymer in Au-PANI-Pt, Au—Fe-PANI-Pt, and Au—Ni-PANI-Pt microtubular engines), as well as other configurations. For example, the diameter of the exemplary nano/microengines can range from 280 nm to 1 mm. For example, nanoengines can be configured with a diameter substantially 300 nm and a length substantially 3 μm. For example, microengines can be configured with a diameter substantially 30 μm (e.g., the smaller diameter) and 50 μm (e.g., the larger diameter) and a length substantially 150 μm or 300 μm.

Modification of the exemplary microrockets can be implemented using the described techniques. For example, the external gold surface of the exemplary fabricated microrockets was modified by an overnight immersion in a binary mixture of 2.5 mM of MUA and 7.5 mM of MCH in absolute ethanol. For example, after washing with ultra-pure water, the exemplary microrockets modified with the resulting mixed monolayer were treated with a solution of NHS (20 mM) and EDC (10 mM) in ultra-pure water, e.g., for 30 min, followed by an 1 hr immersion in a solution of 1×PBS buffer (pH 7.4) containing 2 μg/ml of anti-CEA mAb. The remaining reactive groups of the activated monolayer were blocked with 1 M ethanolamine (pH 8.5) for 30 min. The exemplary microrockets were subsequently immersed in a 1% (w/v) solution of BSA in 1×PBS buffer (pH 7.4) for 1 hr. Finally, the modified microrockets were washed for 60 s with ultra-pure water and resuspended in 1×PBS buffer (pH 7.4). Exemplary incubation steps were carried out at room temperature followed by immersion in ultra-pure water for 1 min.

Exemplary microrockets without functionalization (e.g., modification with the mAb) were prepared using the protocol described above (e.g., with the SAM assembly, activation and blocking steps), but omitting the addition of the anti-CEA mAb and carrying out the corresponding incubation in buffer (without mAb). For example, it is noted that the anti-CEA mAb-modified microrockets can be used to capture and transport CEA+ cells if they are stored (up to 2 weeks) in 1×PBS buffer (pH 7.4) at 4° C. For example, it is noted that the exemplary Fe layer of the microrocket can be susceptible to the presence of HCl salt in EDC during activation of the —COOH groups of the monolayer, e.g., which can render them non-magnetic. For example, the magnetic property of the exemplary microrockets can be maintained by including approximately 3 times more Fe layer. This can allow for effective propulsion and proper navigation of modified microrockets even in complex biological media.

Figure 6:
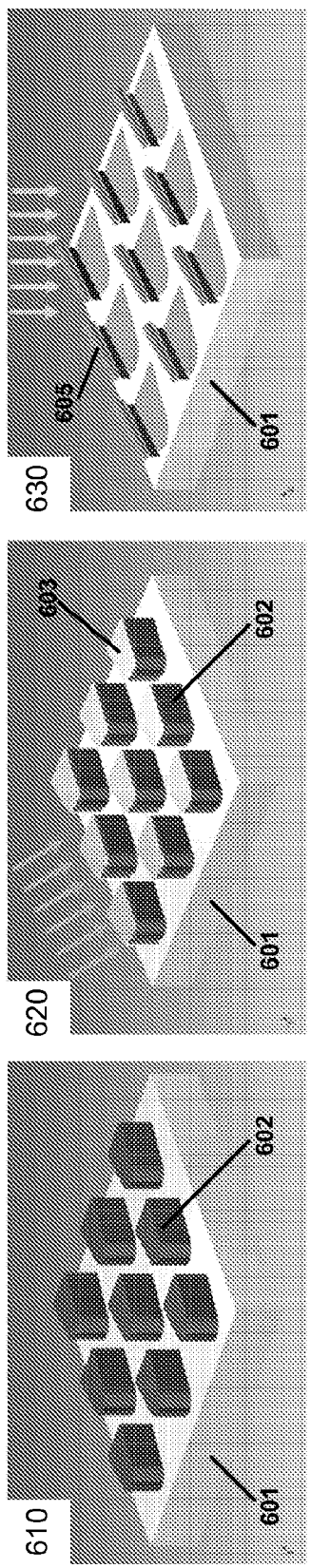
FIG. 6 shows an illustration of an exemplary fabrication technique to produce microrockets of the disclosed technology.
Figure 6:
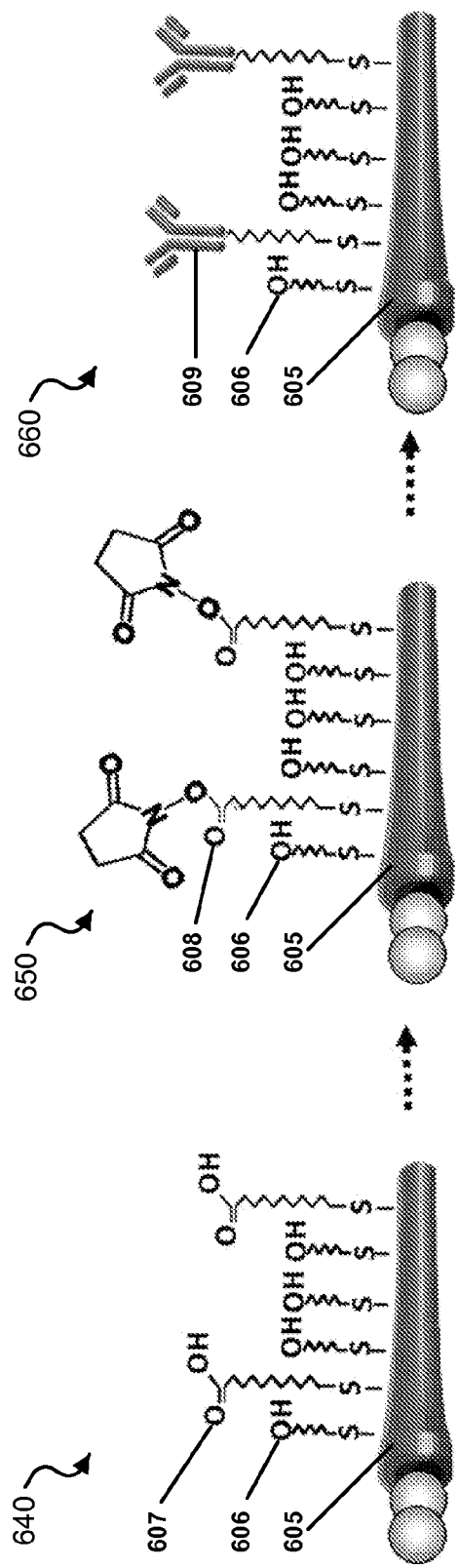

FIG. 6 shows an illustration of an exemplary fabrication technique to produce microrockets of the disclosed technology. For example, the exemplary microrocket fabrication technique can employ photolithography and chemical procedures to produce functionalized microrockets, e.g., with mAb. As shown in FIG. 6, schematic 610 illustrates a process of exposing a photoresist layer on a surface 601 to produce 'rocket' patterns 602. For example, surface 601 can include a silicon wafer having a deposited positive photoresist layer that is exposed to UV light by a mask aligner to produce micro- and/or nano-scale 'rocket' patterns 602. Schematic 620 illustrates a multilayer metal evaporation process performed at an angle, e.g., at 50° angles, to form deposited metal layers 603 to create a strain for a roll-up process into micro/nanoscale tubes (e.g., 'micro/nanorockets' of the disclosed technology). Schematic 630 illustrates a sputtering process to form a layer, e.g., a gold layer, on the rolled-up micro/nanotube 605, which can be subsequently chemically modified. For example, surface functionalization of exemplary micro/nano-rockets can be performed with the anti-CEA mAb receptor. Schematic 640 illustrates a self-assembling process to form a binary self-assembled monolayer (SAM) interface on the surface of the rolled-up micro/nanotube 605. For example, an MUA/MCH-based binary SAM interface can be produced by forming a MCH assembly 606 and a MUA assembly 607 on the rolled-up micro/nanotube 605. Schematic 650 illustrates a process showing the conversion of the carboxylic terminal groups of the MUA assembly 607 to amine-reactive esters by the EDC and NHS coupling agents to form an amine-reactive MUA assembly 608 on the rolled-up micro/nanotube 605. Schematic 660 illustrates a process showing the reaction of NHS-ester groups with the primary amines of the anti-CEA mAb antibody 609 that yield stable amide bonds to form an antibody-functionalized micro/nano-rocket.

Exemplary cells used the exemplary implementations were maintained and prepared, e.g., using the described techniques. Exemplary human pancreatic CEA-positive BxPC-3 (CEA+ cells) and CEA-negative XPA-3 (CEA− cells) cell lines were maintained in RPMI-1640 medium supplemented with 10% fetal calf albumin, penicillin/streptomycin, L-glutamine, MEM nonessential amino acids, sodium bicarbonate, and sodium pyruvate. For example, both cell lines were cultured at 37° C. with 5% $CO_2$. Cells were prepared in suspension, e.g., each cell line was detached following 20 min incubation in PBS (without Ca/Mg) containing 15 mM of EDTA. The exemplary cells were then pelleted and resuspended in PBS with Ca/Mg. The viability of the cells was confirmed using a Trypan blue dye exclusion assay. Prior to their fluorescent imaging, the BxPC-3 and XPA-3 cells were nuclear stained in 1× Sybr Green II and DAPI solution, respectively.

For example, exemplary microrockets functionalized with the anti-CEA mAb were isolated from the substrate surface and suspended in 1×PBS buffer (pH 7.4). For example, a mixture of microrockets suspension (1 μL) and sodium cholate solution (1% (w/v), 3 μL) was added to a freshly cleaned glass slide. To this, 5 μL of suspended cancer cells and 3 μL of $H_2O_2$ solutions were added (final peroxide concentration, 7.5% (w/v)). Exemplary microrockets traveling along the bottom (glass) surface can experience an additional frictional force. These exemplary microrockets were used in control and mixture experiments to increase the interaction time between the rocket and CEA-cells. For example, the exemplary microrockets were magnetically guided towards the CEA+ and CEA− cells to evaluate and identify cell-microrocket interaction. Exemplary monitoring of cell-microrocket interaction used, for example, a Nikon Eclipse TE2000S fluorescence microscope. Exemplary video images were captured using CoolSNAP $HQ^2$ camera, 20× objective (unless mentioned otherwise), and acquired at the frame rate of 10 using the Metamorph 7.1 software (Molecular Devices, Sunnyvale, Calif.). Exemplary snap shot images in static cell-capture studies on mixture samples were taken with a DeltaVision deconvolution microscope.

Figure 7:
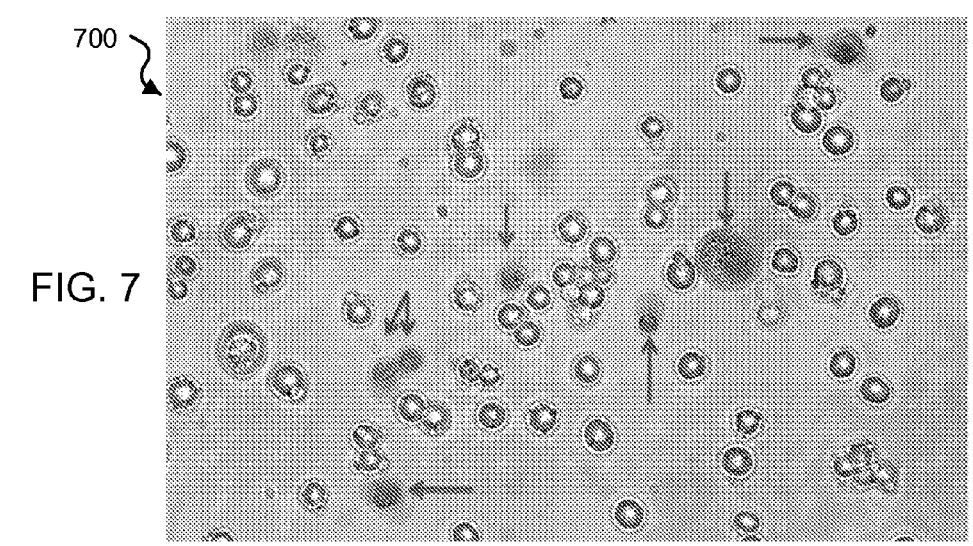
FIG. 7 shows an exemplary image showing the viability of cancer cells having carcinoembryonic antigen in buffer.

Other exemplary implementations were performed that demonstrate the viability of the cells under the exemplary conditions previously shown, e.g., using the Trypan blue exclusion assay. An exemplary Trypan blue exclusion implementation was performed to determine the number of viable cells present in a cell suspension after exposure to the exemplary conditions used in the capture and transport implementations previously described. For example, cancer cells were subject to PBS solutions containing various levels of the peroxide fuel. FIG. 7 shows an exemplary image 700 showing the viability of cancer cells having carcinoembryonic antigen in buffer. For example, CEA+ cells were incubated in PBS solutions containing 1% (w/v) sodium cholate and various concentrations of the peroxide fuel, e.g., 2% (w/v) $H_2O_2$. After different incubation times, the cell suspension was mixed with the dye and then it was examined under a microscope to determine whether the cells take up or exclude the dye. The image 700 was acquired after 45 min of incubation. The exemplary arrows shown in image 700 indicate Trypan blue stained dead cells. It is noted that under all exemplary conditions assayed dead cells retained spherical shape (e.g., no cell lysis). The exemplary implementation resulted in over half of the cells remained viable for over 10 minutes at the 8% peroxide level, and the majority of the cells (e.g., >90%) remained viable after 1 hour immersion in a 2% peroxide solution, as shown in Table 3. Such time windows would allow for the retrieval of cells for subsequent analysis. Also noted is the ability of the mAb-coated rockets to bind to dead CEA+ cells or their cellular membrane fragments. Thus, the exemplary microrockets can identify any CEA-expressing cell (or other targeted antigen expressed) regardless of the cell's viability.

Table 3 includes data showing viability of CEA+ pancreatic cancer cells in the presence of PBS solution containing 1% of sodium cholate and various concentrations of $H_2O_2$.

TABLE 3

| $H_2O_2$ concentration, % (w/v) | Viability Window |
| --- | --- |
| 8 | 50% viable, 10 min |
| 5 | 50% viable, 22 min |
| 2 | >90% viable, >1 h |
| 1 | >90% viable, >1 h |

Various implementations have been described for an exemplary in-vitro strategy for isolating cancer cells, e.g., based on the selective binding and transport ability of mAb-functionalized microengine rockets. The exemplary microrockets can be functionalized with targeting ligands (e.g., antibodies such as mAb) for highly specific cancer cell selection. The exemplary microrockets can provide sufficient propulsive force for the efficient transport of the captured target cells in fluids, e.g., complex biological fluids. Exemplary implementations were performed and described showing the capture of pancreatic cancer cells. The disclosed technology can also be configured to capture, isolate, and transport other cancer or healthy cell lines. The exemplary microrockets can selectively capture and transport of tumor cells without pre-processing fluid samples, e.g., extracting CTCs from biological fluids and implementing the early diagnosis of cancer and its recurrence. The disclosed microrockets include autonomous transport properties enabling motion in viscous fluids, e.g., serum. The disclosed microrockets are capable of altering the nature of interactions (e.g., by controlling shear stress), which can be implemented to increase the efficiency of viable cell separation processes. The disclosed microrockets can be employed in a system that includes a micromachine-based cell manipulator and sorter, e.g., which can incorporate microchannel networks for creating integrated microanalytical chip devices. For example, such exemplary microchips of the disclosed technology can be implemented for the active transport of multiple functionalized micromachines in a blood sample reservoir to induce numerous interactions, high capture efficiency and single-step isolation of CTCs. In other examples, exemplary microchips of the disclosed technology can be extended to applications including accumulating CTCs in a predefined 'collection' area, e.g., by detaching the captured cells under low-pH elution buffer combined with sonication.

Fabrication techniques of nanoscale and microscale motors of the disclosed technology can include template assisted fabrication of catalytic tubular microengines.

Microscale and nanoscale structures can be engineered to be capable of locomotion through fluid environments. For example, synthetic micro- and nano-machines can locomote through fluids, e.g., by using catalytic reactions to create forces based on chemical gradients. For example, chemically powered catalytic motors can exhibit autonomous self-propulsion, e.g., in the presence of hydrogen peroxide fuel. The disclosed technology can include electrochemical propulsion of bimetal (e.g., Au—Pt, Au—Ni) microscale tubes through an electrokinetic self-electrophoresis mechanism. For example, this exemplary propulsion mechanism can operate the disclosed chemically powered catalytic microscale tubes in low and high ionic strength aqueous solutions. The disclosed technology can include template-assisted processes to fabricate microscale tubes and cones (also referred to as microtube engines, microengines, microtubes, microcones, microrockets, and micromotors), e.g., based on sequential electrodeposition of platinum and gold layers onto an etched silver wire template, and followed by dicing and dissolution of the silver wire template.

The exemplary template-assisted fabrication techniques can be implemented to produce synthetic bubble-propelled microengines. For example, the exemplary chemically powered motors can be prepared by plating a catalytic platinum surface onto predefined silver wire templates. A gold outer layer can be added to prevent bubble formation on the external surface. Also, a gold outer layer can enable functionalization of the microengine, e.g., facilitating self-assembly of thiolated self-assembled monolayers (SAM) that can further attach ligand molecules or other structures. In some configurations, an intermediate nickel layer can be included for magnetic navigation and cargo transport.

FIG. 8 shows a schematic illustration of the exemplary template-assisted technique to fabricate microtube engines of the disclosed technology. The exemplary technique shown in FIG. 8 includes preparation steps using a silver (Ag) template, e.g., which can include electroplating of the platinum (Pt) and gold (Au) layers, dicing of the coated wire, and dissolution of the silver template. Schematic 810 shows the exemplary etching of Ag wire 811, e.g., using nitric acid to dissolve regions of the Ag wire 811 to form etched Ag wire 812. Schematic 820 shows the exemplary deposition of platinum and gold layers to form a Pt—Ag wire 821 and a Au—Pt—Ag wire 822, respectively. For example, the Pt and Au layers can be electroplated onto etched Ag wire 812. In some examples, additional layers can be deposited over the Au—Pt—Ag wire 822, e.g., Ti—Au—Pt—Ag wires. The Pt—Ag wire 821 and/or the Au—Pt—Ag wire 822 can be diced into a desired length and dimension. Schematic 830 shows an exemplary diced electroplated Au—Pt—Ag microtube 834, e.g., having a concave geometry that remains when Pt and Au are electroplated. Schematic 840 shows an exemplary Au—Pt—Ag microtube engine 845, e.g., after dissolution of the silver template.

For example, the described technique can allow detailed control over the tube dimensions, geometry, or materials and hence upon the performance of the microengine. For example, an optimal motor geometry can be selected based on critical design considerations, e.g., aimed at maximizing the intertial propulsion and minimizing viscous effects. The disclosed template-assisted preparation technique and can be implemented to produce well-defined, bimetal conical microtube engines. Exemplary conical microtube engines can operate, for example, by facilitating the entrance of a fuel through the small radial opening, with a catalytically generated gas bubbles traveling along a sloped transition and ejecting out from a larger radial opening to generate the force propelling the engine.

FIG. 9A shows an illustration showing the propulsion of microtube engine 911 in an ionic solution. In this example, the microtube engine 911 can locomote by generating oxygen microbubbles 912 electrocatalytically on the inner platinum surface 913, e.g., in which the oxygen microbubbles 912 are ejected from the larger opening of the microcone structure that propel the motor. For example, a peroxide fuel can enter the microcone structure of the microtube engine 911 through the small radial opening 915. The exemplary peroxide fuel can undergo electrocatalytic decomposition on the inner platinum surface 913 to produce oxygen gas that nucleates into bubbles, e.g., forming oxygen microbubbles 912. The oxygen microbubbles 912 can travel along a sloped transition and exit through the larger opening 916 of the microcone (e.g., due to the pressure differential caused by the asymmetry of the size of the inlet and outlet openings). The exiting oxygen microbubbles 912 can produce a force in the opposite direction of the bubble ejection and result in axial movement of the microcone body of the microtube engine 911.

This exemplary oxygen-bubble propulsion mechanism of the disclosed microengines can address ionic-strength limitations exhibited by other nano- and micro-motor modalities. For example, the disclosed microengines can exhibit salt-independent movement, e.g., including high-speed propulsion in high ionic-strength medium (e.g., one molar salt). In other examples, magnetically directed movement and transport of heavy cargo can be implemented through the deposition of an intermediate nickel layer.

FIG. 9B shows an exemplary SEM images 920 of an etched Ag wire (e.g., exemplified in schematic 810 of FIG. 8) with a diameter 50 μm. For example, an exemplary nitric acid treatment can be implemented for etching of a cylindrical silver wire into a concave microcone. For example, the exact length and dimensions of the microcone can be controlled by dicing, and the degree of concavity can be controlled by etching conditions, e.g., including etching time and concentration of nitric acid. For example, the conical shape of the wire template (after the nitric acid etching) is indicated in the SEM image 920. For example, the concave geometry curvature can minimize the turbulent flow inside the micromotor and provide a favorable gradient for forward propulsion. Additionally, this exemplary engineered geometry can also impact increased efficiency of the oxygen-bubble production and overall controlled fluid flow.

FIG. 9C shows an exemplary SEM image 930 of the resulting Pt—Au tubular microcone, e.g., following the Ag dissolution step exemplified in schematic 840 of FIG. 8. The SEM image 930 shows the open Pt—Au tubular microcone after dissolution of the silver template. The nitric acid etching resulted in a smoothed internal Pt surface, along with a rough external gold surface (associated with the electrodeposition of the gold).

Figure 10A:
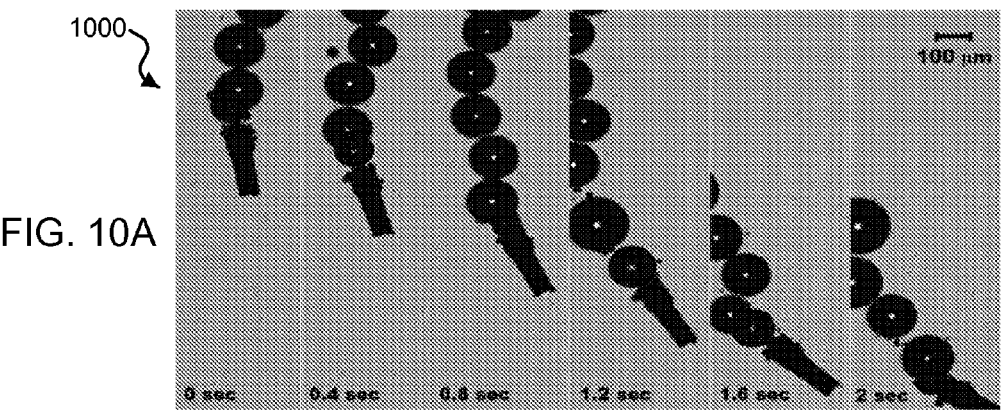
FIGS. 10A-10D show exemplary images demonstrating propulsion of microrockets in a fluid.

FIG. 10A shows time lapse images 1000 of the movement of an exemplary catalytic micromotor in a 15% peroxide solution over a 2 s period at 0.4 s intervals. These exemplary time lapse images show a tail of microbubbles (e.g., ~100 μm diameter) catalytically generated on the inner surface of the exemplary microengine and released from the rear of the microengine, e.g., at a rate of 10 bubbles/s. For example, ejection of the microbubbles from the larger opening of the microengine can propel the microstructure forward, e.g., at a speed of 456 μm/s, corresponding to around three body lengths/s. For example, lowering the peroxide fuel concentration resulted in a decreased bubble frequency and a slower motor speed of 186 μm/s in 5% $H_2O_2$.

Figure 10B:
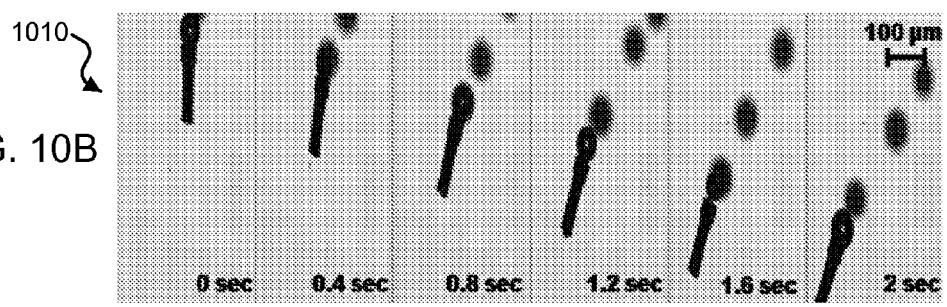

FIG. 10B shows time-lapse images 1010 of the motion of an exemplary catalytic micromotor in the presence of 1 M NaCl. These exemplary time-lapse images of the motion in this salt-rich environment indicate a high rate of bubble generation and motor speed, e.g., of 183 μm/s in 5% $H_2O_2$. For example, as compared with the salt-free environment demonstrated in FIG. 10A, the exemplary high ionic-strength medium (e.g., 1 M NaCl) in FIG. 10B showed minimal effect on the propulsion of microtube engines, e.g., by 1-3% decrease.

The geometry and dimensions of the silver wire template can be configured to engineer various performance parameters of the disclosed micromotors. For example, changes in shape, diameter, length, or surface chemistry can be implemented on the silver wire template (e.g., silver wire 811 shown in FIG. 8). The disclosed techniques can allow detailed control over the microstructure materials. For example, exemplary implementations were performed that used a polymeric polypyrrole (PPy) outer layer instead of gold. Exemplary microtubes fabricated using a PPy outer layer yielded bubble generation from the external surface, e.g., because of the porous nature of PPy. Other examples can include the incorporation (e.g., deposition) of an intermediate nickel (Ni) layer, e.g., which can be implemented with a magnetic stimulus to aid the pickup of a cargo or load. In other examples, various geometries of tubular micromotors (e.g., cylindrical, step cone, and smooth cone) were examined in connection with different diameters of the silver wire template (e.g., ranging from 25 to 100 μm). For example, favorable propulsion was observed for Pt—Au tubular micromotors formed from 50 μm wire templates. Other exemplary design considerations can include flow losses in single-phase duct flow of stepped and coned tubular geometries. For example, exemplary implementations with straight duct, stepped cone, and smooth cone designs—e.g., with different inlet/outlet area ratios—yielded positive results. For example, the cone geometry (e.g., shown in FIGS. 8 and 9A-9C) displayed a streamlined efflux of bubbles, a large bubble-formation frequency, and an enhanced micromotor speed and power. The exemplary design of the microengines having a microcone body (e.g., microtube engine 911) can avoid sudden pressure drops or bubbles evolving from both sides. In some examples, excellent performance of the cone geometry based microengines was obtained using a length of 150 μm and inlet and outlet diameters of 30 μm and 50 μm, respectively.

Figure 10C:
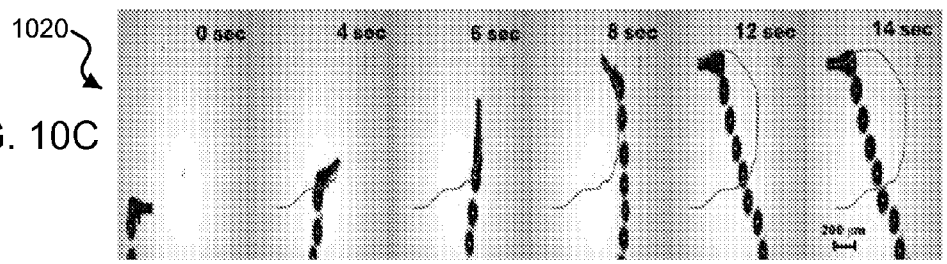

The propulsion capabilities of the disclosed conically-shaped microtube engine (e.g., microtube engine 911) can be coupled with a magnetically directed movement with the introduction of a magnetic metal layer. For example, the template-assisted preparation protocol (e.g., described in FIG. 8) can allow the incorporation of an additional magnetic layer. For example, a nickel layer can be readily electroplated on top of the platinum layer and subsequently coated with an external electroplated gold layer. The ability to use magnetic control to guide the motion of the exemplary Pt—Ni—Au microengine is shown by exemplary time lapse images in FIG. 10C. FIG. 10C displays time-lapse images 1020 during the magnetically guided U-shaped movement of the exemplary Pt—Ni—Au microengine over a 14 s period in a 5% $H_2O_2$ solution. The incorporation of a ferromagnetic Ni layer into the exemplary microcone body enabled a magnetic remote control and guidance in the pre-selected U-shaped route. The exemplary magnetically-guided motion can be accomplished without compromising the engine speed.

Figure 10D:
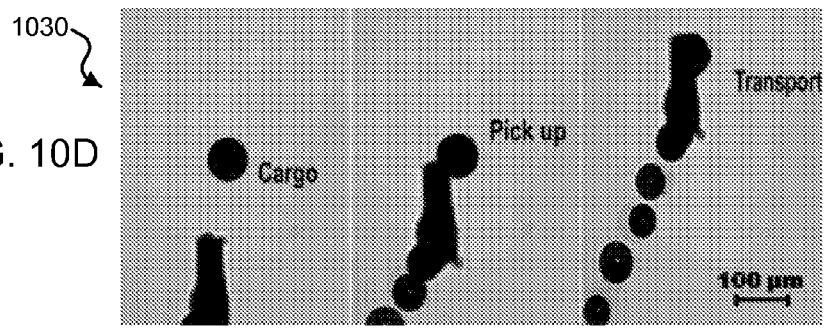

FIG. 10D shows sequential optical micrographs 1030 that demonstrate the ability of the magnetic tubular microengines to load a spherical (100 μm diameter) cargo and transport it along predetermined paths. For example, exemplary implementations were performed to demonstrate the guided movement of a Pt—Ni—Au microengine toward a large magnetic-sphere "cargo", the dynamic loading of the cargo onto the propelled microtube, and the transport of the cargo over a predetermined path. The exemplary image data of FIG. 10D also indicates that the speed of the microengine is not compromised by the cargo loading, reflecting the high propulsion power.

In other examples, a surfactant substance (e.g., Triton X-100) can be added to the fuel solution, e.g., which can lead to formation of dense smaller bubbles. For example, low concentrations of Triton X-100 were added to the fuel to reduce the hydrophobic nature of the Pt layer and the surface tension, e.g., which may improve the Pt wetting (e.g., with the aqueous peroxide fuel solution) and reduce drag (e.g., that can be caused by polar attractions between the aqueous solution and gold outer layer). The exemplary reduction in bubble size can lead to a smaller propulsive force and to smoother propulsion (with shorter moving "steps"). For example, exemplary implementations were performed and data acquired that showed an increased bubble frequency (e.g., ~80 bubbles/s) and streamlined propulsion. For example, the propulsion speed can be reduced by utilizing the exemplary surfactant with the microengine fuel, e.g., slower speeds of around 250 μm/s in 15% $H_2O_2$, or ca. 1.5 body lengths (compared to over 450 μm/s without the surfactant). For example, this result can be attributed to lower propulsion forces generated by bubbles of smaller radius compared to larger ones.

Various geometries of the exemplary micromotors (e.g., cylindrical, step cone, and smooth cone) were prepared by a sequential electrodeposition of platinum (Pt) and gold (Au) layers onto a silver microwire template (e.g., 3 cm long, 50 µm diameter, 99.9% purity), as shown in FIG. 8. For example, silver microwires were initially secured under tension to an elevated platform. Concaved geometry templates were obtained by etching silver wire at evenly spaced segments, e.g., with 30% nitric acid droplets (10 µL) for 30 s, and followed by a thorough rinsing with distilled water. The exemplary etched silver wire template was soldered to tin-coated copper wire contact and served as a "working electrode" for the subsequent electrodeposition steps. A Pt—Au electrodeposition technique was used in connection to different shapes of the silver wire template. For example, platinum was deposited galvanostatically at −2 mA for 240 s using a platinum plating solution (Platinum RTP; Technic Inc., Anaheim, Calif.) along with a Pt wire counter electrode and Ag/AgCl (3 M KCl) reference electrode. Subsequently, Au was electrodeposited at −0.9 V from a gold plating solution (Orotemp 24 RTU RACK; Technic Inc.) for 200 s. The Pt—Au-coated silver wire templates were diced at desired locations using a DAD3220 Disco automatic dicing saw to create 150-300 µm long segments. The exemplary silver wire template was subsequently dissolved for 5 min using 25% (v/v) nitric acid. This exemplary process created tubular microcones with an inner platinum surface covered by an external gold layer. These exemplary tubular motors were collected by centrifugation, e.g., at 2000 rpm for 2 min, and washed repeatedly with nanopure water (e.g., 18.2 MΩ·cm) until a neutral pH was achieved. The exemplary tubular microcones were stored in nanopure water at room temperature, and their speed was tested on the same day of synthesis. The resulting microcone tubes were tested for their movement in a aqueous solution of hydrogen peroxide fuel solution. The influence of the surfactant (Triton X-100) upon the propulsion of exemplary Pt—Au tubular microcones was examined by mixing a 15% hydrogen peroxide solution with solutions of Triton X-100 (0.1% in water) with a 1:0.1 ratio.

For magnetically directed propulsion, a nickel layer was electroplated ("sandwiched") between the platinum and gold layers. The nickel deposition proceeded for 120 s at −1.0 V using a nickel-plating solution [20 g L$^{-1}$ NiCl$_2$.6H$_2$O, 515 g L$^{-1}$ Ni(H$_2$NSO$_3$)$_2$.4H$_2$O, and 20 g L$^{-1}$ H$_3$BO$_3$ (buffered to pH 3.4)]. In this example, the silver template was dissolved in a H$_2$O$_2$/NH$_4$OH (1:1) solution. The exemplary tubular motors were magnetically directed and guided by rotating the external magnet pair at ~10 cm away from the glass slide without changing the distances. This position can allow changes of an alignment in the direction of tubular motor by a weak magnetic field. For the examples including an outer layer of polypyrrole (PPy) (e.g., instead of Au), the outer layer was prepared by cycling the potential between 0 to 1.0 V at a scan rate of 100 mV/s using 0.5 mM pyrrole solutions containing either tetraethylammonium tetrafluoroborate in acetonitrile (vs. a Ag/Ag$^+$/ACN nonaqueous reference electrode) or sodium chloride (vs. Ag/AgCl, 3 M KCl reference electrode) in water as dopants. For exemplary cargo pickup implementations, polystyrene beads (100 µm Polysciences, Inc., Warrington, Pa.) were acquired and dispersed as monolayers on pre-cleaned glass slides. The top side of the dried polystyrene was coated with a titanium layer (e.g., 25 nm thick) followed by 100 nm of nickel and 200 nm of gold using an Ebeam evaporator (Temescal BJD 1800).

Exemplary images were captured using an inverted optical microscope (Nikon Instrument Inc., Eclipse TE2000-S), e.g., equipped with a 5× objective and a Photometrics CoolSnap HQ2 camera (Roper Scientific, Duluth, Ga.). For example, images were taken at a rate of 10 frames/s. The micromotor movement was tracked using Metamorph 7.1 software (Molecular Devices, Sunnyvale, Calif.). Exemplary tracking of tubular micromotor movement utilized an optical microscope (Nikon Instrument Inc., Eclipse 80i, Melville, N.Y.). The morphology of microtubes was examined by field emission scanning electron microscopy (SEM) (Phillips XL30 ESEM).

In another aspect, the disclosed technology can include functionalized microstructures for selective rapid isolation of nucleic acids from complex samples, e.g., during locomotion of the exemplary functionalized microstructure in a fluid.

For example, the disclosed microstructures can be incorporated with devices, systems, and techniques to capture, isolate and transport target biomolecules, e.g., by self-propelling or externally actuated means to locomote the functionalized microstructures. The functionalized microstructures can be functionalized with ligand biomolecules, such as antibodies, nucleic acids, aptamers, lectins, etc., that have an affinity to a receptor molecules, e.g., independent target biomolecules or target biomolecules on living cells).

Exemplary microstructures are disclosed for selective isolation of target nucleic acids from complex biological matrices based on 'on-the-fly' hybridization and transport capabilities, e.g., by implementing a nucleic acid probe-modified microengine rocket. Nucleic acids can be capable of quick, fast, accurate means to identify targeted compliments. Exemplary implementations are described that demonstrate the movement and capture/isolate/transport capabilities of the disclosed nucleic acid probe-modified microrockets, e.g., exhibiting quick and efficient capture and isolation nucleic acid-based targets from small (e.g., microliter) samples, e.g., biological samples without pre-processing with minimal nonspecific binding. The exemplary functionality of the disclosed nucleic acid probe-modified microrockets can be further utilized to transport the collected isolate from various raw samples to a clean environment before undergoing post-analysis (e.g., such as PCR) to confirm the product on the same device.

For example, efficient and reliable nucleic acid extraction from complex biological samples/matrices can play an important role in subsequent analytical, preparative and downstream processing, e.g., which can be used for the identification of genetic disorders or food and environmental contamination. Nucleic acid extraction purity can be sensitive to factors such as incomplete cell lysis, nonspecific adsorptions, coextraction of PCR inhibitors and nucleic acid degradation.

The exemplary nucleic acid probe-functionalized micromotors can include specific nucleic acid receptors that enable the selective, sensitive and rapid isolation of target nucleic acids (e.g., DNA, RNA) from complex media and biological samples, e.g., raw bacterial lysate, serum, saliva, urine. In some examples, the target can be tagged with a fluorescent tracer (e.g., fluorescence nanoparticles or fluorescence detector probe), which can offer convenient and direct optical monitoring of the target hybridization and duplex-transport processes. The exemplary nucleic acid probe-functionalized microrockets can move by a catalytic bubbling propulsion producing a strong convection effect that increases the hybridization rate and enhances the target capture efficiency at fixed time. For example, the guided navigation of these autonomously micromotors can allow for the transportation of isolated targets across a PDMS-based microchannel of a biosensor to a clean environment (e.g., on the biosensor) that can be validated using post-analysis methods. Disclosed is the exemplary integration of the nucleic acid probe-functionalized micromotors in a complete lab-on-chip device that can provide, for example, a quick, cost-effective, system-automated, high-throughput means to obtain and characterize highly purified nucleic acid based substances.

Figure 11A:
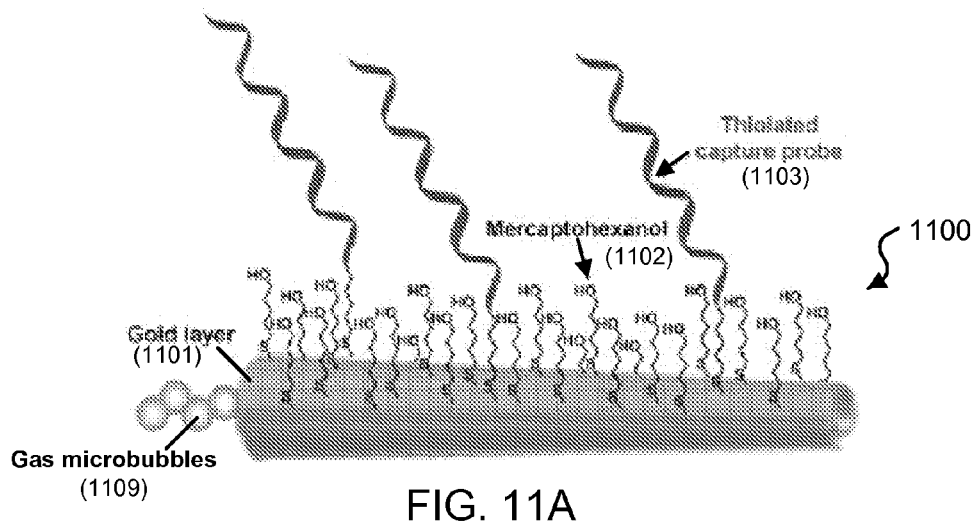
FIGS. 11A-11C show schematic illustration of nucleic acid-functionalized microrockets for target biomolecule or cell isolation and downstream analysis.

FIG. 11A shows a schematic illustration of an exemplary nucleic-acid functionalized microtube rocket 1100 engineered to self-propel in a fluid to capture, isolate, and/or transport a target biomolecule. For example, the exemplary microrocket 1100 can include a tubular structure coated by a gold layer 1101 that is functionalized by a molecular layer. The molecular layer can include a binary SAM having a thiolated capture probe (SHCP) 1103 and a short-chain linear alkanethiol 1102 (e.g., a mercaptohexanol such as 6-mercapto-1-hexanol (MCH)). For example, the binary SAM attached to the Au layer 1101 of the microtube can ensure an efficient hybridization process, e.g., by minimizing nonspecific binding. The exemplary SHCP 1103 can include a single strand oligonucleotide (e.g., DNA or RNA based oligonucleotides), aptamers, peptide nucleic acids (PNA), and hairpin probes, among other configurations. For example, nucleic acid-functionalized microrocket 1100 can self-propel by allowing a fuel (e.g., a peroxide fuel) in the fluid through the small radial opening and catalytically generating gas microbubbles 1109 along its inner surface that eject out from the larger radial opening to produce a propulsion force.

Figure 11B:
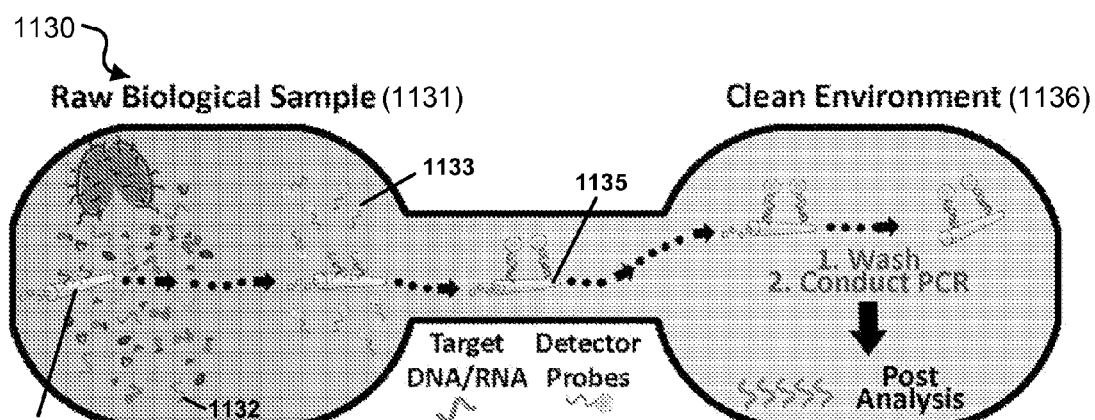
Figure 11C:
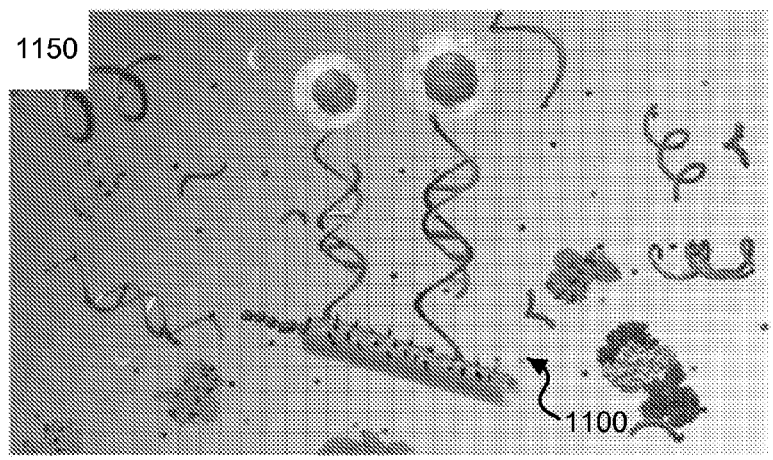

FIGS. 11B and 11C show schematic illustrations of the nucleic acid-functionalized microrocket 1100 capturing and isolating target biomolecules based on an 'on-the-fly' target hybridization in biological samples. For example, FIG. 11B shows an illustration 1130 demonstrating the nucleic acid-functionalized microrocket 1100 moving around a raw biological sample 1131, e.g., by self-propulsion based on catalysis of a fuel such as hydrogen peroxide. In the raw biological sample 1131, the movement of the nucleic acid-functionalized microrocket 1100 can allow and/or facilitate interaction with a target oligonucleotide 1132 (e.g., target DNA/RNA). In some examples, the raw biological sample can include a fluorescent-tagged target nucleic acid 1133 (e.g., synthetic 30 mer-DNA or bacterial 16S rRNA). For example, after some time to allow for exemplary binding of the target biomolecules to the nucleic acid-functionalized microrocket 1100, the microrockets with the captured target nucleic acid can be propelled with an external steering (e.g., magnetically-guided) through an exemplary microchannel towards a 'clean' detection zone (e.g., clean environment 1136). For example, within the clean environment 1136, the exemplary isolated nucleic acids 1133 on the collected microrockets can be further detached from the nucleic acid-functionalized microrocket 1100 and subsequently analyzed, e.g., by using bioanalytical methods such as PCR. FIG. 11C shows a schematic illustration 1150 that demonstrates the nucleic acid-functionalized microrocket 1100 that has captured target nucleic acid molecules, e.g., even among the diversity of components contained within the raw biological sample 1131.

For example, during their motion, the receptors on the modified microrockets can interact with a model target pre-labeled with a fluorescent tag or an actual target from a raw sample which are later identified through its interaction with another fluorescent labeled detector molecule. For example, if the target of interest is rather large such as cells, the receptor-cell interaction and capture can be clearly identified with an optical microscope. After interacting for a given period of time (e.g., between 5 to 30 min), which can be influenced based on target concentration, volume, or sample matrix, the disclosed nano/micromotor may then be directed across the PDMS microchannel to the docking station in clean environment. The exemplary isolated microrockets can serve as solid supports for the subsequent molecular or biochemical analysis (e.g., PCR directly over the microengine with the captured target nucleic acid). For example, if the target of interest is a nucleic acid and/or protein, the isolated targets can be accurately measured or analyzed, e.g., using Image-J fluorescent intensity software for quantitation after thorough washing. Further downstream analysis (e.g., such as qPCR, gel electrophoresis or sequencing technology) can be employed to validate the isolation and to further quantitate the capture efficiency. The same concept is applicable to different synthetic nano/microscale motors in connection to diverse surface receptors and target biomolecules.

FIG. 12 shows exemplary optical microscope images 1250, 1260, and 1270 demonstrating the motion-based target hybridization and isolation process implemented by exemplary nucleic acid-functionalized microrockets. For example, image 1250 shows selective isolation of a fluorescent-tagged target sequence (e.g., 25 nM concentration) by the rapidly moving functionalized microrockets. Image 1260 shows a comparative functionalized microrocket having a large excess (e.g., 250 nM concentration) of 3-based mismatched (3-MM) nucleic acids. Image 1270 shows a comparative functionalized microrocket having non-complementary (NC) sequences. The exemplary images of FIG. 12 were taken 10 minutes after incubation in the respective samples. For example, images 1250, 1260, and 1270 demonstrate a highly efficient hybridization of the DNA target to the capture probe on the modified-microrocket surface. This exemplary result is indicated, for example, by the relatively complete coverage of the microengine with fluorescent nanoparticles that firmly adhered to the functionalized rocket shown in image 1250, e.g., microrockets moving at ~4 body lengths per second (e.g., 240 μm/sec). In images 1260 and 1270, the presence of a 10-fold excess of 3-MM an NC nucleic acids, respectively, did not produce visible binding of the fluorescently-labeled sequences on the modified-microrocket surface, e.g., even after significantly longer incubation times (e.g., of 25-30 min). The exemplary implementations shown in FIG. 12 demonstrate the effective discrimination against non-complementary or multiple-mismatched sequences by the highly selective microrocket, which can be configured for capture and isolation of a target nucleic acid.

FIG. 13 shows exemplary optical microscope time lapse images demonstrating the influence of hybridization time and target concentration on the uptake of the fluorescent-tagged target DNA. Images 1310, 1320, and 1330 represent the time lapse progression of the 'on-the-fly' target hybridization (25 nM) on a moving nucleic acid-functionalized microrocket, e.g., following 0, 7, and 12 min in hybridization buffer (HB), respectively. Images 1340, 1350, and 1360 represent the time lapse images obtained after exposure of the modified microrockets to different target DNA concentrations, e.g., 1.25 nM, 12.5 nM, and 125 nM, respectively, after 8 min in HB. The quantity of the target nucleic acid captured on the modified microrocket was shown in FIG. 13 to be associated with its concentration in solution and the interaction time. For example, the number of captured particles gradually increased upon increasing the hybridization time in the 25 nM target DNA solution (shown in images 1310, 1320, and 1330). For example, at a fixed incubation time (e.g., of 8 min), the fluorescence intensity of the modified microrocket was shown to increase with the concentration of target DNA, e.g., over the 1 and 100 nM range. It is noted that the composition of the hybridization buffer (e.g., high ionic strength and large presence of biologically inert proteins like BSA) does not compromise the movement of microrockets, which were observed to move in this medium for more than 30 min without significant loss in speed. For example, the fuel does not affect the hybridization efficiency or the integrity of the binary (SHCP+MCH) monolayer assembled on the microrockets.

Figure 14A:
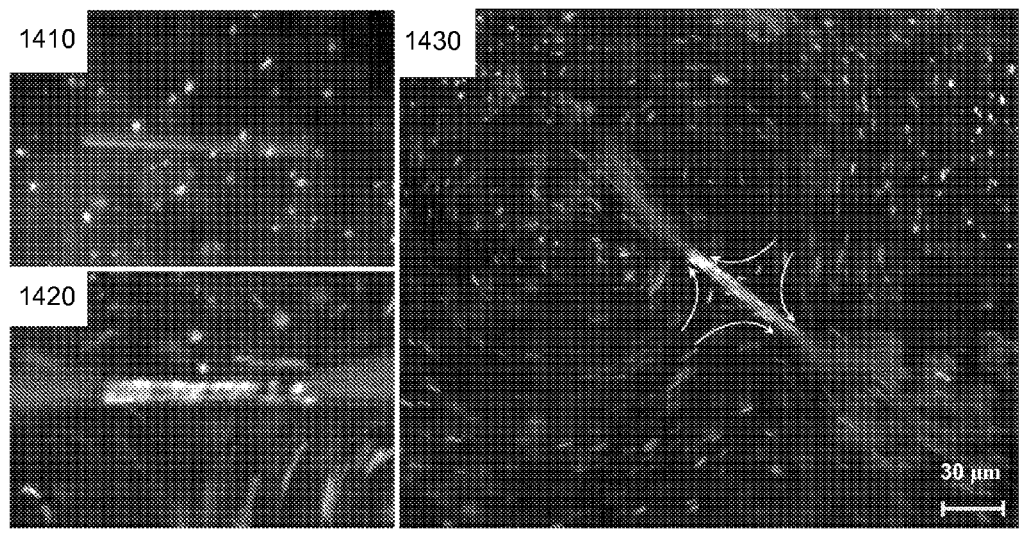
FIG. 14A shows images that demonstrate the generation of microbubbles thrusted out of the openings of the exemplary microrockets.
Figure 14B:
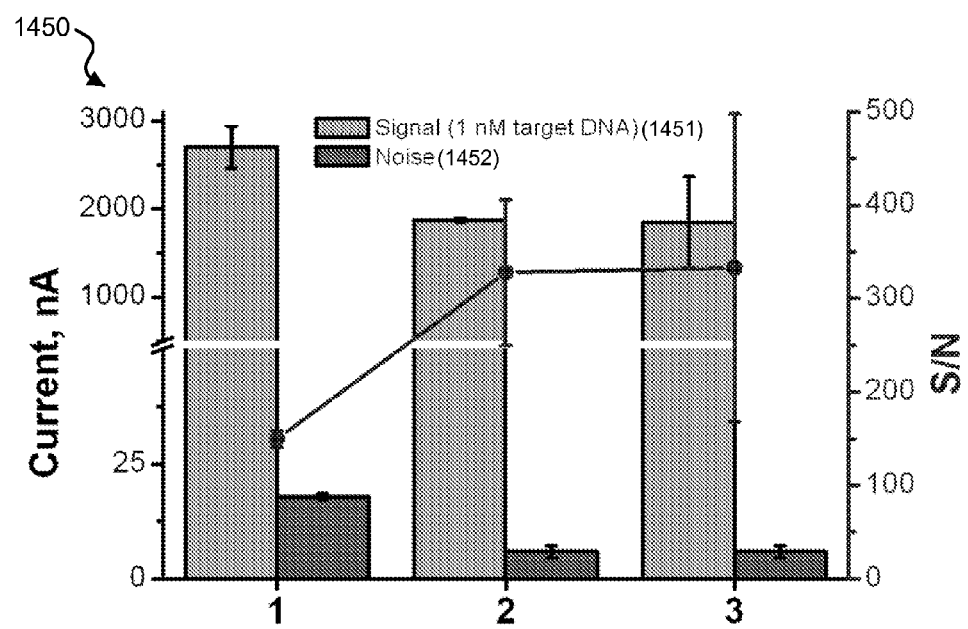
FIG. 14B shows a data plot that demonstrates the exemplary effect of peroxide fuel on the DNA hybridization on the functionalized microrockets.

For example, a bubble-induced self-convection of the target nucleic acid, e.g., due to the self-propulsion mechanism of the microrockets, can significantly enhance the hybridization efficiency of the targets to the ligands on the microrocket. This can provide a significant advantage of the disclosed functionalized microrockets for nucleic acids extraction implementations. For example, FIGS. 14A and 14B show data images and a data plot exemplifying the difference in target hybridization efficiency for microrockets incubated with hydrogen peroxide fuel compared to those without the fuel. The exemplary time lapse images 1410, 1420, and 1430 obtained after a 20 min incubation of the modified microrockets in a HB solution containing the target DNA (25 nM) without $H_2O_2$ (image 1410) and with $H_2O_2$ (images 1420 and 1430). For example, FIG. 14A shows images 1410, 1420, and 1430 that demonstrate the generation of microbubbles thrusted out of the openings of the exemplary microrockets. For example, image 1430 shows that fast movement of the microrocket can create a vortexing mixing effect around the modified micromachine that can increase the capture probe availability for target binding and improve the transport of the labeled target. This exemplary vortexing mixing effect can thereby cause an increase in the target binding rate to the functionalized microrocket, e.g., improving the hybridization efficiency at fixed time. For example, the locomotion-induced hybridization kinetic/rate enhancement of the exemplary microrockets can also minimize the undesirable non-specific adsorption of non-complementary/mismatched nucleic acids or other possible components of the complex samples.

FIG. 14B shows data plot 1450 that demonstrates the exemplary effect of peroxide fuel on the DNA hybridization on the functionalized microrockets. For example, signal detection of 1 nM target DNA (green columns 1451) and the corresponding blank noise (0 M target DNA) signals (red columns 1452) are shown, along with the resulting S/N ratio (blue line). Exemplary conditions of the experimental implementations included pure HB (represented by the left data (1)), HB containing 5% of $H_2O_2$ (represented by the middle data (2)), and HB containing 5% of $H_2O_2$ and 1% (w/v) of sodium cholate (represented by the right data (3)). Plot 1450 demonstrates the presence of $H_2O_2$ and sodium cholate can have a minimal effect on the background noise, e.g., with nearly the same hybridization signal when testing with 1 nM of target DNA. These exemplary results can confirm that the SHCP+MCH SAM is stable under the exemplary conditions used for microrockets locomotion.

Figure 15:
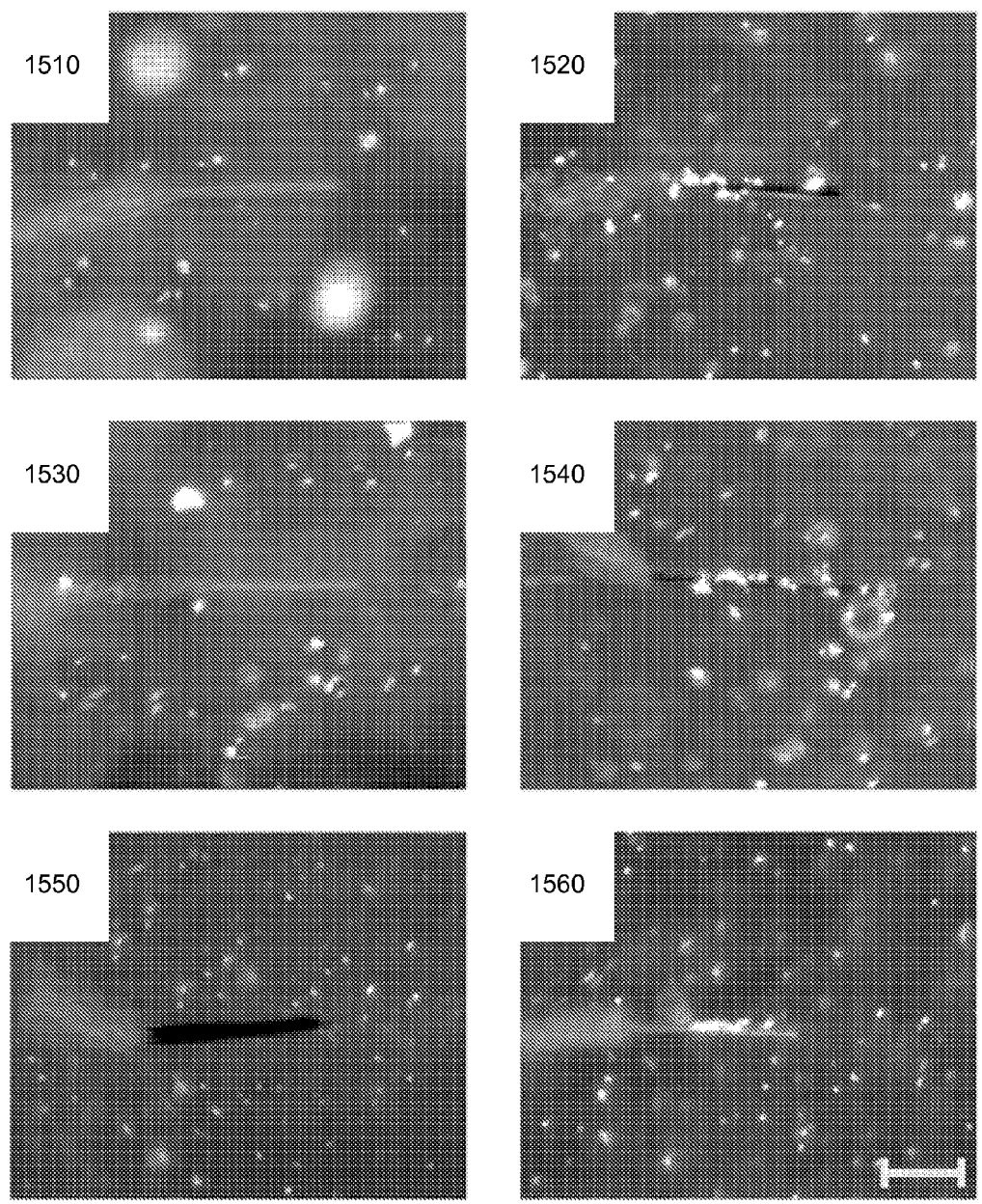
FIG. 15 shows exemplary images of the modified microrockets propelling in the biological samples to isolate the target DNA.

The propulsion of modified-microrockets in complex biological samples, e.g., plasma, serum, urine or saliva, can allow for efficient isolation of the target nucleic acid without sample processing steps or procedures. Exemplary implementations were performed to demonstrate the ability of the SHCP+MCH-modified microrockets (e.g., microrocket 1100) to move and isolate target nucleic acid in untreated biological samples. For example, FIG. 15 shows exemplary images of the modified microrockets propelling in the biological samples to isolate the target DNA. The target DNA capture efficiency was assayed in 10% of human urine (images 1510 and 1520), 100% human serum (images 1530 and 1540), and 20% of human saliva (images 1550 and 1560). For example, the exemplary SHCP+MCH-modified micromotors propelled in the biological samples containing 20 nM of target DNA (images 1520 and 1540), 200 nM of NC oligonucleotide (images 1510 and 1530) and rRNA corresponding to K. pneumoniae $1.8\times10^5$ CFUs/µL (image 1550) and to E. coli $7.5\times10^2$ CFUs/µL (image 1560). For example, images 1510-1540 were captured after 9 min of incubation and (images 1550 and 1560) after 6 min. For example, the practical utility of the disclosed methodology was implemented for the isolation of E. coli 16S rRNA from raw bacterial lysate sample solutions. For example, specificity of the bioassay was evaluated using as no-target biological control K. pneumoniae. The incubation in the raw E. coli lysate sample solution resulted in the attachment of numerous fluorescence particles to the modified microrockets (image 1560); in contrast, no fluorescence (e.g., binding) was observed for a high (240-fold) excess of K. pneumoniae 16S rRNA (image 1550).

The exemplary data shown in FIG. 15 indicate that the disclosed structures, devices, and methodologies can offer high specificity for the capture of the target nucleic acids, e.g., even in the presence of complex biological samples. For example, direct isolation of bacterial nucleic acids in complex sample matrices was shown, which can be important in variety of applications including clinical and biothreat detection. For example, the disclosed functionalized microrockets can move over long periods (e.g., greater than 30 min) in these complex biological samples while maintaining their speed. For example, the capture efficiency can be associated with the matrix composition of the fluid, which, for example, may be attributed to the slight effect of the viscosity upon the micromotors' locomotion and hybridization rate. In other examples, the presence of some components in the biological fluids may hinder the hybridization efficiency or consume the fuel (e.g., reaction with urea to produce carbamide peroxide, $CH_4N_2O.H_2O_2$).

Figure 16:
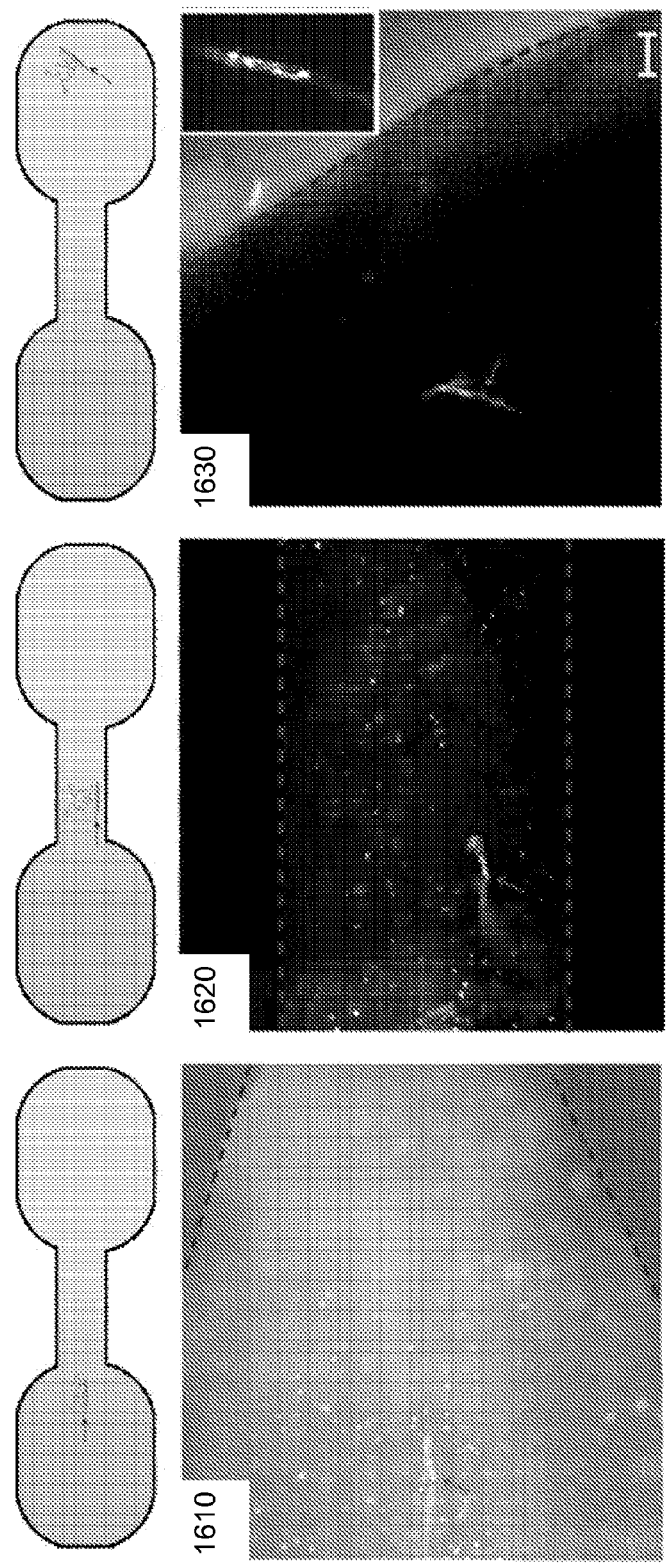
FIG. 16 shows schematic illustrations and exemplary images of the nucleic acid modified-microrockets implemented in a device for capturing and transporting a target from a biological sample zone to a characterization zone.

FIG. 16 shows schematic illustrations and exemplary images of the nucleic acid modified-microrockets implemented in a device that can allow capture and transport of captured target DNA across a PDMS microchannel from a "dirty" sample zone to a "clean" well, e.g., for subsequent release and characterization. For example, the exemplary data shown in FIG. 16 is based on the exemplary schematic of FIG. 11B. For example, the optical images 1610, 1620, and 1630 in FIG. 16 depict the process as a modified micromotor captures the target DNA in a sample reservoir (image 1610) and transports it across a 6-mm-long channel (image 1620) to a clean well (image 1630) for post-analysis by releasing it. For example, transport of the exemplary nucleic acid modified-microrocket occurred across the 6-mm channel within 80 sec. The power and efficiency of the modified microrockets can enable for the transport of the isolated DNA against a hydrostatic pressure gradient, e.g., artificially created in this example to prevent diffusion from the "dirty" to "clean" wells and further validate the functionality of the microrocket propulsion technology.

Many practical nucleic acid isolation applications can require that effective motor propulsion is maintained in complex matrices for long durations of time. The movement capabilities of the functionalized microrockets was evaluated and shown to maintain movement characteristics in different biological samples (as shown in Table 4A) over longer periods of time (as shown in Table 4B). For example, the speed of most microrockets is only slightly affected by the biological media even after longer periods of time. In some examples, the microrockets speeds increased overtime, e.g., which could be due to a better wetting of the inner catalytic surface. Tables 4A and 4B include data showing fuel requirements, estimated speed and distance traveled by SHCP+MCH-modified microrockets after prolonged movement (around 30 min) in complex media. The asterisk (*) in Table 4 indicates average data obtained for 10 microrockets in three independent experiments.

TABLE 4A

| Media | $[H_2O_2]$, (w/w) % | NaCh, (w/v) % |
|---|---|---|
| HB | 1.4 | 0.25 |
| 100% Serum | 2.5 | 0.25 |
| 10% Urine | 2.5 | 0.25 |
| 10% Saliva | 4.3 | 1.8% |

TABLE 4B

| Media | % of micro-rockets still linearly moving* | Estimated speed*, μm/s (0 min) | (15 min) | (30 min) | Average speed, μm/s | Average distance traveled in 30 min, mm |
|---|---|---|---|---|---|---|
| HB | 95% | 53.1 | 70.0 | 83.7 | 68.9 | 124 |
| 100% Serum | 80% | 45.1 | 41.1 | 47.5 | 44.6 | 80 |
| 10% Urine | 85% | 46.2 | 57.8 | 75.8 | 59.9 | 108 |
| 10% Saliva | 40% | 60.3 | 49.1 | 47.2 | 52.2 | 94 |

Table 5 shows the oligonucleotides used in these exemplary experimental implementations. The asterisk (*) in Table 5 indicates that the sequence of the 30-mer complementary DNA target is a copy of partial region of the *E. coli* 16S rRNA gene (position 432-461 according to the 5'→3' nucleotide sequence). For example, the probe pair (SHCP and Biotin-DP) was designed to be fully complementary to both synthetic target DNA and the partial region of the *E. coli* 16S rRNA targets.

were used without any further purification. Exemplary synthetic oligonucleotides used were acquired from Integrated DNA Technologies Inc. (San Diego, Calif., USA) and are listed in Table 5. Exemplary bacterial strains of *Escherichia coli* NEB 5-α (New England Biolabs) and clinical isolates of *Klebsiella pneumoniae* (KP210) were obtained from the University of California-Los Angeles (UCLA), Clinical Microbiology Laboratory. The exemplary isolates were received in centrifuge tubes and were stored at −80° C. until use. Overnight bacterial cultures were freshly inoculated into Luria broth (LB) and grown to logarithmic phase as measured by the optical density at 600 nm. Exemplary concentrations in the logarithmic-phase specimens were determined by serial plating. The buffer solutions used in the exemplary implementations included the following: the DNA immobilization buffer (IB) was 1×PBS (pH 7.2); the hybridization buffer (HB) was a 1 M phosphate buffer solution containing 2.5% bovine serum albumin (pH 7.2). The human urine and saliva samples were taken daily and diluted appropriately in IB just before the experiment. Exemplary chemicals used were of analytical-grade reagents, and deionized water was obtained from a Millipore Milli-Q purification system (18.2 MΩ cm).

Fabrication of the exemplary microrockets can be implemented using the described techniques. For example, for exemplary Ti—Ni—Au—Pt microtube rockets, a positive photoresist (Microposit S1827, Microchem, Newton, Mass.) serving as a sacrificial layer was spin-coated on a silicon wafer at 3000 rpm for 60 seconds. The exemplary coated-wafer was baked at 115° C. for 60 seconds and exposed to UV light with an MA6 mask aligner, e.g., for 35 sec to create predefined patterns. The exposed patterns were developed using a MF-321 developer, e.g., for 90 seconds, and thoroughly washed with DI water. The exemplary metallic layers of Ti: 10 nm, Ni: 15 nm, Au: 5 nm and Pt: 10 nm were deposited sequentially using an e-beam evaporator under high vacuum conditions (e.g., <$10^{-4}$ Pa). The e-beam substrate holder was tilted to 50° in order to asymmetrically deposit metals on the patterns. Upon selective removal of the exposed photoresist layer using MF-1165 (Rohm & Haas, Marlborough, Mass.), the exemplary pre-stressed metallic layers self-assembled into microtubes. The exemplary microtube rockets were washed and stored in isopropanol before undergoing critical-point drying to maintain struc-

TABLE 5

| SEQ ID NO | Oligonucleotide | Sequence (5'→3') |
|---|---|---|
| 1 | Thiolated capture probe, SHCP | Thiol-TAT TAA CTT TAC TCC |
| 2 | Detector probe, Biotin-DP | CTT CCT CCC CGC TGA-Biotin |
| 3 | Complementary target* | Biotin-TCA GCG GGG AGG AAG GGA GTA AAG TTA ATA |
| 4 | Non-complementary sequence, NC | Biotin-CT GGG GTG AAG TCG TAA CAA GGT AAC CGT AGG GGA AC |
| 5 | 3-Base mismatched sequence, 3-MM | Biotin-TCA GCG GGG AGG AAG GGA GTC ACG TGA ATA |

Materials used in the exemplary implementations of the disclosed technology are described. For example, 6-Mercaptohexanol (MCH) was acquired from Aldrich. Bovine serum albumin (BSA), human serum (from human male AB plasma), KCl, $Na_2HPO_4$, $K_2HPO_4 \cdot 3H_2O$ and NaCl were acquired from Sigma. Streptavidin-Coated Fluorescence Microspheres (210 nm mean diameter CP01F/8905) were acquired by Bangs Laboratories Inc. Exemplary reagents tural integrity. A thin (~60 nm) gold layer was sputtered onto the rolled-up microtubes to facilitate surface functionalization, e.g., with the antibody receptor through the assembly of alkanethiols. For example, surface functionalization was performed to create a binary SHCP+MCH SAM. In this example, Au-coated Ti—Ni—Au—Pt microtube engines having an exterior Au surface and interior Pt surface were produced. Other examples can include Au-coated Ti—Fe—

Au—Pt microtube engines, Au-coated Ti—Au—Pt microtube engines, bimetal microtube engines (e.g., such as Au—Pt microtube engines), or Au-coated polymer-platinum microtube engines (e.g., a polyaniline (PANI) polymer in Au-PANI-Pt, Au—Fe-PANI-Pt, and Au—Ni-PANI-Pt microtubular engines), as well as other configurations.

Modification of the exemplary microrockets can be implemented using the described techniques. For example, the external gold surface of the exemplary fabricated microrockets was modified by an overnight immersion in a 10 μM SHCP solution prepared in IB. After washing with ultra-pure water, the microrockets modified with the SHCP were treated with a 0.1 mM MCH solution (also in IB) for 10 min to obtain a SHCP+MCH SAM. Finally, the modified microrockets were washed for 60 s with ultra-pure water and resuspended in IB. Exemplary incubation steps were carried out at room temperature. Exemplary SHCP+MCH-modified microrockets can be used for isolation of nucleic acid, e.g., stored (up to 2 weeks) in IB at 4° C.

Exemplary DNA isolation and detection procedures involved a duplex formation between the microengine-surface confined probe and the biotinylated target DNA pre-labeled with the streptavidin-fluorescence particle tag. For example, different concentrations of the DNA target were prepared in the HB and incubated for 30 min at room temperature with streptavidin-fluorescence particles diluted 60 times before exposure to the modified-microrockets. The exemplary protocol was used for the testing with the NC or 3-MM sequences. Exemplary implementations were carried out at room temperature.

Exemplary bacteria detection strategies involved "sandwich" hybridization of target 16S ribosomal RNA released from the bacterial cell to specific capture and detector probes. For example, the bacteria were lysed by resuspension of the appropriate pellet containing ~$10^7$ CFU bacteria in 10 μL of 1 M NaOH and incubation for 5 min. An exemplary 50 μL of Biotin-DP (0.25 μM) in HB was added to this 10 μL bacterial lysate, e.g., leading to genetic material corresponding to ~$10^7$ CFU per 60 μL. This exemplary solution was left to incubate 15 min at room temperature (for homogeneous hybridization in solution) and serially diluted in the Biotin-DP (0.25 μM), e.g., to provide different concentrations of bacterial genetic material (16S rRNA). The resulting solution was incubated with the fluorescence particles tags following the same protocol described earlier for the synthetic target DNA. Exemplary procedures were carried out at room temperature.

The exemplary microrockets functionalized with the SHCP+MCH SAM were detached from the substrate surface by carefully scratching with a micropipette tip and suspended in IB. For example, a mixture of microengines suspension (2 μA), sodium cholate (0.1-1.0% (w/v), 2 μL) and samples under study (2 μL) was added to a freshly cleaned glass slide. To this, 2 μL of nucleic acid solution (synthetic DNA or bacterial rRNA containing also the fluorescence particles) and 2 μL of $H_2O_2$ were added (final peroxide concentration between 1-5% (w/v) and dependent on the matrix samples assayed). The microengines were allowed to move randomly in the above solution to pick-up the target nucleic acid during the desired time and in the moment of video acquisition the microengines were magnetically guided to localize them in the observation window. Exemplary videos were captured using CoolSNAP HQ$^2$ camera, 20× objective (unless mentioned otherwise) and acquired at the frame rate of 10 using the Metamorph 7.1 software (Molecular Devices, Sunnyvale, Calif.) and Nikon Eclipse TE2000S fluorescence microscope.

An exemplary device including PDMS (Dow Corning Corporation, Midland, Mich.) was hand-mixed in a 10:1 polymer, e.g., by fixing agent ratio. For example, PDMS was poured over a glass Petri dish, degassed in a vacuum desiccator, and baked at 110° C. for 15 min. Holes of ~3 mm were punched in each well using a steel rod (Technical innovations, Brazoria, Tex.). The PDMS network had 2 reservoirs of ~3 mm wide and ~1.5 mm tall with a channel length of approximately 6 mm. The resultant structures and glass slides were exposed to UVO ozone (Jetline Co., Irvine, Calif.) at a gas flow rate of 3 sccm for 3 min, pressed together and baked for another 10 min at 110° C. to complete the bonding process. The PDMS channel was washed with ultra pure water to ensure the removal of any residual dust and dried properly under nitrogen before starting the exemplary implementations.

The exemplary implementations included a mixture of $H_2O_2$ (final concentration 3 (w/v) %), sodium cholate (final concentration 0.25 (w/v) %) and HB that was prepared and transferred to the PDMS channel until filling the channel. An appropriate volume of the modified-microrockets and fluorescence labeled-nucleic acid solution (~4 μL of each) was added to the "dirty well" simulating a real sample; a slightly higher volume of the mixture previously prepared was added to the clean well in order to generate an opposite hydrostatic pressure gradient to minimize the diffusion from the dirty channel to the clean one during the microrockets moving time required for nucleic acid capture. After allowing movement of the modified microengines in the sample reservoir during the desired time, they were magnetically guided across the channel. Ambient light and digital adjustments to brightness and contrast were used to visualize the fluorescent labeled nucleic acid, micromotor and PDMS channel at the same time. Tracking, magnetic guidance and visualization techniques were implemented as described above.

Exemplary implementations were performed to evaluate the stability of the microrocket modification and nucleic acid hybridization in the presence of the fuel (e.g., 5% $H_2O_2$ and 1% of sodium cholate). Additionally, exemplary implementations were performed in pure HB, in HB containing 5% of $H_2O_2$ and in HB containing 5% of $H_2O_2$ and 1% of sodium cholate. An exemplary electrochemical detection strategy involved a sandwich hybridization assay in which the immobilized capture probe anchors the target DNA to the sensor, and the detector probe signals the presence of the target through a reporter molecule. For example, binding of the capture and detector probes to the nucleic acid target can create a three-component "sandwich" complex on the sensor surface. An exemplary fluorescein-modified detector probe can enable binding of an antibody antifluorescein-conjugated with a reporter enzyme (horseradish peroxidase) to the target probe complex. For example, under the use of a redox enzyme co-substrate (3,3',5,5' tetramethylbenzidine, TMB, solution containing also hydrogen peroxide) and a fixed potential between the working and reference sensor electrodes, the horseradish peroxidase-mediated redox cycle can be detected by the electrochemical sensor in the form of an electric current. The amplitude of this electroreduction current reflects the concentration of the target-probe complexes immobilized on the sensor surface.

Various implementations have been described for an exemplary self-propelled nucleic acid-functionalized microrocket that can bind target substances. Exemplary implementation of the disclosed functionalized microrockets were shown to increase the hybridization rate and efficiency of isolate target nucleic acid to the capture probes attached to the microrockets in various biological samples. For example, the disclosed functionalized microrockets can generate a convection vortex that can bring target biomolecules toward the microrockets from within the fluid. The disclosed functionalized microrockets include capabilities of implementing multiple hybridizations on a single microrocket. In addition, the disclosed functionalized microrockets include the ability to control the nucleic acid hybridization kinetics (e.g., by modulating the speed of the modified microrockets). The disclosed technology can be implemented in a variety of applications that can improve speed, efficiency and other parameters of bioinformatic assays, diagnostics, therapeutic agents, and nanofabrication. For example, the nucleic acid isolation capabilities of the disclosed technology can be employed in microchannel networks for creating fully integrated devices. For example, the exemplary microchips can rely on the active transport of multiple functionalized microrockets in a sample reservoir to induce numerous interactions, high capture efficiency and single-step isolation of the target analytes. Furthermore, this can be extended to accumulating target nucleic acids in a predefined 'collection' area by releasing them using appropriate dehybridization conditions, discussed later in this patent document.

The exemplary functionalized microrockets of the disclosed technology can also be functionalized with other targeting ligands. For example, tubular bubble propulsion based microscale rockets functionalized with specific antibodies, capture probes or other targeting ligands have capabilities to isolate rare cancer cells, nucleic acids and protein antigens from raw samples.

Figure 17:
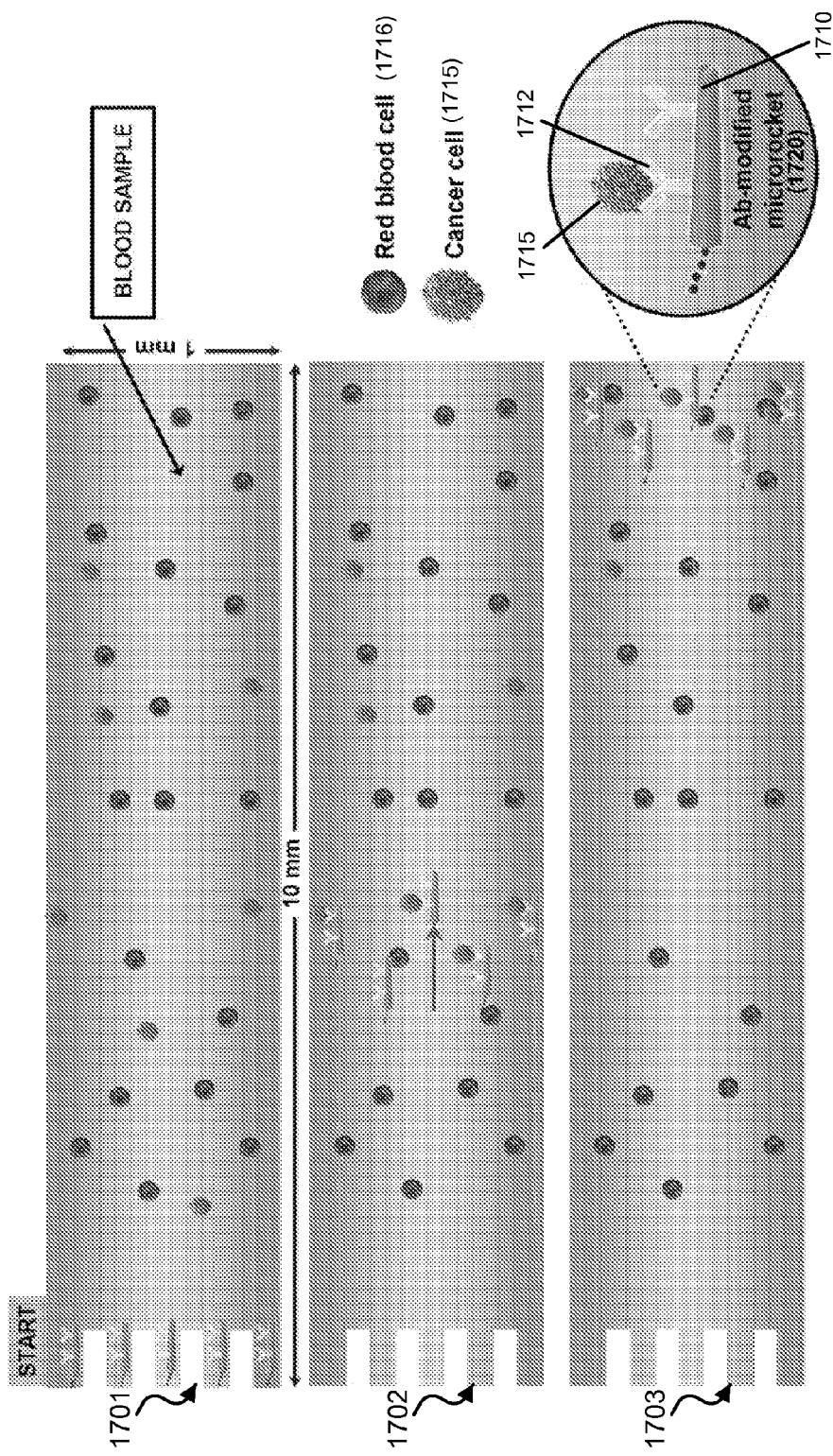
FIG. 17 shows a schematic illustration of capture and transport of circulating cancer cells in a blood sample by an exemplary functionalized microrocket.

For example, FIG. 17 shows a schematic illustration of capture and transport of circulating cancer cells in a blood sample. Schematic 1701 shows red blood cells 1716 and cancer cells 1715 circulating in the blood sample. Schematic 1702 shows Ab-modified microrocket 1720 having a gold coated microtube structure 1710 functionalized with antibodies 1712 propelling in the blood sample. Schematic 1702 shows the microrocket 1720 attaching cancer cells 1715 and bypassing red blood cells 1716. Schematic 1703 shows the microrocket 1720 transporting the attached cancer cells 1715 in the blood sample. FIG. 17 demonstrates use of functionalized nanomachines propelled through the sample, e.g., extracting target cancer cells from untreated biological fluids. The exemplary microrocket cell-sorting technique can rely on the rapid and repeated movement of multiple antibody-functionalized microrockets through the blood sample to maximize the cell-antibody contact rate. For example, by inducing numerous interactions between the target cells and the functionalized rockets, high capture efficiency and single-step CTC isolation can be achieved. The resulting motion-driven detection platform can thus provide an attractive platform for high-yield capture and transport of tumor cells without pre-processing the biological samples. Similarly, repeated motion of the DNA-capture probe or antibody functionalized micromachines can increase the contact rate with the corresponding target, and hence, the binding efficiency for higher sensitivity and/or shorter bioassays.

In another example, as shown in FIG. 18A, a schematic illustration 1800 shows a functionalized microrocket 1801 configured for capture and isolation of bacterial rRNA 1804 from a bacteria cell 1808 found in a fluid. For example, microrocket 1801 can be functionalized with a molecular monolayer having MCH backfiller 1802 and a thiolated capture probe 1803 (e.g., a lectins-based probe for carbohydrate interactions with bacterial components) for capture of the bacterial rRNA 1804. In some examples, a detector probe 1805 having a detecting molecule 1807 (e.g., a fluorophore) can be included in the fluid to attach to the bacterial rRNA 1804 for further characterization.

FIGS. 18B and 18C show exemplary time lapse images 1810 and 1820 demonstrating SHCP+MCH-modified microrocket propulsion in lysate fluid samples. Exemplary data was obtained after 6 min of incubation of the SHCP+MCH-modified microrocket in lysate samples solutions containing the genetic material corresponding to *E. coli* $3.0 \times 10^3$ CFU/µL (image 1810) and *K. pneumoniae* $7.3 \times 10^5$ CFU/µL (image 1820).

Figure 19:
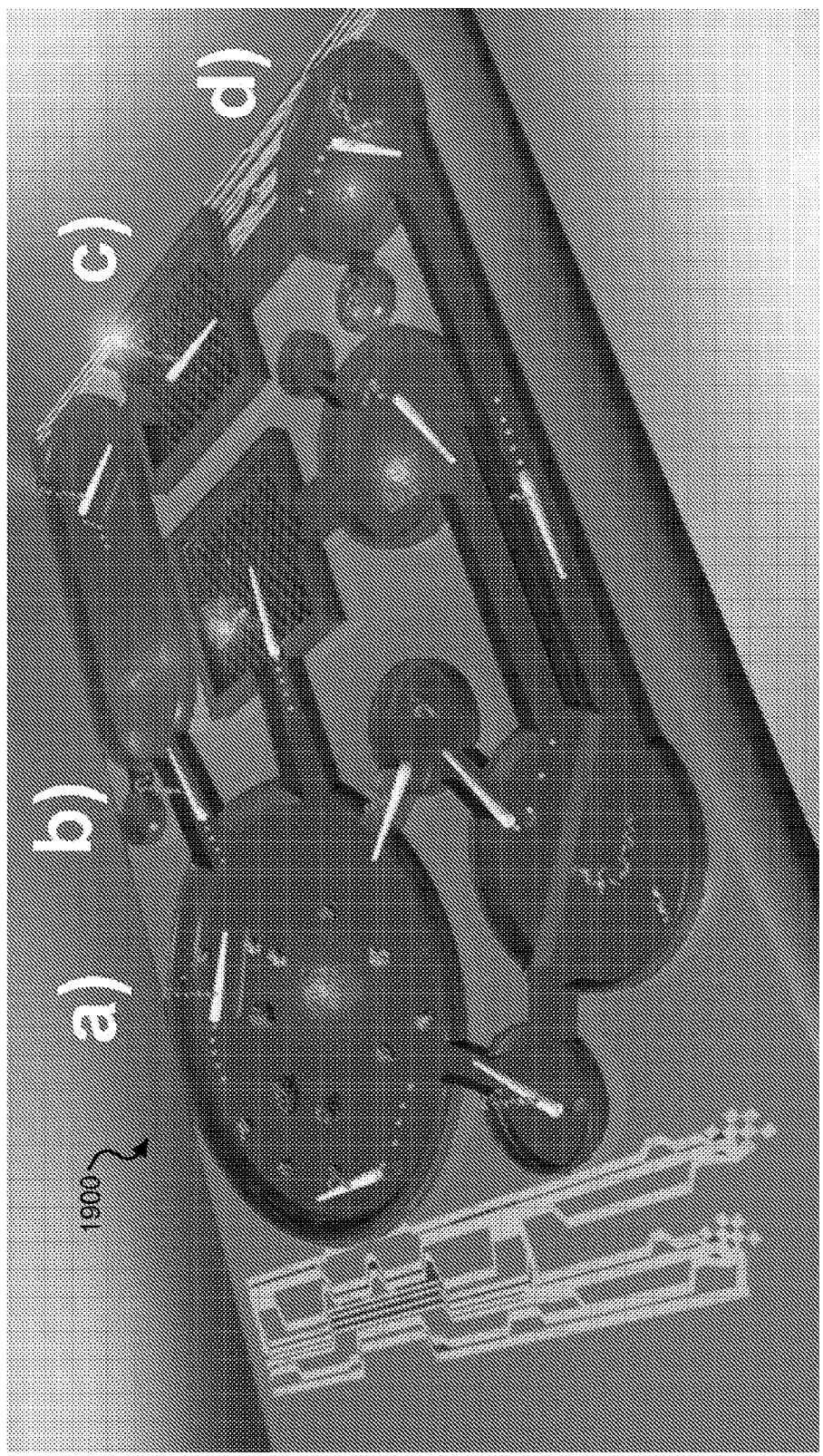
FIG. 19 shows an exemplary illustration of a lab-on-a-chip that employs the functionalized nano/micromachines to capture, isolate, and transport a target substance.

These exemplary microrockets can be implemented in devices and systems, e.g., biosensor devices such as lab-on-a-chip devices and systems with PCR based assay techniques, microscopy, and/or other characterization techniques, which can further allow unloading and characterization of the captured target. FIG. 19 shows an exemplary illustration of a lab-on-a-chip 1900 that employs the functionalized nano/micromachines that can self-propel in a fluid, e.g., using a fuel in the fluid to catalytically generate microbubbles that eject and result in a propulsion force, and capture, isolate and transport targeted biological entities. For example, the isolated biological entities captured on the modified-microrockets after the appropriate recognition reactions can be transported across microchannels of chip 1900, e.g., from a sample reservoir (a) to a transport/tagging reservoir (b), from the transport/tagging reservoir (b) to a detection reservoir (c), and from the detection reservoir (c) to a release reservoir (d). For example, multiple reservoirs can be clean reservoir for post analysis such as fluorescence microscopy, PCR, gel electrophoresis and sequencing, e.g., which can occur in the detection reservoir (c) and the release reservoir (d). For example, the functionalized nanomotors can be directed for the rapid and simple isolation, manipulation, preconcentration and detection of multiple desired biological targets on a single chip 1900. The exemplary ligand molecule-modified nanomotors can transfer the captured biomarkers or targets from the sample reservoir (a), containing the complex biological fluid, into the detection reservoir (c), which can include a pure buffer ideal for sensing. The captured analyte can undergo various manipulations and processes within different stations on its way from the sample reservoir (a) to the detection reservoir (b). The entire operation can be implemented without any bulk solution flow.

Exemplary isolation of biological entities using synthetic modified nanomotors can include to the use of other types of nano/micromotors like the fuel-independent ones (e.g., magnetically or electrically propelled) or to the use of different biological immobilized receptors and biomolecular interactions (e.g. peptides, lectins and carbohydrates). Exemplary engineered functionalized nanomotors can be guided from a raw sample reservoir along a microchip to a post-analysis reservoir using external guidance or along predefined tracks. The disclosed technology can include the isolation of biological markers (e.g., cells, proteins, nucleic acids, etc.) from a complex sample for sequential analysis, e.g., on a lab-on-chip device such as chip 1900. Additionally, the movement of the nano/microscale motor increases the solution convection thereby improving the diffusion of the target biomolecule, making for a quicker and more favorable the recognition reaction. In addition, this also helps to eliminate non-specific binding while on its way to a clean environment for subsequent analysis.

The exemplary nano-/micro-bio-machines can enable construction of nanometer-scale devices, e.g., nanobiosensors, nanofluidic systems, or nanomachines. For example, the disclosed nano/micromotors can be employed in a nano-bioactuator-based lab-on-a-chip system, e.g., that does not require external power or control. Such microchips can rely on the active transport of multiple functionalized nanomachines in a sample reservoir to induce numerous interactions, high capture efficiency and single-step isolation of the target analytes.

In another aspect, the disclosed technology can include isolating target proteins from complex biological samples based on an aptamer-modified self-propelled nano/microtube engine. For example, a thiolated thrombin or a mixed thrombin-ATP aptamer (e.g., prehybridized with a thiolated short DNA) can be co-assembled with mercaptohexanol onto the gold surface of these nano/microtube engines. Exemplary implementations performed showed rapid movement of the aptamer-modified microengine (e.g., also referred to as microtransporter) and highly selective and rapid capture of the target thrombin, e.g., with an effective discrimination against a large excess of nontarget proteins. Release of the captured thrombin can be triggered by the addition of ATP that can bind and displace the immobilized mixed thrombin-ATP aptamer, e.g., in 20 min. The rapid loading and unloading abilities demonstrated by these exemplary selective microtransporters can be implemented in complex matrixes such as human serum and plasma. The disclosed motion-driven protein isolation platform can be implemented in a variety of applications, e.g., bioanalytical chemistry based techniques on active transport of proteins and diverse diagnostic applications.

For example, isolation, separation, and purification of different proteins and peptides are necessary in bioscience and biotechnology. For example, the selective isolation of proteins from biological samples can be included in the diagnosis and treatment of various diseases. Yet, protein isolation can be challenging, e.g., because of the complex composition of many biological samples.

Examples are described of nano/micromachines-based techniques for isolating target proteins from complex biological samples, e.g., without preparatory and washing steps.

Figure 20:
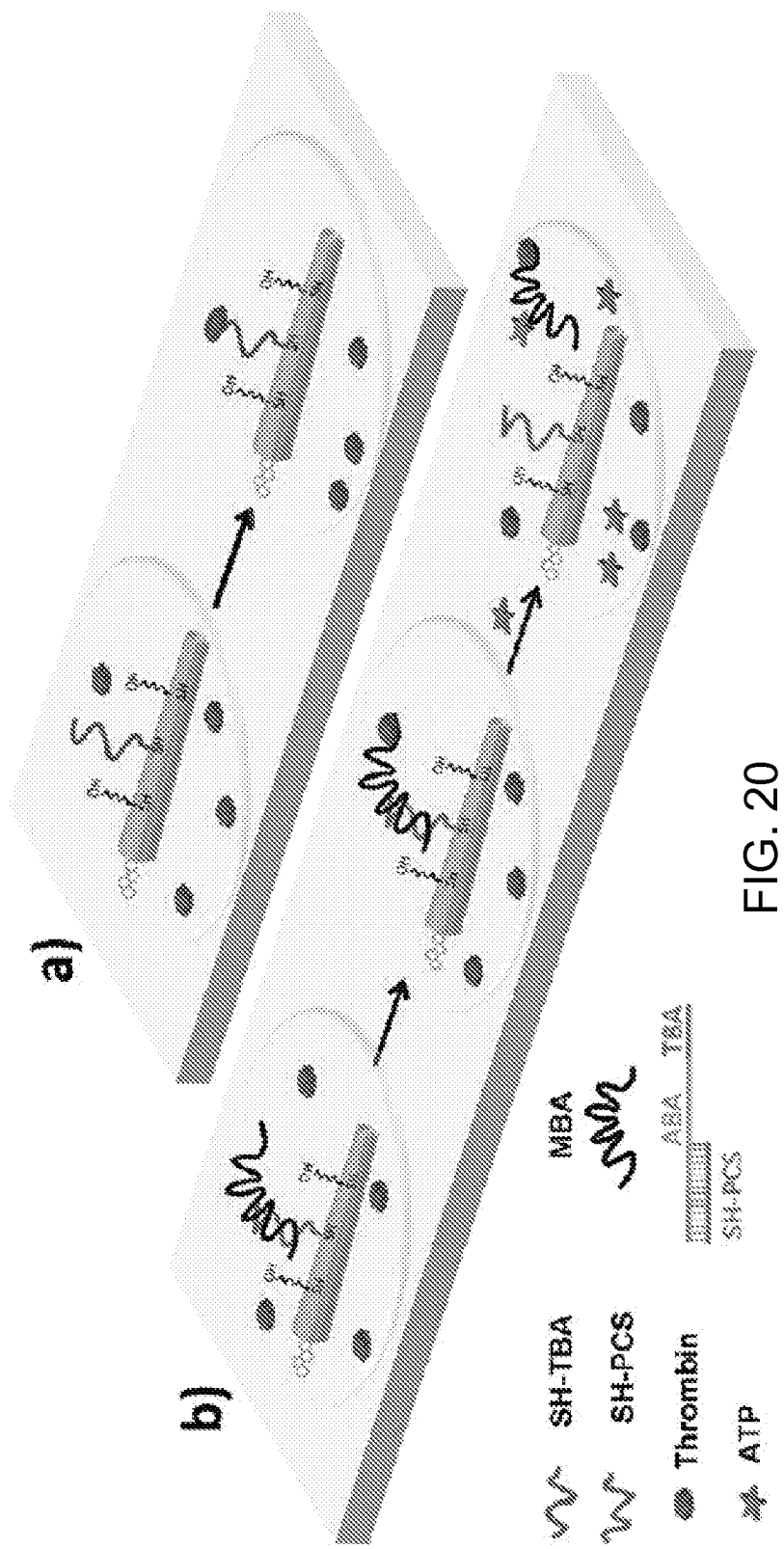
FIG. 20 shows an illustration demonstrating the selective pick-up, transport, and triggered release of target proteins based on aptamer-modified microengines.

For example, a nanomotor-enabled selective protein isolation was implemented by preparing the outer gold surface of microtube engines with aptamer receptors. Aptamers are artificially selected, functional oligonucleotides that represent attractive affinity reagents for protein isolation. For example, aptamers can bind to molecular targets with high specificity and affinity and exhibit several advantages over antibody receptors. This exemplary aptamer microtransporter technology is disclosed here, e.g., by the highly selective thrombin isolation from complex biological fluids such as serum or plasma. For example, exemplary microengines were functionalized by the self-assembly of a thiolated thrombin aptamer (SH-TBA) and mercaptohexanol (MCH) as "backfiller" onto its outer gold surface (as shown in FIG. 20). FIG. 20 shows an illustration demonstrating the selective pick-up, transport, and triggered release of target proteins based on aptamer-modified microengines. Shown in panel (a) is the exemplary selective pick-up and transport of a target protein from a raw biological sample by a TBA-modified microtransporter. Shown in panel (b) is the exemplary selective loading, transport, and release of the capture protein using a MBA-modified microtransporter. A detailed structure of the MBA is depicted at the left bottom of FIG. 20. The controlled modification of the microtransporter surface offers remarkable discrimination against a large excess of nontarget proteins and, along with the specific aptamer recognition, leads to the selective isolation of the target protein from complex samples. Exemplary use of artificial nanomachines as protein isolation platform can represent advancement toward protein analysis and other bioanalytical techniques.

Also demonstrated is the controlled (triggered) release of captured biological targets from a moving synthetic micromotor. For example, the disclosed technology includes functionalization the surface of the microtube engines with a mixed binding aptamer (MBA), containing both ATP (ABA) and α-thrombin (TBA) binding aptamers. The MBA was prehybridized to a short thiolated partially complementary oligonucleotide strand that is bound to the microengine's surface (SH-PCS, see bottom left part of FIG. 20). As illustrated in FIG. 20 panel (b), release of the captured thrombin from the moving MBA-modified microtransporter can be triggered by navigation in an ATP solution. For example, interaction with ATP induces a conformational change that releases the thrombin-MBA complex from the microengine surface, leaving on the surface only the SH-PCS. The capture and release capabilities of the new aptamer-functionalized microshuttles make them extremely attractive for developing microchip devices that isolate protein biomarkers from unprocessed samples and perform the pick-up, guided transport, and controlled release of target biomaterials, in general.

Exemplary reagents and solutions included the following. For example, 6-mercaptohexanol (MCH) and sodium cholate (NaCh) were acquired from Sigma-Aldrich. Bovine serum albumin (BSA), lysozyme from chicken egg white, thrombin from human plasma, human IgG, human serum (from human male AB plasma), plasma from human, KCl, Tris-HCl, $MgCl_2$, $CaCl_2$, ammonium sulfate, and NaCl were acquired from Sigma-Aldrich. Hydrogen peroxide (30% w/w) was acquired from Fisher Scientific. Streptavidin-coated fluorescence microspheres (210 nm mean diameter CP01F/8905, 10 mg of microspheres/mL, 1% solids w/v) were acquired by Bangs Laboratories Inc. Exemplary reagents were used without any further purification. Exemplary synthetic oligonucleotides used were acquired from Integrated DNA Technologies Inc. (San Diego, Calif.). Exemplary buffer solutions included the following: 50 mM Tris-HCl containing 140 mM NaCl, 1 mM $MgCl_2$, 5 mM KCl, and 1 mM $CaCl_2$, pH 7.4 (buffer 1), for TBA binding experiments; 25 mM Tris-HCl, 300 mM NaCl, pH 8.2 (buffer 2), for prehybridization of the SH-PCS with the MBA; 25 mM Tris-HCl, 100 mM NaCl, pH 8.2 (buffer 3), for the MBA binding experiments. Exemplary solutions of 2% (w/v) NaCh, 0.05 μM biotinylated detection aptamer (B-DA), thrombin, and 0.02% (w/v) fluorescence particles were prepared daily in the corresponding buffer solution (buffer 1 or 3, depending on the aptamer used for the experiment). For isolation experiments from spiked biological samples (human serum and plasma), the thrombin was prepared in the appropriate sample (previously diluted in the proper buffer if required). Exemplary chemicals were analytical-grade reagents used as received and prepared by dilution in 18.2 MΩ cm Milli-Q deionized (DI) water when not otherwise specified.

Exemplary microtransporters fabrication techniques were performed using techniques previously described. A thin (~60 nm) gold layer was sputtered onto the rolled-up microtubes to facilitate the surface functionalization with the mixed self-assembly monolayer (SAM) described herein. For example, prehybridization of the SH-PCS with the MBA included the following. For example, a mixture of 1.9 μM SH-PCS and 2.2 μM MBA (in buffer 2) was heated and kept at 90° C. for 5 min. The solution was then slowly cooled up to room temperature (around 30 min). The external gold surface of the microtransporters was modified by an overnight immersion in a 10 µMSH-TBA (in buffer 1) or the SH-PCS/MBA prehybridized solution prepared as specified in the previous section. For example, after washing with the appropriate buffer, the modified microtransporters were post-treated with a 0.1 mM MCH solution (also in the corresponding buffer) for 10 min to obtain the corresponding mixed SAMs. Finally, they were washed for 60 s with buffer, entirely detached from substrates by carefully scratching with a micropipette tip, and placed in the corresponding binding buffer. Exemplary incubation steps were carried out at room temperature.

Exemplary thrombin isolation and detection protocol involved a sandwich-type assay format in which the thrombin is captured between the microtransporter surface-chemisorbed capture aptamer (TBA or MBA) and the B-DA. Once the sandwich is formed the labeling of the B-DA with the streptavidin-fluorescence particle tags confirms the presence of thrombin attached to the aptamer-modified microtransporters. For example, for isolation of thrombin, a mixture of the 3 µL of aptamer-modified microtransporters suspension, 2 µL of 2% (w/v) NaCh, 1.5 µL of 30% (w/w) H2O2, and 3 µL of thrombin solutions (in the appropriate binding buffer or in the biological sample under study) was dropped onto a freshly cleaned glass slide. For example, the modified microtransporters were allowed to move 10 min in this solution to capture the protein, after which 3 µL of 0.05 µM B-DA solution was added, and the modified microtransporters were allowed to move in this solution for additional 10 min. In the last step, for example, a 3 µL of 0.02% (w/v) fluorescence particles suspension was added and the microtransporters carrying the affinity complex (SH-TBA-thrombin-B-DA) were allowed to move randomly in the above solution during the desired time. Exemplary data was recorded and analyzed using equipment and techniques previously described. For example, an estimation of the captured affinity complex-tagged particles coverage on the microtransporters was obtained by analyzing the corresponding time-lapse images using the ImageJ software.

Exemplary implementations evaluating the selectivity data included control experiments were carried using 3 µL of the corresponding binding buffers (or samples under study) without target protein, or with solutions of nontarget proteins (BSA, human IgG, and lysozyme) alone or mixed with the target protein, prepared in the corresponding binding buffer. Exemplary procedures were carried out at room temperature.

Exemplary fibrinogen was precipitated from plasma (but not from serum) before the addition of thrombin in the preparation of spiked samples. An amount of 250 µL of plasma was treated with 1250 µL of 2 M ammonium sulfate and 1000 µL of 0.1 M NaCl aqueous solutions. The solution was mixed for 3-4 min and then centrifuged at 12,000 rpm during 4 min. The non-desalted supernatant was spiked with the desired thrombin concentration. For example, to test the performance of the aptamer-based microengines in these complex matrixes 100 nM thrombin standard solutions were added to the untreated serum or pretreated plasma samples, respectively.

Exemplary aliquots of 3 µL of the MBA-modified microtransporters suspension, 2 µL of 2% (w/v) NaCh, 1.50 µL of 30% (w/w) $H_2O_2$, and 3 µL of 200 nM thrombin solutions (in the appropriate binding buffer) were dropped on a freshly cleaned glass slide. The exemplary modified microtransporters were allowed to move 10 min in this solution to capture the protein, after which two different protocols were tested. On one hand, 3 µL of B-DA and 3 µL of fluorescence particles were allowed to react with the previous mixture during 10 min each, after which 3 µL of 0.01 M ATP solution was added, and surface coverage was checked after 20 min. Alternately, 3 µL of 0.01 M ATP solution was first added to the solution, and the microtransporters were allowed to navigate during 20 min to release the bound protein. After that, the thrombin that remains attached to the microtransporters was labeled using the previously described B-DA and the fluorescence particles sequential incubation steps, and the surface coverage was then estimated.

Figure 21:
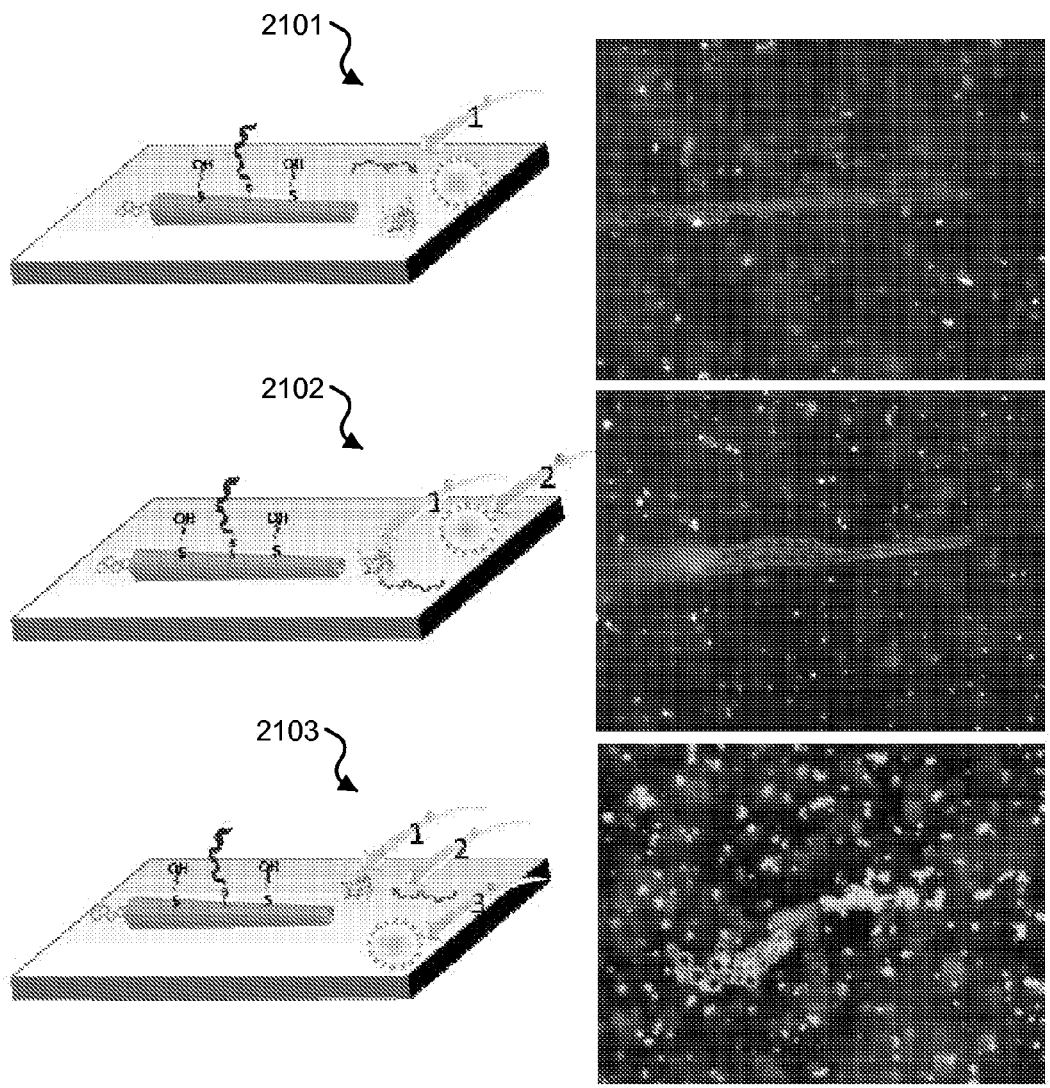
FIG. 21 shows an illustration demonstrating the isolation efficiency observed when mixing thrombin, biotinylated detection aptamer (B-DA), and particles in one, two, and three step processes.

The aptamer-functionalized microtransporters can readily move around within a biological sample (containing fuel) and can recognize and interact with the target thrombin protein (e.g., as illustrated in FIG. 20 panel (a)). For example, the target binding event included B-DA that binds to subsequently added streptavidin-coated fluorescent nanoparticle tags, forming a "TBA-thrombin-B-DA" sandwich on the moving micro-shuttles. Exemplary implementations reveal that the incubation of the modified micro-engines in solutions containing thrombin, the B-DA, and the fluorescent particles can occur separately in a stepwise fashion, to minimize hindrance of the thrombin recognition event. For example, FIG. 21 shows an illustration comparing of the isolation efficiency observed when mixing thrombin, B-DA, and particles in one step (shown in panel and image 2101), B-DA and thrombin in one step and adding later the particles (shown in panel and image 2102), and thrombin, B-DA and particles in a sequential 3-step procedure (shown in panel and image 2103). The exemplary number of steps are indicated as 1, 2 and 3.

Figure 22:
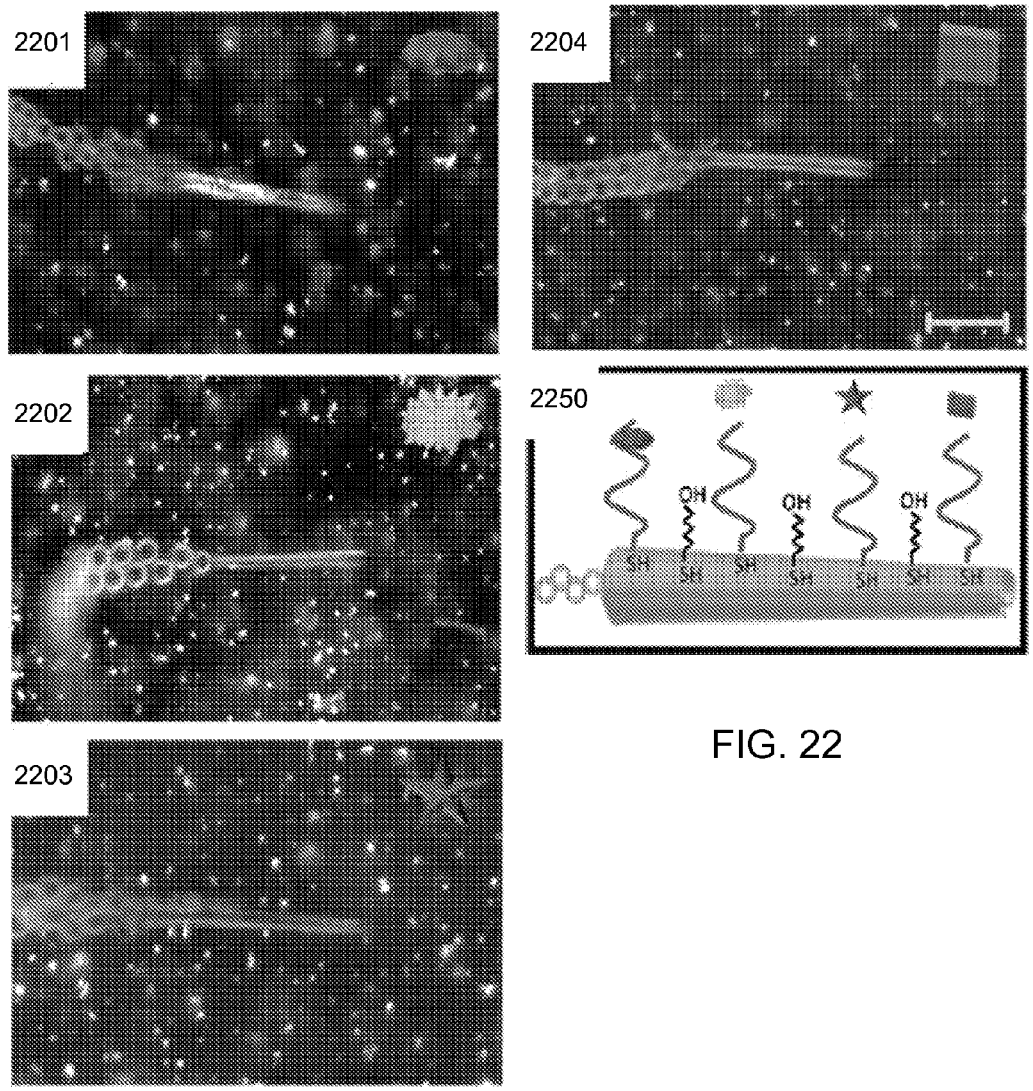
FIG. 22 shows exemplary images and an illustration of the selective isolation of target proteins using exemplary aptamer-modified microengines.

For example, specific binding can be a requirement for the new aptamer-based nanomotor isolation platform. To evaluate the binding specificity of the aptamer-modified microtransporters toward the target thrombin protein, various exemplary non-target proteins were used (at 50-fold excess) as negative controls. The optical microscope images of FIG. 22 can show the high specificity of the dynamic aptamer-thrombin interaction using different protein solutions. For example, FIG. 22 shows an image 2201 demonstrating thrombin (20 nM) vs. large (50-fold) excess of nonspecific proteins (1000 nM), an image 2202 demonstrating thrombin (20 nM) vs. large (50-fold) excess of BSA (1000 nM), an image 2203 demonstrating thrombin (20 nM) vs. large (50-fold) excess of human IgG (1000 nM), and an image 2204 demonstrating thrombin (20 nM) vs. large (50-fold) excess of lysozyme (1000 nM). The exemplary modified microtransporters were navigated for 10 min in solutions containing either the protein under study or the respective non-targeting proteins. FIG. 22 also shows an illustration 2250 depicting the observed selectivity results where only the target protein is captured by the TBA-modified microtransporters. Exemplary fuel conditions included 3% (w/w) H2O2, 0.3% (w/v) NaCh. A substantial coverage of the microengine surface is observed in the target protein solution (image 2201). In contrast, only negligible binding is indicated for the large excess of the nontarget BSA, IgG, and lysozyme (images 2202, 2203, 2204, and 2205, respectively). The exemplary data also illustrates the efficient propulsion of the aptamer-modified microengine (at a high speed of 125 µm/s). For example, the capture of the thrombin target also has a negligible effect upon the propulsion efficiency.

Figure 23:
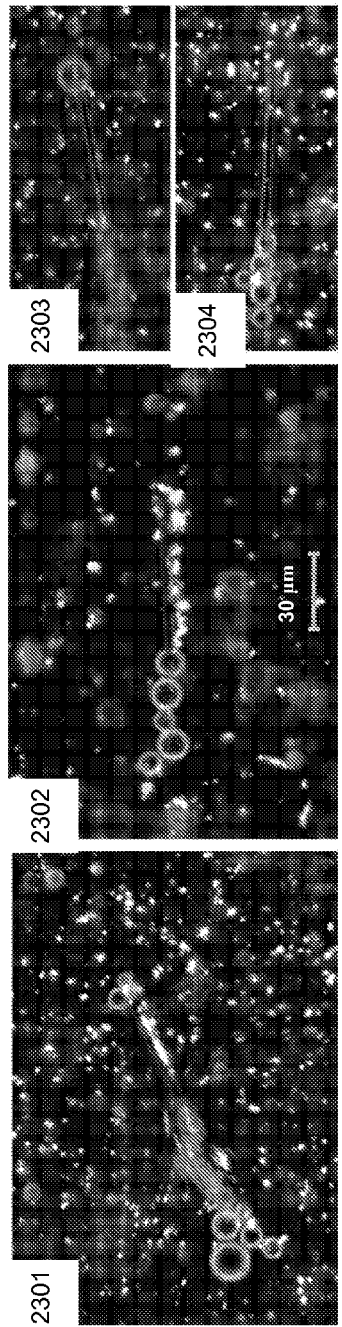
FIG. 23 shows exemplary images demonstrating aptamer-modified microtransporters functionality in different compositions of these complex biological fluids.

The exemplary utility of the disclosed aptamer-functionalized nano/microengine technology was evaluated, for example, by the ability of the aptamer-modified microtransporters to recognize the target protein in a complex media, e.g., such as human serum and plasma samples. FIG. 23 shows exemplary images 2301, 2302, 2303, and 2304 showing aptamer-modified microtransporters functionality in different compositions of these complex biological fluids. FIG. 23 shows the TBA-modified microtransporters in 25% human serum solutions spiked with 100 nM thrombin (image 2301) and without 100 nM thrombin (image 2303) and in 10% human plasma solutions pretreated with 100 nM thrombin (image 2302) and untreated with 500 nM thrombin (image 2304). For example, the plasma sample was shown to lead to a higher bubble size and lower speed due to the presence of coagulation factors and its high viscosity. The efficient propulsion of the exemplary modified microtransporters in these complex biological samples (with speeds of 90 and 70 µm/s, respectively) allows for their prolonged movement and direct isolation of thrombin without tedious sample processing steps. The exemplary implementation demonstrated the ability of microengines to efficiently capture the target protein from biological samples, e.g., using 25% diluted human serum (raw or spiked with thrombin) and 10% plasma samples spiked with thrombin (with or without a standardized pretreatment for quantitative fibrinogen precipitation). The exemplary data confirms the feasibility of the new aptamer-based microtransporters to propel effectively and detect selectively trace levels of proteins in complex biological samples, e.g., human serum and plasma samples.

Exemplary implementations were performed to evaluate ATP-assisted release of the captured thrombin. For example, to facilitate the release of the captured thrombin, the TBA receptor was replaced with a MBA receptor. For example, according to its structural design (bottom left portion of FIG. 20), when only thrombin is present in the solution, the MBA-modified microtransporters can capture the thrombin and transport it toward the desired site. However, for example, when ATP is present, it can interact with the ATP-binding aptamer portion (ABA), overlapped by the section of the MBA hybridized to SH-PCS, and draws the thrombin-MBA complex away from the modified microtransporter surface. This can leave only the SH-PCS attached to the microtransporters resulting in the full release of the thrombin-aptamer complex (as shown in FIG. 20 panel (b)).

Figure 24:
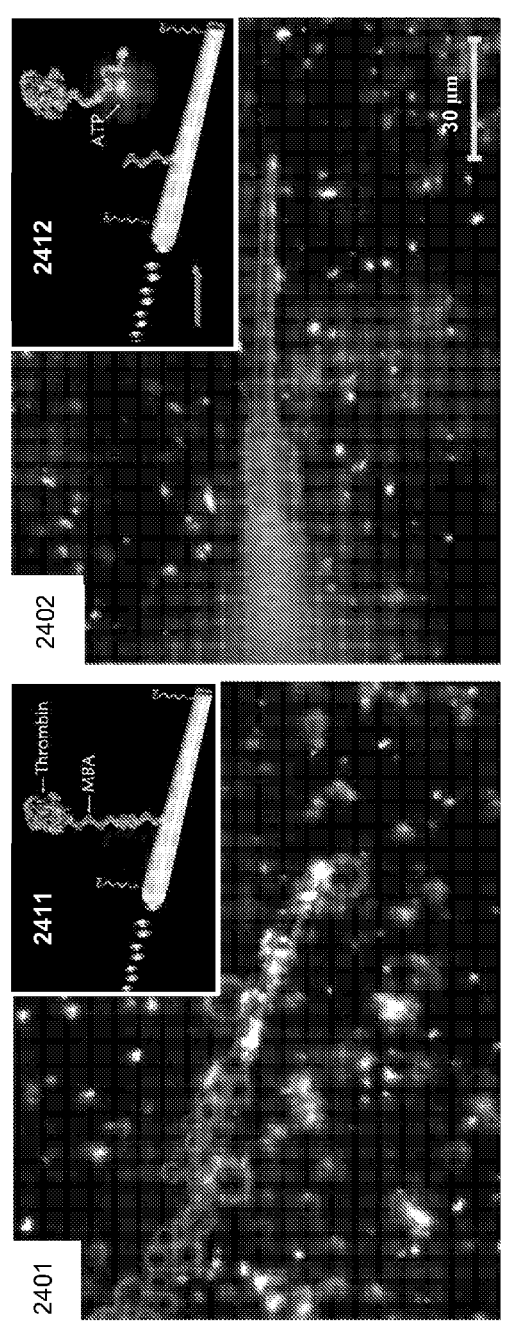
FIG. 24 shows images and schematics demonstrating exemplary data of the mixed binding aptamer (MBA)-modified microtransporters in the absence and presence of ATP trigger molecules.

The exemplary implementation included incubatation of the microtransporters (containing the MBA-thrombin complex) in an ATP solution for a fixed time (e.g., last step in FIG. 20 panel (b)) before labeling the attached thrombin with the B-DA and the fluorescence particles in the described manner. FIG. 24 shows images 2401 and 2402 showing exemplary data of the MBA-modified microtransporters after target binding (e.g., indicated by the presence of bound fluorescent particles) and incubation in a buffer solution in the absence (image 2401) and in the presence of ATP trigger molecule (0.01 M) (image 2402). Exemplary schematic 2411 illustrates an exemplary thrombin target bound to the MBA-modified microtransporter. Exemplary schematic 2412 illustrates the release of the exemplary thrombin target by an ATP trigger molecule. Incubation in the ATP solution resulted in a very small fluorescence coverage of only 9% on average compared to the 74% coverage observed in a control experiment without ATP. These exemplary results demonstrate the efficient release of the thrombin-MBA complex after 20 min of movement in the 0.01 M ATP solution. The exemplary implementations demonstrate that the labeling of the captured thrombin (with the B-DA and fluorescence spheres) hinders the ATP interaction with the MBA aptamer, thereby requiring a post release labeling approach. With the use of this approach, the drop-off of the protein cargo into the solution is clearly indicated when comparing the fluorescence coverage observed after navigation in a buffer solution, with and without the ATP trigger molecule.

In another aspect, the disclosed technology can include template-based self-propelled gold/nickel/polyaniline/platinum (Au/Ni/PANI/Pt) nano/microtubular engines, functionalized with the Concanavalin A (ConA) lectin bioreceptor. Exemplary implementations of the lectin-functionalized nano/microengines were performed and demonstrated rapid, real-time isolation of *Escherichia coli* (*E. coli*) bacteria from fuel-enhanced environmental, food, and clinical samples. The exemplary multifunctional lectin-functionalized nano/microtube engines can combine the selective capture of *E. coli* with the uptake of polymeric drug-carrier particles to provide motion-based theranostics devices, systems, and techniques. For example, triggered release of the captured bacteria was demonstrated in exemplary implementations by movement through a low-pH glycine-based dissociation solution. The smaller size of the exemplary polymer-metal nano/microengines can offer convenient, direct, and label-free optical visualization of the captured bacteria and discrimination against non-target cells.

Examples are described of nano/micromachines-based techniques for isolating pathogenic bacteria from peroxide-fuel containing clinical, environmental, and food samples, involving the movement of lectin-functionalized microengines. For example, the disclosed nano/micromachines can be developed to smaller (e.g., 8 µm) and highly efficient nano/microtube engines using mass-produced techniques through an exemplary low-cost membrane template electrodeposition technique. For example, the exemplary membrane template electrodeposition technique can fabricate nano/micromachines capable of speeds (e.g., >300 body lengths/s) and with low fuel requirements (e.g., down to 0.2%).

Lectins are glycoproteins that can recognize carbohydrate constituents of bacterial surface, e.g., via selective binding to cell-wall mono- and oligosaccharide components. For example, ConA is a lectin extracted from *Canavalia ensiformis* and is a mannose- and glucose-binding protein that is capable of recognizing specific terminal carbohydrates of Gram-negative bacteria such as the *E. coli* surface polysaccharides.

Figure 25A:
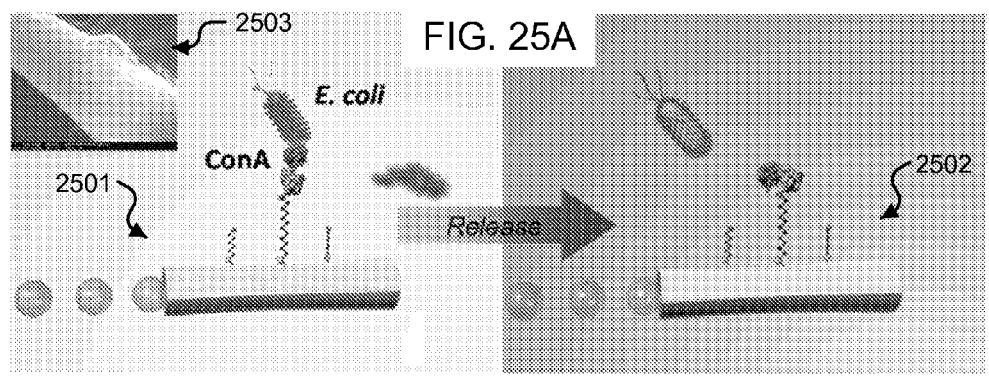
FIG. 25A shows schematic illustrations of a nanoscale bacteria isolation technique of that utilizes the movement of lectin-functionalized microengines.

An image 2501 in FIG. 25A shows exemplary schematic illustrations of a nanoscale bacteria isolation technique of the disclosed technology that utilizes the movement of ConA-functionalized microengines to scour, interact, and isolate pathogenic bacteria from distinct complex samples. For example, using the described lectin-functionalized nano/microengines, a bacterial target can be further unloaded through controlled release of the captured bacteria from the moving synthetic nano/microengine (as shown in FIG. 25A image 2502). The exemplary triggered release can be accomplished, e.g., by using a low-pH glycine solution that is able to dissociate the lectin-bacteria complex (as shown in image 2502 of FIG. 25B). For example, image 2501 exemplifies that upon encountering the cells, the ConA-functionalized microengines can recognize the *E. coli* cell walls by O-antigen structure binding, e.g., allowing for selective pick-up and transport. The exemplary inset 2503 shown in FIG. 25A shows an exemplary SEM image of a portion of a ConA-modified microengine loaded with an *E. coli* cell. The image 2502 shows the release of the capture bacteria, e.g., by navigation in a 10 mM glycine solution (e.g., pH 2.5). For example, the ability of the disclosed nano/microengines can also simultaneously capture and transport both the target bacteria as well as polymeric drug-carrier spheres, e.g., using the lectin and magnetic interactions, respectively. This exemplary dual action, coupling the *E. coli* isolation with "on-the-spot" therapeutic action, can be implemented as a theranostic tool (e.g., "identify and eradicate"), e.g., based on the disclosed abilities of the nano/micromachine platforms.

Figure 25B:
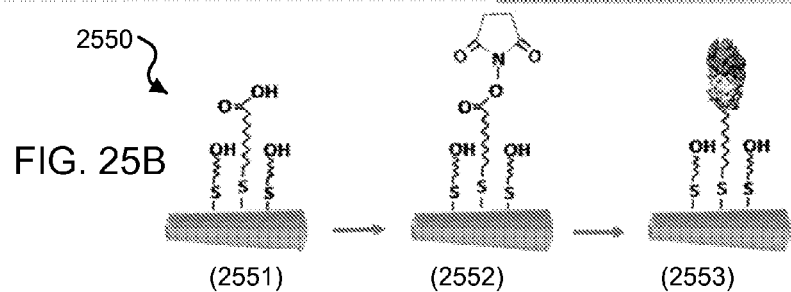
FIG. 25B shows schematic illustrations of a functionalization scheme involving the self-assembly of alkanethiols and subsequent conjugation of the lectin receptor.

Exemplary fabrication of the nano/microengines can include a template-based electrodeposition of a polyaniline (PANI)/Pt bilayer microtube and e-beam vapor deposition of outer Ni/Au layers. For example, the intermediate-outer layer can include nickel, iron, or other magnetic materials in the layer to be used for an external steering (e.g., by magnetic navigation) of the self-propelled nano/microengine. For example, the intermediate-outer layer can include gold, silver, and other materials for surface functionalization. For example, FIG. 25B show an illustration 2550 that demonstrates a functionalization scheme involving the self-assembly of alkanethiols and subsequent conjugation of the lectin receptor.

The exemplary template fabrication process can produce, for example, 8 µm long microtube engines. For example, relative similar dimensions of the microengine and the target bacteria (e.g., which can be ~2 µm long×0.5 µm in diameter) can permit convenient real-time optical visualization of the isolation process without the need for additional labeling. For example, by varying the membrane pore size and deposition time, the exemplary microengine's aspect ratio can be tailored for meeting the needs of specific target bacteria detection paradigms. The template-prepared microengines can be propelled efficiently in different media via the expulsion of oxygen bubbles generated from the catalytic oxidation of hydrogen peroxide fuel at the inner Pt layer. The high speed of the template-prepared PANI/Pt bilayer microtube engines can achieve speeds (e.g., 300 µm/s) larger than those PANI/Pt microtube engines that include the outer Ni/Au layers (e.g., speeds shown to be ~150 µm/s in some exemplary implementations).

The exemplary nano/microengine can be functionalized for efficient lectin-bacteria interaction and locomotion using an exemplary functionalization technique herein. As illustrated in image 2550 of FIG. 25B, functionalization can be accomplished by conjugating the lectin to the outer gold surface of the microengines via a self-assembled monolayer (SAM). For example, a mixture of 11-mercaptoundecanoic acid (MUA) and 6-mercaptohexanol (MCH) can be used to create the binary SAM, as shown in schematic 2551. An exemplary 1-ethyl-3-(3-dimethylaminopropyl) carbodiimide (EDC)/N-hydroxysuccinimide (NHS) chemistry can be used to activate the MUA carboxyl-terminated groups for conjugation with ConA, as shown in schematic 2552. For example, to promote favorable target accessibility while minimizing nonspecific adsorption, the binary SAM can be prepared using alkanethiol concentrations of 0.25 mM MUA and 0.75 mM MCH. For example, relatively low thiol concentrations can ensure minimal poisoning of the inner catalytic platinum surface and hence a high catalytic activity. For example, the exemplary surface modification of the Au/Ni/PANI/Pt microtubular engines can move at a sufficient speed (e.g., 80 µm/s.) to perform cellular towing tasks. For example, as shown in schematic 2553, the lectin receptor was immobilized via NHS/EDC coupling using a binding buffer (BB) solution containing 9 mg/mL of ConA. This exemplary step did not affect the microengine speed.

Figure 26:
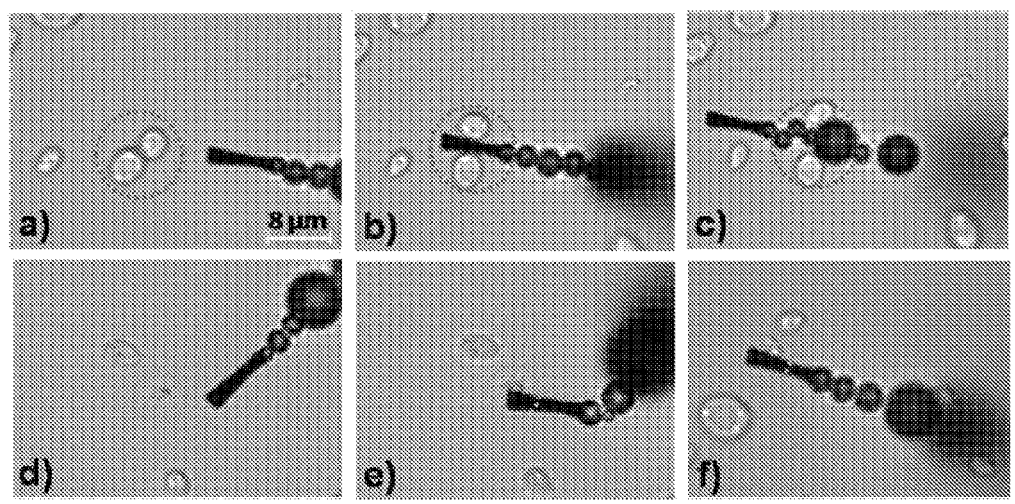
FIG. 26 shows exemplary images demonstrating selective binding and transport of the bacteria to lectin-functionalized microengines.

Exemplary implementations were performed to demonstrate the specific binding of the ConA-modified microengines to *E. coli*, e.g., in inoculated human urine samples. For example, these exemplary urine samples were inoculated with *E. coli* target bacteria along with a 5-fold excess of a 'control' bacteria *Saccharomyces cerevisiae* (*S. cerevisiae*), e.g., a species of yeast frequently responsible for yeast infections and UTIs. FIG. 26 shows exemplary images that demonstrate the selective binding and transport of the rod-shaped (~2 µm length) gram-negative *E. coli* bacteria (delineated by green dotted circles). In contrast, the modified microengine did not capture the round-shaped *S. cerevisiae* cells (e.g., ~5 µm in diameter) even when multiple contacts occur (delineated by red dotted circles), shown in FIG. 26 images (a), (b), and (c)). For example, the distinct size (~2 µm vs. 5 µm) and shape (rod vs. round) of the target *E. coli* and control *S. cerevisiae*, respectively, can allow clear optical visualization and discrimination between the target and nontarget cells during the motor navigation. This selective and rapid capture mechanism can be attributed to the nearly instantaneous recognition of the sugar moieties on the bacterial cell wall by the lectin-modified microengine, as shown in FIG. 26 images (d), (e), and (f). Indeed, the multivalent binding of ConA to the O-antigen *E. coli* surface favors strong adhesion of *E. coli* to the ConA-modified microengine surface.

The reproducibility of the new motion-based isolation was investigated by using five different batches of ConA-modified microengines following identical processing steps. The results (not shown) demonstrated very small (~5%) differences in the bacteria capture efficiency among different batches of modified microengines, demonstrating the reliability of their fabrication, modification, and movement processes. While lectin-bacteria binding often requires long (30-60 min) incubation times, 30, 39 the microengine-induced localized convection appears to dramatically accelerate the binding process. Short contact times with the target bacteria (on the order of seconds) are thus sufficient for its effective capture. The new microengine platform thus presents a unique approach for meeting the need for rapid, direct, and real time isolation of biological agents.

Figure 27:
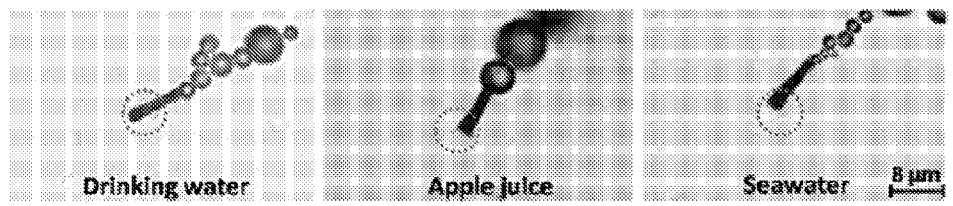
FIG. 27 shows exemplary images demonstrating the functionalized microengines "on the fly" capture of target bacteria in samples such as drinking water, juice, and salt water.

The exemplary utility of the disclosed microengine approach toward diverse applications was exemplified by the ability of the lectin-modified microengines to recognize the target bacteria in different fuel-enhanced and *E-coli*-inoculated real samples, e.g., common beverages such as drinking water an juice and environmental matrices such as sea water. For example, FIG. 27 shows exemplary images that illustrate that the functionalized microengines display an immediate "on the fly" *E. coli* capture upon contacting the target bacteria in real samples such as drinking water, juice, and salt water (e.g., sea water). For example, a successful pick-up rate (during the first engine-cell contact) of nearly 90% (n=50) has been observed in the three exemplary tested matrices of FIG. 27. Overall, the results of FIGS. 26 and 27 demonstrate the ability of the modified microengines to pick-up bacteria in the presence of diverse conditions, different environments, and matrix effects, e.g., low and high sugar concentrations (e.g., such as in drinking water and apple juice, respectively) as well as high salt (e.g., such as seawater and urine) environments.

The interaction between the bacterial cell and the ConA-modified microengines is not only highly selective but also very robust. For example, a drag force associated with the motion of the exemplary modified microengines is sufficient to remove a bacterial cell firmly fixated to the glass slide, e.g., showing a strong lectin/bacteria interaction and the high towing capacity of the lectin-modified microengines.

Figure 28:
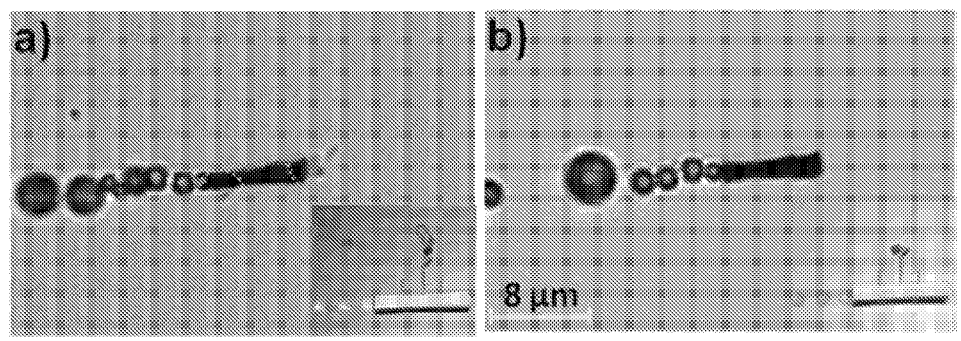
FIG. 28 shows exemplary images demonstrating the lectin-modified microengines before and after navigation in a dissociation solution.

Exemplary implementations were performed to evaluate the ability to isolate and unload target bacteria for identifying pathogenic bacteria serotypes. For example, to facilitate the release of the captured bacteria, the loaded ConA-modified microengines were moved through a low-pH glycine-based dissociation solution that disrupts the sugar-lectin complex, e.g., illustrated in image 2502 of FIG. 25A. FIG. 28 shows exemplary images demonstrating the lectin-modified microengines before (image (a)) and after (image (b)) 20 min navigation in a dissociation solution. For example, the prolonged continuous movement is observed without replenishing the fuel. The multiple bacteria confined to the moving microengine are shown to be released from its surface after movement in the low-pH glycine-based dissociation solution. For example, the efficient removal of the captured bacteria can be attributed to the unfolding of ConA in this low pH-solution, thereby dissociating the sugar-lectin complex and releasing the captured bacteria for subsequent reuse. The exemplary unfolding of the immobilized bioreceptor in this low-pH solution is supported also by the inability of the ConA-modified microengines to capture target bacteria in this medium while contacting it multiple times.

Figure 29:
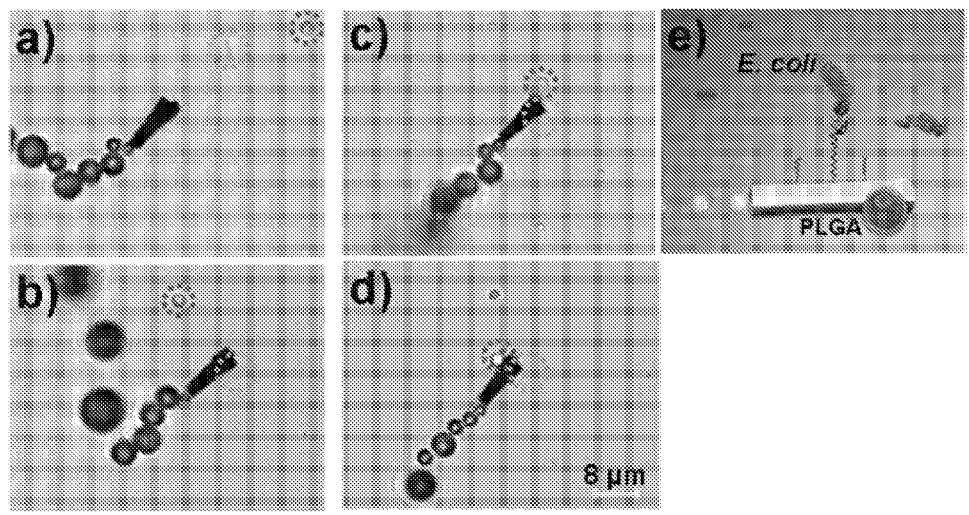
FIG. 29 shows exemplary images and an illustration of the dual capture and transport capabilities of the lectin-modified microengines.

Exemplary implementations were performed to evaluate the feasibility of lectin-modified microengines to perform multiple tasks. For example, the lectin-modified nano/microengines can be combined with exemplary devices and systems to target bacteria cells, e.g., with simultaneous transport of common therapeutic polymeric particles. For example, a drug carrier microspheres, poly D,L-lactic-co-glycolic acid (PLGA) microparticles, containing magnetic iron-oxide nanoparticles, were employed to demonstrate this dual capture and transport functionality. For example, FIG. 29 shows exemplary images and an illustration of the dual capture and transport of *E. coli* and PLGA drug-carrier particle. Images (a) and (b) in FIG. 29 shows the ConA-modified microengine identifying and capturing a noxious bacteria (e.g., *E. coli*), and images (c) and (d) show the ConA-modified microengine next capturing the magnetic polymeric drug carrier (along with the *E. coli*) and transporting both cargos at the same time. FIG. 29 demonstrates the multifunctionality of the modified-microengines for applications including disease diagnosis and treatment or water and food quality control.

Various implementations have been described for exemplary modified template-prepared nano/microengines. In some examples, a lectin-modified nano/microengine can include capabilities for autonomous loading, directional transport, and bacterial unloading (e.g., catch and release), as well as their subsequent reuse, e.g., also including efficient and simultaneous transport of drug nanocarriers. This exemplary ability to perform simultaneously bacteria isolation and directed drug-delivery can be incorporated in miniaturized theranostics microsystems, integrating dual capture of target species, and transporting and releasing target species in a controlled fashion within spatially separated zones. The incorporation of the disclosed microengine-based bacterial isolation techniques, e.g., into microchannel networks, can produce microchip operations involving real-time isolation of specific bacteria, and subsequent bacteria lysis and unequivocally identification (e.g., by 16S rRNA gene analysis), e.g., down to the single-cell level. Exemplary applications of the lectin-modified hybrid microengines can include food and water safety, infectious disease diagnostics, biodefense, and clinical therapy treatments.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

We claim:

1. A device that self propels in a fuel fluid, comprising:
a tube structured to include a first opening and a second opening that are on opposite ends of the tube, and a tube body connecting the first and second openings and having a cross section spatially reducing in size along a longitudinal direction from the first opening to the second opening, the tube including a layered wall which includes an inner layer having a catalyst material that is reactive with a fuel fluid to produce bubbles exiting the tube from the first opening to propel the tube to move in the fuel fluid and an external layer formed of a material capable of being functionalized; and
a molecular layer functionalized onto the external layer of the tube and structured to attach to a targeted molecule in the fuel fluid.

2. The device of claim 1, wherein the layered wall of the tube further includes a steering structure that interacts with an external control to steer a pointing direction of the tube while being propelled by the bubbles.

3. The device of claim 2, wherein the steering structure includes a magnetic material that interacts with an external magnetic field to magnetically steer the pointing direction of the tube.

4. The device of claim 1, wherein the layered wall of the tube includes an intermediate layer on which the external layer is formed.

5. The device of claim 4, wherein the intermediate layer includes a polymer material.

6. The device of claim 5, wherein the polymer material is polyaniline.

7. The device of claim 1, wherein the catalyst material includes platinum.

8. The device of claim 1, wherein the material capable of being functionalized includes at least one of gold or silver.

9. The device of claim 1, wherein the molecular layer includes a self-assembled monolayer.

10. The device of claim 1, wherein the tube has a diameter between 280 nm to 1 mm.

11. The device of claim 1, wherein the tube has a diameter of substantially 50 μm for the first opening and a diameter of substantially 30 μm for the second opening.

12. The device of claim 1, wherein the fuel fluid includes at least one of water, juice, humour, bile, blood, cerebrospinal, intracellular, extracellular, digestive, lymphatic, mucus, peritoneal, pleural, saliva, sebum, semen, sweat, tears, urine, vaginal, or bacteria-containing fluid.

13. The device of claim 1, wherein the molecular layer includes a ligand molecule having an affinity to the targeted molecule.

14. The device of claim 13, wherein the ligand molecule is an antibody and the targeted molecule includes an antigen having a binding affinity to the antibody, the antigen located on a tumor cell that attaches to the tube at the ligand molecule.

15. The device of claim 13, wherein the ligand molecule is at least one of a single-stranded oligonucleotide, aptamer, lectin, or peptide.

16. The device of claim 13, wherein the ligand molecule is a single-stranded oligonucleotide having an affinity to a complimentary binding site of a target nucleic acid.

17. The device of claim 13, wherein the ligand molecule is an aptamer having an affinity to a protein-based molecule.

18. The device of claim 13, wherein the ligand molecule is a lectin having an affinity to a receptor site of a bacteria cell.

19. A device for transporting a target substance in a fluid, comprising:
a tube formed of two or more layers with a first opening having a smaller diameter than a second opening of the tube, wherein the two or more layers include an outer layer having a modifiable material capable of being functionalized; and
a molecular layer formed on the modifiable material and including a ligand molecule, the molecular layer structured to attach a target substance having a receptor site with a binding affinity to the ligand molecule,
wherein the two or more layers include an inner layer including a catalytic material that reacts with a fuel in a fluid to produce bubbles exiting the tube from the second opening to propel the tube to move in the fluid, the tube attaching the target substance during movement at a first location in the fluid and transporting the target substance to a second location in the fluid.

20. The device of claim 19, wherein the tube has a diameter between 280 nm to 1 mm.

21. The device of claim 19, wherein the tube has a diameter of substantially 50 μm for the first opening and a diameter of substantially 30 μm for the second opening.

22. The device of claim 19, wherein the fluid includes at least one of water, juice, humour, bile, blood, cerebrospinal, intracellular, extracellular, digestive, lymphatic, mucus, peritoneal, pleural, saliva, sebum, semen, sweat, tears, urine, vaginal, or bacteria-containing fluid.

23. The device of claim 19, wherein the fluid includes serum.

24. The device of claim 19, wherein the fuel includes a peroxide.

25. The device of claim 19, wherein the catalytic material includes platinum.

26. The device of claim 19, wherein the modifiable material includes at least one of gold or silver.

27. The device of claim 19, wherein the molecular layer includes a self-assembled monolayer.

28. The device of claim 19, wherein the tube further comprises an intermediate material between the inner layer and the outer layer.

29. The device of claim 28, wherein the intermediate material is a magnetic material that enables magnetically-controlled steering of the tube.

30. The device of claim 29, wherein the magnetic material includes at least one of nickel or iron.

31. The device of claim 19, wherein the ligand molecule is an antibody and the receptor site is in an antigen having the binding affinity to the antibody, the antigen located on a tumor cell that attaches to the tube at the ligand molecule.

32. The device of claim 19, wherein the ligand molecule is at least one of a single-stranded oligonucleotide, aptamer, lectin, or peptide.

33. The device of claim 19, wherein the ligand molecule is a single-stranded oligonucleotide having an affinity to a complimentary binding site of a target nucleic acid.

34. The device of claim 19, wherein the ligand molecule is an aptamer having an affinity to a protein-based molecule.

35. The device of claim 19, wherein the ligand molecule is a lectin having an affinity to a receptor site of a bacteria cell.

36. A method of using a tube to collect a target substance in a fluid, comprising:
providing a catalyst material that is reactive to a fuel fluid on an inner wall of a tube to generate bubbles that propel the tube in the fuel fluid, wherein the tube includes two or more layers with a first opening having a smaller diameter than a second opening of the tube; and
using a molecular layer on an external surface of the tube to selectively collect a target substance in the fuel fluid.

37. The method of claim 36, wherein the tube has a diameter between 280 nm to 1 mm.

38. The method of claim 36, wherein the tube has a diameter of substantially 50 μm for the second opening and a diameter of substantially 30 μm for the first opening.

39. The method of claim 36, wherein the fuel fluid includes a plurality of the target substance and a plurality of a non-target substance.

40. The method of claim 36, wherein the target substance includes at least one of cancer cells, bacterial cells, nucleic acids, or protein antigens.

41. The method of claim 36, further comprising:
guiding the tube with an external control to steer a pointing direction of the tube while being propelled by the bubbles.

42. The method of claim 41, wherein the external control includes an external magnetic field to magnetically steer the pointing direction of the tube.

43. The method of claim 36, wherein the target substance in the fuel fluid is contained in a sample reservoir that is connected to a channel that connects the sample reservoir to a clean reservoir.

44. The method of claim 43, further comprising:
transporting the tube having the collected target substance from the sample reservoir to the clean reservoir.

45. The method of claim 44, further comprising:
releasing the collected target substance from the tube into the fuel fluid within the clean reservoir.

46. The method of claim 45, wherein the sample reservoir, the channel, and the clean reservoir is contained on a lab-on-a-chip system.

47. The method of claim 46, wherein the lab-on-a-chip system comprises at least one of fluorescence microscopy operable to conduct polymer chain reaction (PCR), gel electrophoresis, or genetic sequencing.

* * * * *

SEQUENCE LISTING

```
<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide: Thiolated capture
      probe, SHCP
<220> FEATURE:
<221> NAME/KEY: misc_feature
<222> LOCATION: (1)..(1)
<223> OTHER INFORMATION: Thiol at 5'-end

<400> SEQUENCE: 1 tattaactt actcc                                                      15
```

-continued

```
<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide: Detector probe,
      Biotin-DP
<220> FEATURE:
<221> NAME/KEY: misc_feature
<222> LOCATION: (15)..(15)
<223> OTHER INFORMATION: Biotin at 3'-end

<400> SEQUENCE: 2
cttcctcccc gctga                                                  15

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide: Complementary target
<220> FEATURE:
<221> NAME/KEY: misc_feature
<222> LOCATION: (1)..(1)
<223> OTHER INFORMATION: Biotin at 5'-end

<400> SEQUENCE: 3
tcagcgggga ggaagggagt aaagttaata                                  30

<210> SEQ ID NO 4
<211> LENGTH: 37
<212> TYPE: DNA
<213> ORGANISM: Artificial Sequence
<220> FEATURE:
<223> OTHER INFORMATION: Synthetic oligonucleotide: Non-complementary
      sequence, NC
<220> FEATURE:
<221> NAME/KEY: misc_feature
<222> LOCATION: (1)..(1)
<223> OTHER INFORMATION: Biotin at 5'-end

<400> SEQUENCE: 4
ctggggtgaa gtcgtaacaa ggtaaccgta ggggaac                          37

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide: 3-Base mismatched
      sequence, 3-MM
<220> FEATURE:
<221> NAME/KEY: misc_feature
<222> LOCATION: (1)..(1)
<223> OTHER INFORMATION: Biotin at 5'-end

<400> SEQUENCE: 5
tcagcgggga ggaagggagt cacgtgaata                                  30
```